US012584934B2

(12) United States Patent
Wakamiya et al.

(10) Patent No.: US 12,584,934 B2
(45) Date of Patent: Mar. 24, 2026

(54) QUALITY CONTROL METHOD OF SPECIMEN ANALYSIS SYSTEM AND SPECIMEN ANALYSIS SYSTEM

(71) Applicant: SYSMEX CORPORATION, Kobe (JP)

(72) Inventors: Yuji Wakamiya, Kobe (JP); Toru Uemura, Kobe (JP); Yuichiro Ohmae, Kobe (JP); Hidetaka Hayama, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 306 days.

(21) Appl. No.: 17/685,596

(22) Filed: Mar. 3, 2022

(65) Prior Publication Data

US 2022/0283194 A1 Sep. 8, 2022

(30) Foreign Application Priority Data

| Mar. 4, 2021 | (JP) | ................................. | 2021-034851 |
| Mar. 4, 2021 | (JP) | ................................. | 2021-034852 |
| Mar. 4, 2021 | (JP) | ................................. | 2021-034853 |

(51) Int. Cl.
*G01N 35/00* (2006.01)
*B01L 3/00* (2006.01)
(Continued)

(52) U.S. Cl.
CPC ...... *G01N 35/00613* (2013.01); *B01L 3/5025* (2013.01); *G01N 1/44* (2013.01);
(Continued)

(58) Field of Classification Search
CPC ....... G01N 35/00594; G01N 35/00603; G01N 35/00613
See application file for complete search history.

(56) References Cited

U.S. PATENT DOCUMENTS

| 6,221,668 B1 | 4/2001 | Ryan |
| 8,029,732 B2 | 10/2011 | Le Comte |

(Continued)

FOREIGN PATENT DOCUMENTS

| CN | 101256194 A | 9/2008 | |
| CN | 102768286 A | * 11/2012 | ....... G01N 35/00623 |

(Continued)

OTHER PUBLICATIONS

Office Action issued on Jan. 31, 2023 in a counterpart Japanese patent application.

(Continued)

*Primary Examiner* — Herbert K Roberts
(74) *Attorney, Agent, or Firm* — BUCHANAN INGERSOLL & ROONEY PC

(57) ABSTRACT

A quality control method of a specimen analysis system is disclosed, including: receiving a setting of a quality control measurement condition from a user; determining at least one quality control specimen to be used for quality control measurement from among a plurality of the quality control specimens stored in a storage, according to the quality control measurement condition and information on the quality control specimens that are stored in the storage section; taking out the determined quality control specimen from the storage; transporting the determined quality control specimen to a measurement unit; and measuring the transported quality control specimen by the measurement unit.

21 Claims, 55 Drawing Sheets

(51) Int. Cl.

| | |
|---|---|
| *G01N 1/44* | (2006.01) |
| *G01N 33/48* | (2006.01) |
| *G01N 33/96* | (2006.01) |
| *G01N 35/02* | (2006.01) |
| *G01N 35/10* | (2006.01) |

(52) U.S. Cl.

CPC ....... *G01N 33/96* (2013.01); *G01N 35/00712* (2013.01); *G01N 35/0092* (2013.01); *G01N 35/02* (2013.01); *G01N 35/10* (2013.01); *B01L 2200/10* (2013.01); *B01L 2300/0609* (2013.01); *B01L 2300/0663* (2013.01); *B01L 2300/1805* (2013.01); *B01L 2300/1883* (2013.01); *G01N 2035/00346* (2013.01)

(56) References Cited

U.S. PATENT DOCUMENTS

| | | | |
|---|---|---|---|
| 9,483,441 B2 | 11/2016 | Li | |
| 9,513,282 B2* | 12/2016 | Katou | G01N 33/726 |
| 10,012,664 B2 | 7/2018 | Wasson et al. | |
| 2005/0037502 A1 | 2/2005 | Miller | |
| 2006/0263905 A1* | 11/2006 | Mishima | G01N 33/56972 436/520 |
| 2009/0104704 A1 | 4/2009 | Wang | |
| 2009/0142844 A1 | 6/2009 | Le Comte | |
| 2011/0204133 A1 | 8/2011 | Sakata | |
| 2013/0111978 A1* | 5/2013 | Mizumoto | G01N 35/1016 73/61.59 |
| 2016/0327582 A1* | 11/2016 | Koshimura | G01N 21/272 |
| 2017/0176481 A1 | 6/2017 | Accurso et al. | |
| 2018/0209999 A1 | 7/2018 | Han | |
| 2019/0049383 A1* | 2/2019 | Kikuchi | G01N 15/1031 |
| 2019/0277869 A1 | 9/2019 | Stein et al. | |
| 2019/0346466 A1* | 11/2019 | Fujimoto | G01N 15/14 |

FOREIGN PATENT DOCUMENTS

| | | |
|---|---|---|
| CN | 103348250 A | 10/2013 |
| CN | 111551757 A | 8/2020 |
| CN | 111796106 A | 10/2020 |
| EP | 2 703 819 A1 | 3/2014 |
| EP | 3751284 A1 | 12/2020 |
| JP | H08-262031 A | 10/1996 |
| JP | 2005-274289 A | 10/2005 |
| JP | 2008-046144 A | 2/2008 |
| JP | 2009-500619 A | 1/2009 |
| JP | 2009-036513 A | 2/2009 |
| JP | 2009092297 A | 4/2009 |
| JP | 2009115614 A | 5/2009 |
| JP | 2009-168730 A | 7/2009 |
| JP | 2010-121936 A | 6/2010 |
| JP | 2011-226868 A | 11/2011 |
| JP | 2012-112832 A | 6/2012 |
| JP | 2013-011614 A | 1/2013 |
| JP | 2013-024691 A | 2/2013 |
| JP | 2013-024881 A | 2/2013 |
| JP | 2013-076624 A | 4/2013 |
| JP | 2013-079888 A | 5/2013 |
| JP | 2014-048215 A | 3/2014 |
| JP | 2015-135282 A | 7/2015 |
| JP | 2018-105807 A | 7/2018 |
| JP | 6464026 A | 2/2019 |
| JP | 2019506619 A | 3/2019 |
| JP | 6660844 B | 3/2020 |
| JP | 2020-056593 A | 4/2020 |
| JP | 2020-094843 A | 6/2020 |
| JP | 2021-004798 A | 1/2021 |
| JP | 2021-517248 A | 7/2021 |
| JP | 2022-135204 A | 9/2022 |
| KR | 101777750 B1 | 9/2017 |
| WO | 2009099148 A1 | 8/2009 |
| WO | 2019/191531 A1 | 10/2019 |
| WO | 2021/014697 A1 | 1/2021 |

OTHER PUBLICATIONS

Office Action issued on Jan. 31, 2023 in a counterpart Japanese patent application or the related U.S. Appl. No. 17/685,582.
Office Action issued on Jan. 31, 2023 in a counterpart Japanese patent application or the related U.S. Appl. No. 17/685,615.
Extended European search report (EESR) issued on Jul. 28, 2022 in a counterpart European patent application.
Extended European search report (EESR) issued on Jul. 29, 2022 in a counterpart European patent application for the related U.S. Appl. No. 17/685,582.
Extended European search report (EESR) issued on Jul. 29, 2022 in a counterpart European patent application for the related U.S. Appl. No. 17/685,615.
Office Action (Communication pursuant to Article 94(3) EPC) issued on Jul. 10, 2024, by the European Patent Office in corresponding European Application No. 22 159 970.7-1001. (7 pages).
Communication pursuant to Article 94(3) EPC issued on Jul. 30, 2024 in corresponding European patent application No. 22159962.4 by the European Patent Office, 5 pages.
Communication pursuant to Article 94(3) EPC issued on Aug. 5, 2024 in corresponding European patent application No. 22159954.1 by the European Patent Office, 5 pages.
Japanese Office Action issued on Aug. 1, 2024 in corresponding Japanese patent application No. 2023-111126 by the Japanese Patent Office, 6 pages.
Japanese Office Action issued on Aug. 1, 2024 in corresponding Japanese patent application No. 2023-052921 by the Japanese Patent Office, 5 pages.
Japanese Office Action issued on Aug. 1, 2024 in corresponding Japanese patent application No. 2023-175323 by the Japanese Patent Office, 6 pages.
Opposition to Patent issued on Jan. 11, 2024 in a counterpart Japanese patent No. 7307758B2.
Notice of Amendment issued on Feb. 5, 2024 in a counterpart Japanese patent No. 7307758B2.
Notice of Reasons for Revocation issued on Mar. 25, 2024 in a counterpart Japanese patent No. 7307758B2.
Sysmex Corp, "Precision Management", Sysmex Journal Web, vol. 17, No. 1, 2016, https://www.sysmex.co.jp/products_solutions/library/journal/vol17_no1/bfvlfm000000cnhd-att/Vol17_1_05.pdf; Cited in a "Submission of Publications, etc." issued on Mar. 29, 2024 in a counterpart Japanese application No. 2023-175323.
Notice of Submission of Publications, etc. on Mar. 29, 2024 in a counterpart Japanese patent application No. 2023-175323.
U.S. Office Action issued by the U.S. Patent and Trademark Office in counterpart U.S. Appl. No. 17/685,615 (16 pgs).
Office Action (Notice of Reasons for Refusal) issued on Apr. 15, 2025, by the Japanese Patent Office in corresponding Japanese Patent Application No. 2023-111336, and an English Translation of the Office Action. (9 pages).
Office Action (Notice of Reasons for Refusal) issued on Apr. 15, 2025, by the Japanese Patent Office in corresponding Japanese Patent Application No. 2023-1115555, and an English Translation of the Office Action. (9 pages).
Office Action (Notice of Reasons for Refusal) issued on Apr. 15, 2025, by the Japanese Patent Office in corresponding Japanese Patent Application No. 2023-111576, and an English Translation of the Office Action. (8 pages).
Office Action (Notice of Reasons for Refusal) issued on Apr. 15, 2025, by the Japanese Patent Office in corresponding Japanese Patent Application No. 2023-176620, and an English Translation of the Office Action. (8 pages).
Office Action (Notice of Reasons for Refusal) issued on Apr. 15, 2025, by the Japanese Patent Office in corresponding Japanese Patent Application No. 2023-176644, and an English Translation of the Office Action. (6 pages).
U.S. Office Action issued by the U.S. Patent and Trademark Office on May 19, 2025 in counterpart U.S. Appl. No. 17/685,582 (19 pgs).
Ernst et al., "Procedures for the Collection of Diagnostic Blood Specimens by Venipuncture; Approved Standard-Sixth Edition", Clinical and Laboratory Standards Institute, H3-A6, Vol. 27, No. 26, Oct. 2007, (56 pgs).

(56)                    References Cited

OTHER PUBLICATIONS

Koepke et al., "Calibration and Quality Control of Automated Hematology Analyzers; Proposed Standard", NCCLS, H38-P, Vol. 19, No. 7, Apr. 1999 (51 pgs).
Japanese Office Action issued by the Japan Patent Office on Jan. 31, 2023 in counterpart Japanese Patent Application No. 2021-195015 w/English machine translation (7 pgs).
Extended European Search Report issued by the European Patent Office on Apr. 12, 2023 in counterpart European Patent Application No. 22210085.1 (8 pgs).
Partial Extended European Search Report issued by the European Patent Office on Oct. 12, 2023 in counterpart European Patent Application No. 23175565.3 (13 pgs).
Extended European Search Report issued by the European Patent Office on Feb. 13, 2024 in counterpart European Patent Application No. 23175565.3 (15 pgs).
Communication pursuant to Article 94(3) EPC issued by the European Patent Office on Jun. 11, 2024 in counterpart European Patent Application No. 22210085.1 (12 pgs).
Sysmex America Inc., "XN-3100 Automated Hematology Systems Scalable Automation Quick Guide", 2017 (30 pgs).
Russian Office Action and Search Report issued on Aug. 7, 2025 by the Federal Institute of Industrial Property (FIIP) in Russian patent application No. 2022105656, 25 pages. (With English Translation).
Chinese Office Action issued on Jan. 16, 2026, by the State Intellectual Property Office of People's Republic of China in corresponding Chinese Patent Application No. 202511574425.8, with English translation (36 pgs).
Chinese Office Action issued on Jan. 31, 2026, by the State Intellectual Prioperty Office of People's Republic of China in corresponding Chinese Patent Application No. 202511563613.0, with English translation (28 pgs).

* cited by examiner

TOP

LEFT ← → REAR

FRONT ← → RIGHT

BOTTOM

REAR

LEFT ←→ RIGHT

FRONT

FIG. 14

REAR

LEFT ←→ RIGHT

FRONT

| Level 1 : 27 | Level 2 : 79 | Level 3 : 5 |
| --- | --- | --- |

| Pos | Level | Lot | Test | Exp. Date |
| --- | --- | --- | --- | --- |
| 1 | Level 1 | A01XXXX | 3 | 2021/3/30 |
| 2 | Level 1 | A01XXXX | 24 | 2021/3/30 |
| 3 | Level 2 | B01XXXX |  | 2021/4/5 |
| 4 | Level 2 | A002XXX | 7 | 2021/6/30 |
| 5 | Level 2 | A002XXX | 24 | 2021/10/1 |
| 6 | Level 2 | B002XXX | 24 | 2021/2/1 |
| 7 | Level 2 | C001XXX | 24 | 2021/5/1 |
| 8 | Level 3 | D001XXX | 5 | 2021/4/1 |
| 9 | – |  |  |  |

2001A

| CCA | RACK |
| --- | --- |
| 15+ | 2 |

Waste box

QC    CCA

| Temperature | |
| --- | --- |
| Cooler | 4.3°C |
| Heater | 22.8°C |
| Room | 21.3°C |

Figure 25:
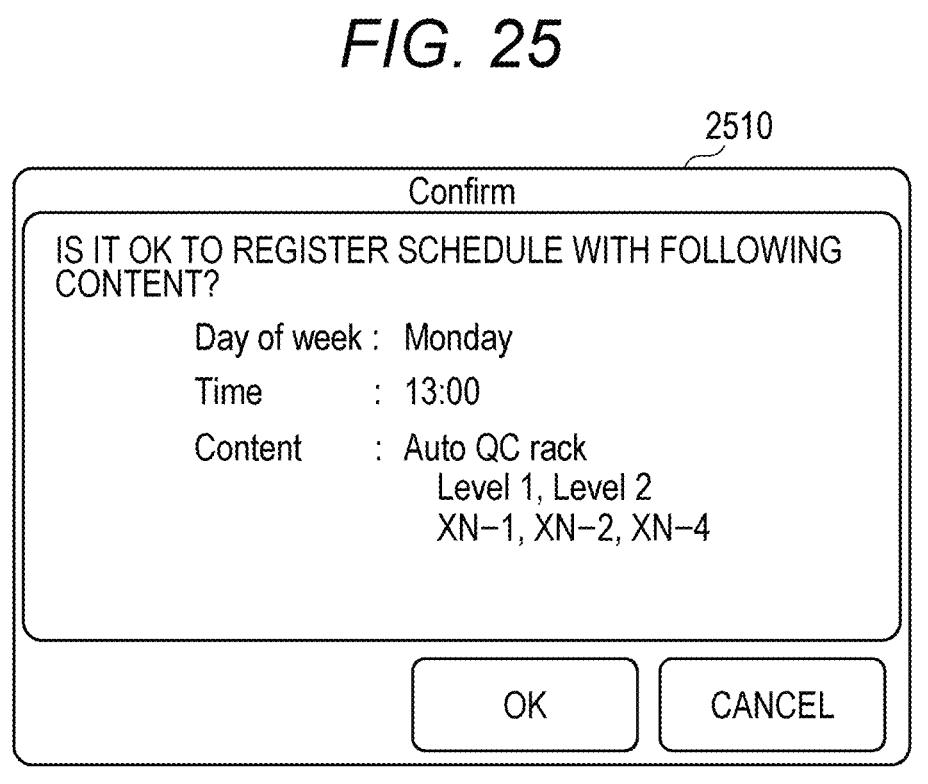

Confirm

IS IT OK TO REGISTER SCHEDULE WITH FOLLOWING
CONTENT?

Day of week :  Monday

Time            :  13:00

Content         :  Auto QC rack
                    Level 1, Level 2
                    XN-1, XN-2, XN-4

OK          CANCEL

FIG. 29

| Pos | Level | Lot | Test | Exp. Date |
|---|---|---|---|---|
| 1 | Level 1 | A01XXXX | 3 | 2021/3/30 |
| 2 | Level 1 | A01XXXX | 24 | 2021/3/30 |
| 3 | Level 2 | B01XXXX | 0 | 2021/4/5 |
| 4 | Level 2 | A002XXX | 7 | 2021/6/30 |
| 5 | Level 2 | A002XXX | 24 | 2021/10/1 |
| 6 | Level 2 | B002XXX | 24 | 2021/10/1 |
| 7 | Level 2 | C001XXX | 24 | 2021/5/1 |
| 8 | Level 3 | D001XXX | 5 | 2021/4/1 |
| 9 | - | | | |

*FIG. 42A*
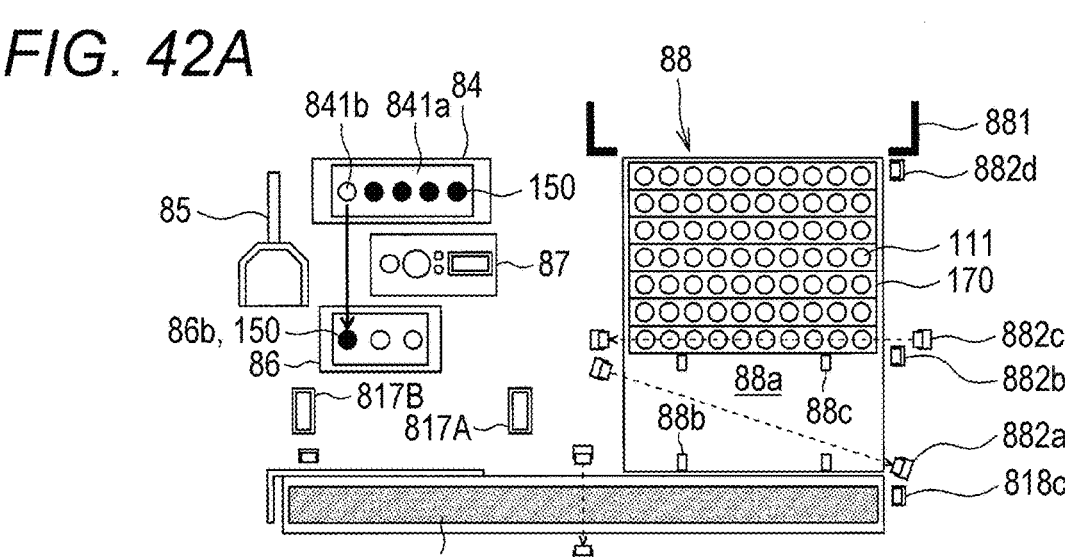
*FIG. 42B*
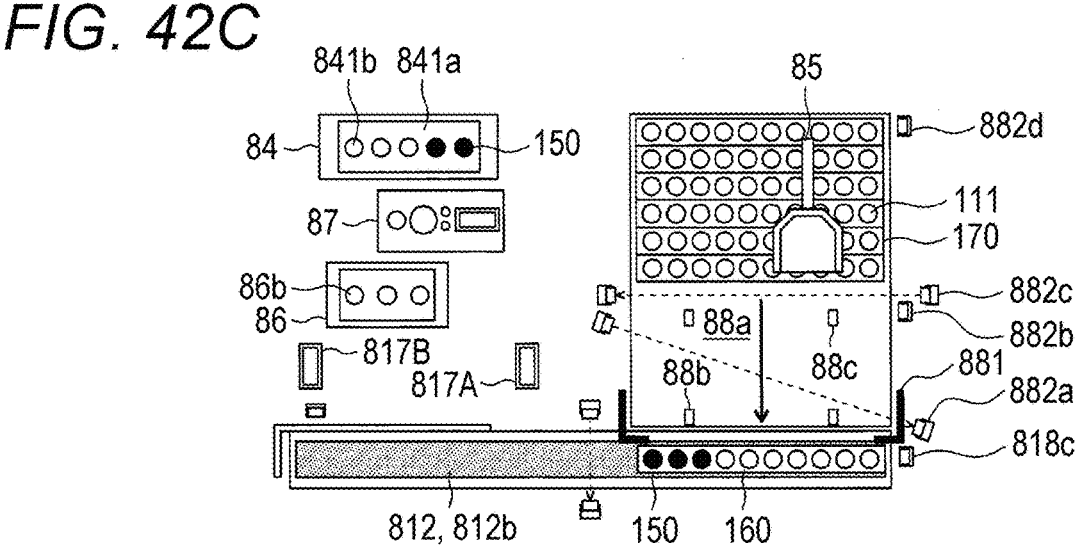
*FIG. 42C*

FIG. 46

CASE D

Auto-QC CONDITIONS
· LEVEL: Level 1, Level 2
· OBJECT UNIT: XN1, XN2, XN3, XN4
· BLOCK STRADDLE: IMPOSSIBLE

CASE E

Auto-QC CONDITIONS
· LEVEL: Level 1, Level 2
· OBJECT UNIT: XN1, XN2, XN3, XN4
· BLOCK STRADDLE: POSSIBLE
· RETEST SETTING: YES (EACH UNIT×2)

CASE F

| Pos | Level | Lot | Test | Exp. Date |
|-----|-------|-----|------|-----------|
| 1 | Level 1 | P001 | 12 | 2021/3/30 |
| 2 | Level 1 | P002 | 24 | 2021/3/30 |
| 3 | Level 1 | P002 | 24 | 2021/4/5 |
| 4 | Level 2 | Q001 | 12 | 2021/6/30 |
| 5 | Level 2 | Q002 | 24 | 2021/10/1 |
| 6 | Level 2 | Q002 | 24 | 2021/10/1 |
| 7 | | | | |
| 8 | | | | |
| 9 | | | | |

Auto-QC CONDITIONS
· LEVEL: Level 1, Level 2
· OBJECT UNIT: XN1, XN2, XN3, XN4
· BLOCK STRADDLE: POSSIBLE
· INTER-LOT DIFFRENCE CHECK FUNCTION ON

QUALITY CONTROL METHOD OF SPECIMEN ANALYSIS SYSTEM AND SPECIMEN ANALYSIS SYSTEM

CROSS REFERENCE TO RELATED APPLICATIONS

This application claims priority from prior Japanese Patent Application Nos. 2021-034853, 2021-034852, 2021-034851, filed on Mar. 4, 2021, the entire contents of all of which are incorporated herein by reference.

FIELD OF THE INVENTION

The present disclosure relates to a quality control method of a specimen analysis system and a specimen analysis system.

BACKGROUND

Conventionally, a specimen analysis system including an analyzer for analyzing a specimen containing cells derived from a living body such as blood cell is widely known. In such a system, it is necessary to periodically confirm that there is no abnormality in a measurement result of the analyzer using a quality control material containing a cell with a known concentration, and manage measurement accuracy.

JP 2010-121936 A discloses a specimen processing system including a cooling storage for storing a quality control specimen. In the system of JP 2010-121936 A, one specimen with the closest expiration date is selected from the quality control specimens stored in the cooling storage, and the selected specimen is transported to an analyzer to perform quality control measurement.

The system of JP 2010-121936 A is configured to automatically select a quality control specimen to be used according to certain conditions. However, operation of quality control is generally different for each laboratory, and it is desirable that the quality control conditions can be flexibly set according to the operation.

SUMMARY OF THE INVENTION

The scope of the invention is defined solely by the appended claims, and is not affected to any degree by the statements within this summary.

According to the invention, a quality control method of a specimen analysis system using a quality control specimen is provided. The method includes receiving setting of quality control measurement condition from a user, determining at least one quality control specimen to be used for quality control measurement from among a plurality of the quality control specimens stored in a storage, according to the quality control measurement condition and information of the quality control specimens, taking out the determined quality control specimen from the storage, transporting the determined quality control specimen to a measurement unit, and measuring the transported quality control specimen by the measurement unit.

According to one or more embodiments, a specimen analysis system is provided. The specimen analysis system includes at least one measurement unit, a supply unit including a storage for storing a plurality of quality control specimens, a transport unit that transports the quality control specimens stored in the storage to the measurement unit, and a control unit, in which the control unit receives setting of quality control measurement condition from a user, the control unit determines at least one quality control specimen to be used for quality control measurement from among a plurality of the quality control specimens stored in the storage, according to the quality control measurement conditions and information of the quality control specimens, the control unit controls the supply unit and the transport unit to take out the determined quality control specimen from the storage and transport the determined quality control specimen to the measurement unit, and the measurement unit measures the transported quality control specimen.

BRIEF DESCRIPTION OF THE DRAWINGS

FIG. 1 is a diagram schematically showing a specimen analysis system;

FIG. 14 is a perspective view showing an internal structure of a supply unit, viewing a rack housing section from front side;

FIG. 19 is an example of a device status screen displayed when a device status icon on a home screen is pressed;

FIG. 23 is an example of a schedule screen displayed when a schedule icon on a home screen is pressed;

FIG. 25 is an example of a confirmation screen displayed when an auto QC schedule is input and OK button is pressed on a schedule registration screen;

FIG. 29 is an example of a database of QC specimens stored in a control section of a supply unit;

FIGS. 42A, 42B, and 42C are diagrams showing actions of a supply unit in auto QC;

FIG. 46 is a diagram showing a specific example of a combination of QC specimen containers;

DETAILED DESCRIPTION

Hereinafter, examples of an embodiment or embodiments of the quality control method of a specimen analysis system and the specimen analysis system will be described in detail with reference to the drawings. The one or more embodiments described below are merely examples, and the scope of the invention is not limited to the following one or more embodiments. It is further included within the scope of the invention that components of a plurality of embodiments and modifications described below are selectively combined.

Figure 1:
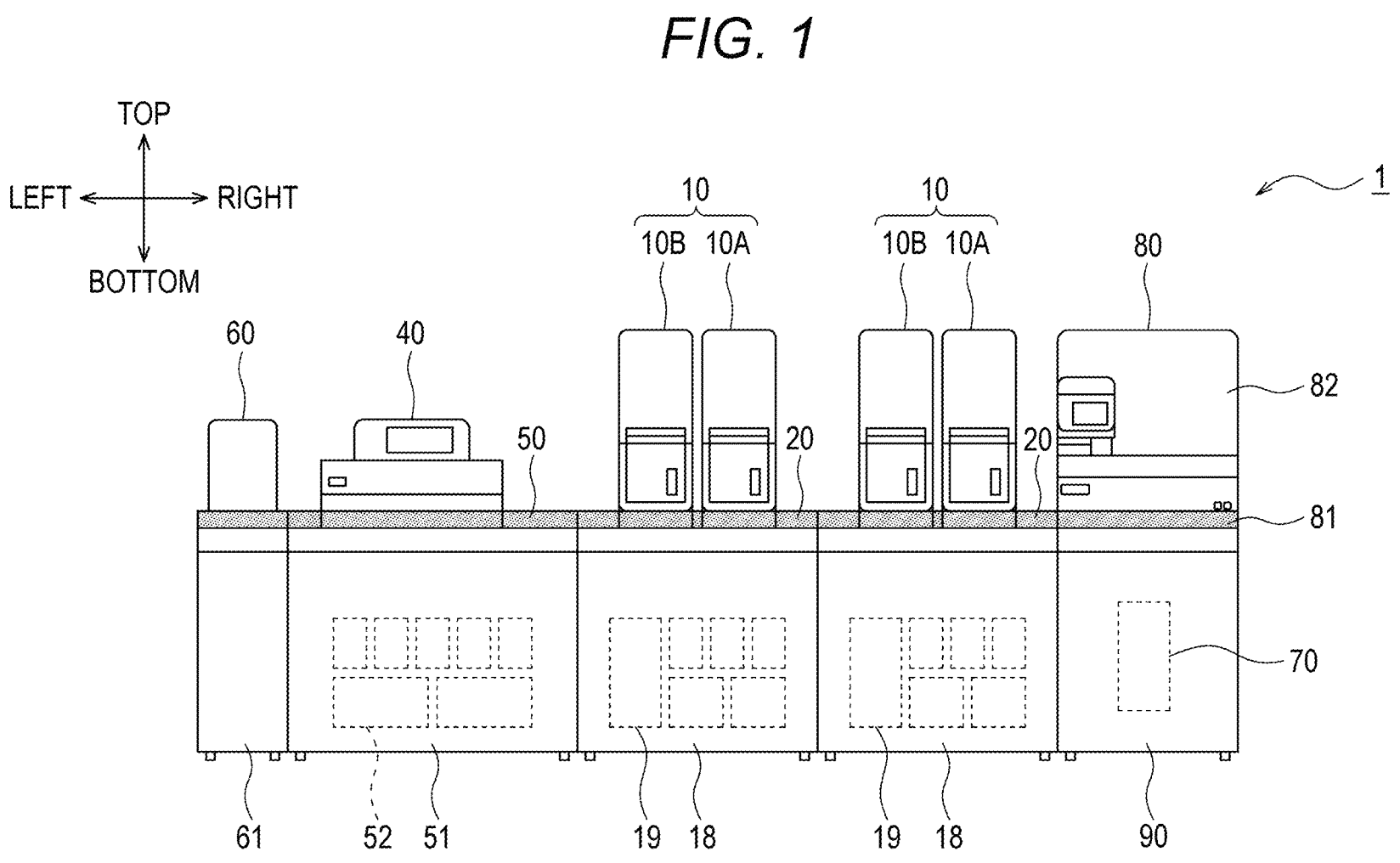
Figure 2:
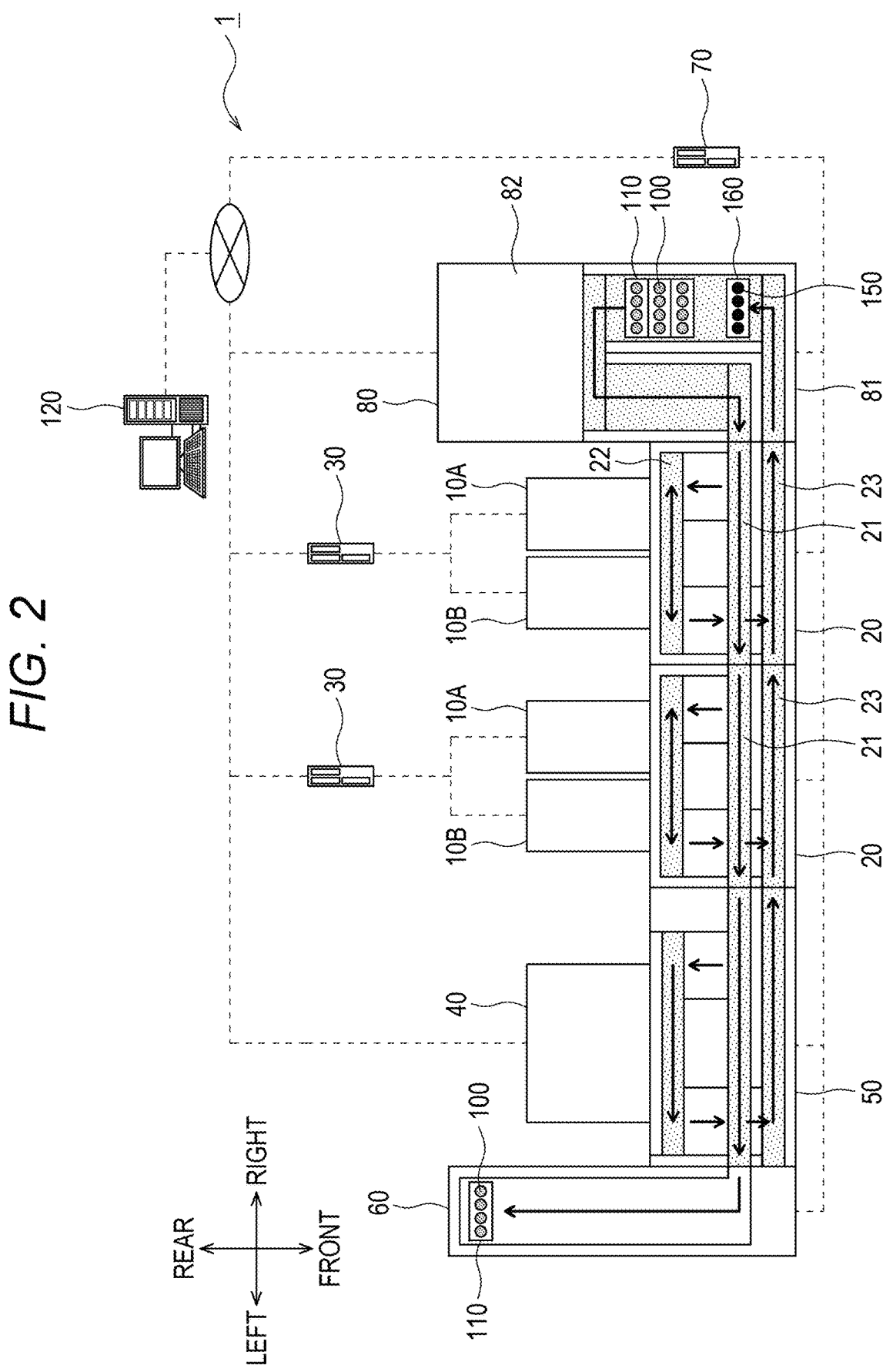
FIG. 2 is a diagram schematically showing a specimen analysis system.

FIGS. 1 and 2 are diagrams schematically showing an overall configuration of specimen analysis system 1 which is an example of the embodiment or embodiments. As shown in FIGS. 1 and 2, the specimen analysis system 1 includes a first measurement unit 10A, a second measurement unit 10B, a transport unit 20, and a control unit 30. The first measurement unit 10A and the second measurement unit 10B are analyzers for analyzing a specimen containing cell of biological origin, and are arranged next to each other. Hereinafter, the two measurement units constituting the analyzer are collectively referred to as a "measurement block". The transport unit 20 is arranged in front of the measurement block. In the present specification, for convenience of explanation, terms indicating directions such as front-rear, left-right, top-bottom and the like shown in the drawings are used.

The specimen analysis system 1 includes two modules 10 including the measurement block, the transport unit 20, and the control unit 30. The two modules 10 are arranged next to each other in the left-right direction. The module 10 is provided with one control unit 30 for two measurement units. The first measurement unit 10A and the second measurement unit 10B are configured as devices for counting blood cells in a blood specimen, and have the same hardware configuration as each other. Whole blood is used as the blood specimen.

The specimen analysis system 1 includes a supply unit 80 in which a specimen rack 110 is set on the upstream side of the two modules 10. A plurality of specimen containers 100 are housed in the specimen rack 110. The specimen container 100 is a blood specimen for blood cell measurement, that is, a container containing whole blood. The supply unit 80 is arranged adjacent to one module 10 arranged on the upstream side out of the two modules 10. The supply unit 80 includes a conveyor section 81 for transporting the specimen rack 110 to the module 10. In the present embodiment or embodiments, the specimen rack 110 is set in the conveyor section 81 by a user.

The conveyor section 81 is connected to the transport unit 20 of the module 10. The conveyor section 81 is configured so that the set specimen rack 110 can be transferred to the transport unit 20. As will be described in detail later, in addition to the specimen container 100, a QC specimen container 150 containing a quality control material containing a cell with a known concentration is set in the supply unit 80. The supply unit 80 includes a storage adjustment unit 82 that cools and stores the QC specimen container 150, adjusts the temperature of the quality control material to the measurement temperature, and then sends out the QC specimen container 150 to the conveyor section 81. The QC specimen container 150 contains an amount of quality control material that can be used for multiple measurements. For example, in one QC specimen container 150, an amount of quality control material that can be measured 24 times by the measurement unit is housed. In the following, the amount corresponding to one measurement is also referred to as "1 test".

The upstream side of the specimen analysis system 1 means a side where the specimen rack 110 is set and to be a starting point of transportation, that is, the side where the supply unit 80 is arranged. The downstream side of the specimen analysis system 1 means a side to be an end point of transportation of the specimen rack 110. In FIGS. 1 and 2, the right side of the paper is the upstream side of the specimen analysis system 1, and the left side of the paper is the downstream side of the specimen analysis system 1. The specimen rack 110 set in the supply unit 80 is sent to the transport unit 20 and transferred to the measurement unit by a function of the transport unit 20.

The transport unit 20 includes a plurality of rack transport paths. The transport unit 20 can distribute and supply specimen containers 100 to the first measurement unit 10A and the second measurement unit 10B. The transport unit 20 includes a first transport path 21 for receiving the specimen rack 110 from the upstream side (right side) of the specimen analysis system 1 and transporting the specimen rack 110 to the downstream side (left side), and a second transport path 22 that extends parallel to the first transport path 21 and arranged on the measurement block side of the transport path 21. The second transport path 22 transports the specimen rack 110 in the left-right direction. In the second transport path 22, there is a take-out position P2 (see FIG. 5 and the like illustrated later) in which the specimen container 100 is taken out from the specimen rack 110 and the specimen container 100 is taken into the measurement unit.

The transport unit 20 further includes a third transport path 23. The third transport path 23 extends parallel to the first transport path 21. The third transport path 23 is arranged in the front of the specimen analysis system 1 with respect to the first transport path 21. That is, the transport unit 20 is provided with three rack transport paths arranged in the front-rear direction in the order of the third transport path 23, the first transport path 21, and the second transport path 22 from the front. As will be described in detail later, the third transport path 23 is configured to transport the rack from the downstream side to the upstream side of the specimen analysis system 1. Therefore, when viewing the third transport path 23 alone, the left side is the upstream side of the transport path, and the right side is the downstream side of the transport path.

The specimen analysis system 1 further includes a process unit 40, a transport unit 50, and a collection unit 60. The process unit 40 is a device for preparing a smear of a blood specimen. The collection unit 60 is a device for collecting the used specimen container 100 (specimen rack 110). The process unit 40 is arranged adjacent to one module 10 arranged on the downstream side out of the two modules 10. The collection unit 60 is arranged adjacent to the process unit 40, on the downstream side of the specimen analysis system 1 from the process unit 40.

The transport unit 50 is provided with a rack transport path for transporting the specimen rack 110 to the process unit 40. The transport unit 50 is arranged in front of the process unit 40. The transport unit 50 is connected to the transport unit 20 of the module 10 and the collection unit 60. When the specimen rack 110 does not include the specimen container 100 required to prepare a smear, the specimen rack 110 is transported from the transport unit 50 to the collection unit 60 through the process unit 40.

In the specimen analysis system 1, as a unit for transporting a specimen, from the upstream side, the supply unit 80, the transport unit 20 corresponding to the modules 10 on the upstream side and the downstream side, the transport unit 50 arranged in front of the process unit 40, and the collection unit 60 are arranged in this order, and adjacent units are connected to each other. In the specimen analysis system 1, a continuous rack transport path capable of transporting the specimen rack 110 in the left-right direction from the supply unit 80 to the collection unit 60 is formed. In the examples shown in FIGS. 1 and 2, the adjacent units are directly connected to each other, but another transport path, another unit or the like may be interposed between these units.

In the specimen analysis system 1, the measurement block and the transport unit 20 are mounted on a wagon 18. The wagon 18 contains a reagent container 19 containing reagents to be used in the measurement unit. Similarly, wagons 61 and 90 are provided for the process unit 40, the transport unit 50, the collection unit 60, and the supply unit 80. The wagons 18, 51, 61, 90 preferably have the same height or can be adjusted to the same height so that the rack transport path is along the horizontal plane. The wagon 51 on which the process unit 40 and the transport unit 50 are mounted also contains a reagent container 52 containing reagents such as a staining solution.

The specimen analysis system 1 further includes a transport controller 70 for managing transport of the specimen rack 110 and a QC specimen rack 160. The transport controller 70 is contained in the wagon 90 below the supply unit 80. The transport controller 70 controls rack transport in the rack transport path of the units by transmitting and receiving signals to and from the transport units 20, 50 and 81, the collection unit 60, and the supply unit 80. In the specimen analysis system 1, the units and the transport controller 70 are communicably connected to a host computer 120 via a communication network.

The specimen analysis system 1 is installed, for example, in a hospital laboratory. In this case, an example of the host computer 120 is a laboratory information system (LIS) that is connected to a plurality of test devices and centrally manages specimen information and measurement orders. Information on each specimen container 100 and each QC specimen container 150 is registered in the host computer 120.

In the present specification, a rack in which a container is not housed is referred to as an empty rack 170 (see FIG. 8 and the like illustrated later). A rack obtained by housing the specimen container 100 in the empty rack 170 is referred to as the specimen rack 110. A rack obtained by housing the QC specimen container 150 in the empty rack 170 is referred to as the QC specimen rack 160.

In the specimen analysis system 1, the specimen rack 110 set in the supply unit 80 is transported to the first transport paths 21 of the adjacent transport units 20. When a transport destination is not the module 10 on the upstream side, the specimen rack 110 carried into the first transport path 21 is transported to the transport unit 20 of the module 10 on the downstream side through the first transport path 21. When the transport destination is the module 10 on the upstream side, the specimen rack 110 is transported from the first transport path 21 to the second transport path 22 of this module 10, and initial test, and retest if necessary, are performed in the measurement block of this module 10. The control unit 30 is configured to send the results of the initial test and the retest to the host computer 120.

When the initial test and the necessary retest are finished for all the specimen containers 100 housed in the specimen rack 110, the transport controller 70 inquires the host computer 120 whether or not it is necessary to prepare a smear in the process unit 40 for each specimen container 100. When the specimen rack 110 contains a specimen container 100 for which a smear needs to be prepared, the transport destination of the specimen rack 110 is the process unit 40, and the specimen rack 110 is supplied to the process unit 40 via the transport paths of the transport units 20, 50.

When the specimen rack 110 does not include a specimen container 100 for which a smear needs to be prepared, the transport destination of the specimen rack 110 is the collection unit 60, and the specimen rack 110 is transported to the collection unit 60 via the transport paths of the transport units 20, 50. Also when the smear is prepared in the process unit 40, the specimen rack 110 is transported to the collection unit 60 after the smear is prepared.

Figure 3:
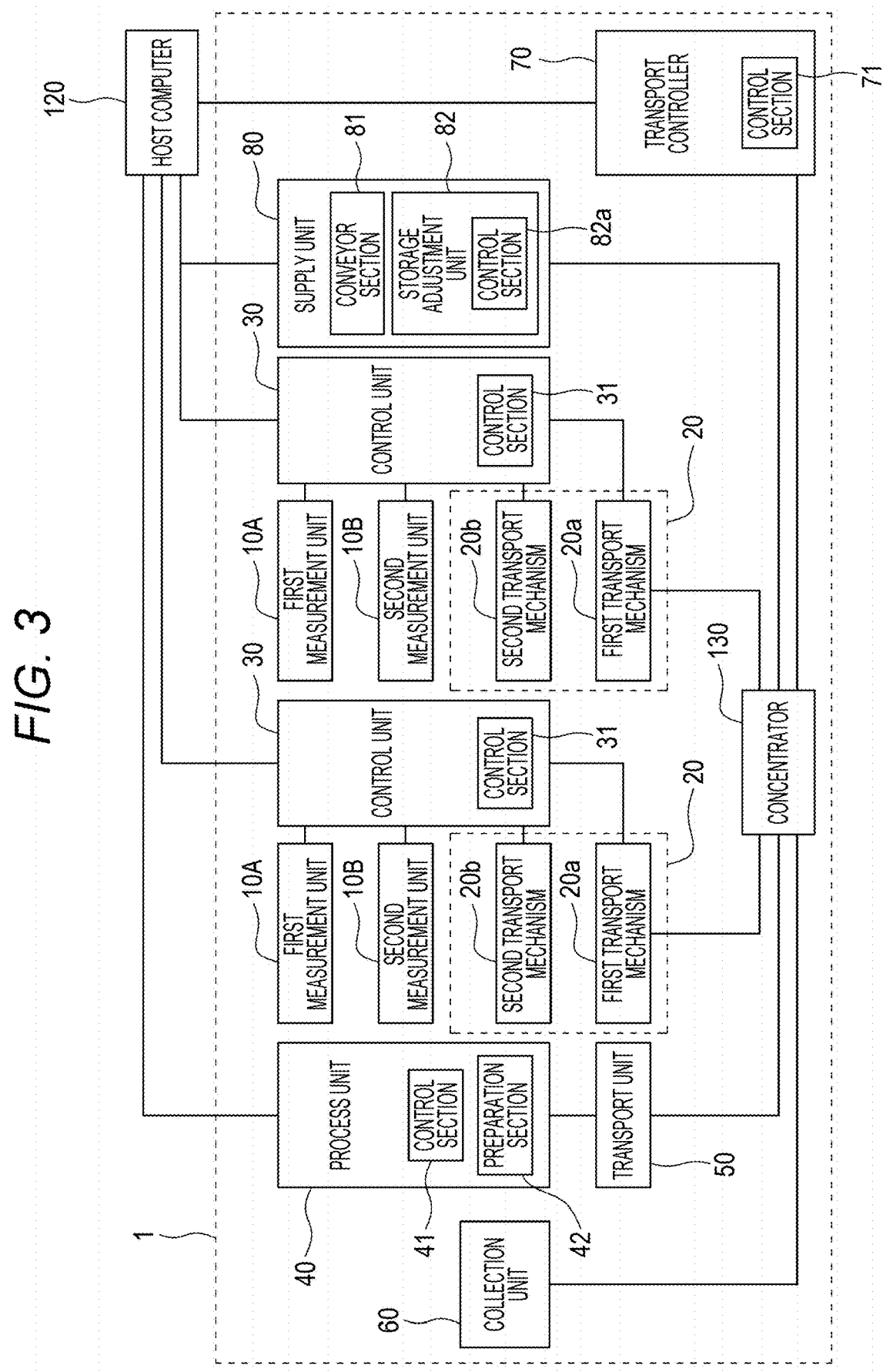
FIG. 3 is a block diagram showing an interconnection relationship between units constituting a specimen analysis system.

FIG. 3 is a block diagram showing a connection relationship between units constituting the specimen analysis system 1. As shown in FIGS. 1, 2 and 3, the control unit 30 is communicably connected to the measurement unit in the same module 10. The control unit 30 controls the measurement unit in the same module 10. The control unit 30 controls, for example, the first measurement unit 10A and the second measurement unit 10B. The control unit 30 also controls a part of the transport unit 20. The control unit 30 is configured to receive the measurement data of the specimen from the first measurement unit 10A and the second measurement unit 10B and generate the measurement result of the specimen according to a measurement item.

The transport unit 20 includes a first transport mechanism 20a whose transport action is controlled by the transport controller 70, and a second transport mechanism 20b whose transport action is controlled by the control unit 30. The first transport mechanism 20a includes parts related to rack transport of the first transport path 21 and the third transport path 23. The second transport mechanism 20b includes parts related to rack transport by the second transport path 22, a first storage section 24, and a second storage section 25 (see FIG. 5). The control unit 30 is communicably connected to the first measurement unit 10A, the second measurement unit 10B, the first transport mechanism 20a, and the second transport mechanism 20b.

The control unit 30 is, for example, a personal computer. The control unit 30 includes a control section 31. The control section 31 includes a processor, a storage section, and an input/output interface as main configuration. The processor is composed of, for example, a CPU. The processor controls an action of each part of the measurement unit and the transport unit by reading and executing a control program installed in the storage section. The processor further executes an analysis program installed in the storage section to analyze the measurement data transmitted from the measurement unit and count or quantify components in the blood such as red blood cells, white blood cells, platelets, and hemoglobin contained in the specimen. The storage section includes a non-volatile memory such as ROM, HDD and SSD, and a volatile memory such as RAM. The control unit 30 is connected to the measurement unit and the transport unit by a LAN cable.

The units constituting the specimen analysis system 1 are communicably connected via a concentrator 130. The concentrator 130 is composed of, for example, a hub. In the present embodiment or embodiments, the first transport mechanism 20a, the transport unit 50, the collection unit 60, the transport controller 70, and the supply unit 80 of the two modules 10 are communicably connected via the concentrator 130. As described above, the units and the transport controller 70 are communicably connected to the host computer 120. For example, the control unit 30 (control section 31) inquires the host computer 120 about the measurement order to acquire the measurement order, and the control unit 30 controls the measurement unit based on the acquired measurement order.

The process unit 40 includes a control section 41 and a preparation section 42. The control section 41 includes, for example, a processor incorporated in the process unit 40 and a storage section. The control section 41 controls the preparation section 42 based on the control program installed in the storage section. The preparation section 42 is configured to suck the specimen from the specimen container 100 to prepare a smear when the specimen container 100 of the smear to be prepared is transported to a predetermined position on the rack transport path of the transport unit 50. An action of the preparation section 42 is controlled by the control section 41. The collection unit 60 collects the specimen rack 110 whose measurement has been completed in either of the two modules 10 and the specimen rack 110 whose smear preparation has been completed via the process unit 40. The collection unit 60 includes a rack transport path, which is controlled by the transport controller 70.

The transport controller 70 is, for example, a personal computer. The transport controller 70 includes a control section 71. A hardware configuration of the control section 71 is the same as that of the control section 31 of the control unit 30. The control section 71 sends a control signal to the supply unit 80, the first transport mechanism 20a, the transport unit 50, and the collection unit 60 via the concentrator 130 to control the transport of the specimen rack 110 and the QC specimen rack 160. The control section 71 is communicably connected to the control unit 30. The control section 71 grasps positions of each specimen rack 110 and each QC specimen rack 160 in the transport path, based on a detection signal of a sensor of each unit.

A control section 82a of the supply unit 80 mainly controls actions of components of the storage adjustment unit 82. In the present embodiment or embodiments, further, auto wake up and auto shut down of each unit of the specimen analysis system 1 are executed by a function of the control section 82a. A hardware configuration of the control section 82a is the same as that of the control sections 31 and 71.

Figure 4:
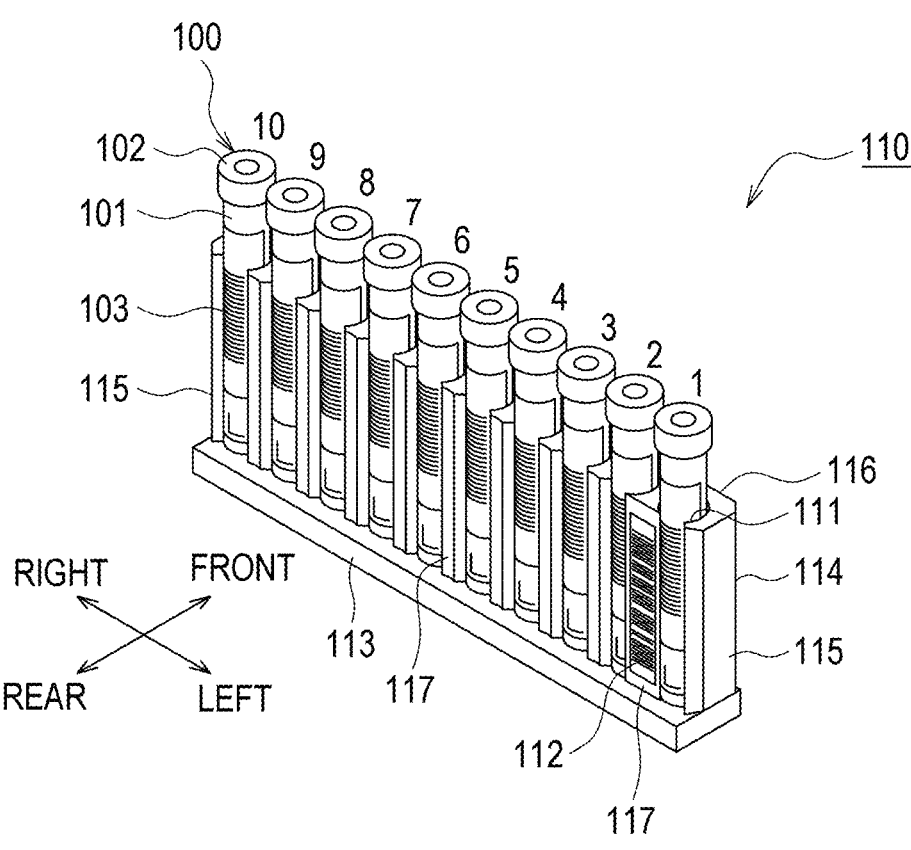
FIG. 4 is a perspective view showing a specimen container and a specimen rack in which a specimen container is housed.

FIG. 4 is a perspective view showing a specimen rack 110 containing in which a plurality of specimen containers 100 are housed. In the present specification, for convenience of explanation, with the specimen rack 110 set in the specimen analysis system 1, a side facing the front of the system is defined as a front side of the specimen rack 110, and a side facing the rear is defined as a rear side of the specimen rack 110.

As shown in FIG. 4, the specimen container 100 includes a bottomed tube 101 containing a blood specimen collected from a subject, and a cap 102 that closes an opening of the tube 101. The tube 101 is, for example, a bottomed cylindrical container made of translucent glass or resin. The opening of the tube 101 is closed with the rubber cap 102, and the internal space for housing the specimen is sealed. The specimen container 100 is provided with a machine-readable label 103. The machine-readable label 103 is, for example, a barcode label on which a barcode indicating a specimen ID is printed. The machine-readable label 103 is attached to the side surface of the tube 101. The specimen ID is identification information that can individually identify the specimen.

The specimen rack 110 (empty rack 170) is a case in which the specimen container 100 is housed and used for transporting the specimen container 100. The specimen rack 110 includes a plurality of housing portions 111 capable of holding the plurality of specimen containers 100 in an upright state. The number of the housing portions 111 is not particularly limited, but in the present embodiment or embodiments, ten housing portions 111 (Nos. 1 to 10) are formed in a row in the left-right direction. The specimen rack 110 is provided with a machine-readable label 112. The machine-readable label 112 is, for example, a barcode label on which a barcode indicating a rack ID is printed. The rack ID is identification information that can individually identify the specimen rack 110.

The specimen rack 110 includes a bottom plate portion 113 having a rectangular shape when viewed from the bottom, and a wall portion 114 that is provided extending in the height direction of the specimen container 100 and supports the specimen container 100. In the specimen rack 110, the specimen container 100 stands substantially perpendicular to the bottom plate portion 113. The wall portion 114 is formed at a height lower than that of the upright specimen container 100. The wall portion 114 includes a pair of side walls 115 formed on the left and right ends of the bottom plate portion 113, a front wall 116 formed along the front end of the bottom plate portion 113 and connecting the two side walls 115, and a plurality of partition walls 117 extending from the front wall 116 toward the rear end side of the bottom plate portion 113. The plurality of partition walls 117 divide a storage space of the specimen container 100. The plurality of partition walls 117 form a plurality (ten in FIG. 4) of housing portions 111.

Nine partition walls 117 are formed on the rack illustrated in FIG. 4, and the machine-readable label 112, which is a bar code label, is attached to the rear surface of a partition wall 117 that separates the first and second housing portions 111. Each housing portion 111 has a large opening upward and rearward. Therefore, the machine-readable label 103 can be read even when the specimen container 100 is housed in the housing portion 111. The machine-readable labels 103 and 112 are not limited to one-dimensional bar code labels as shown in FIG. 4, and may be two-dimensional codes. The machine-readable labels 103 and 112 may be IC tags that can be read by an RFID reader.

Figure 5:
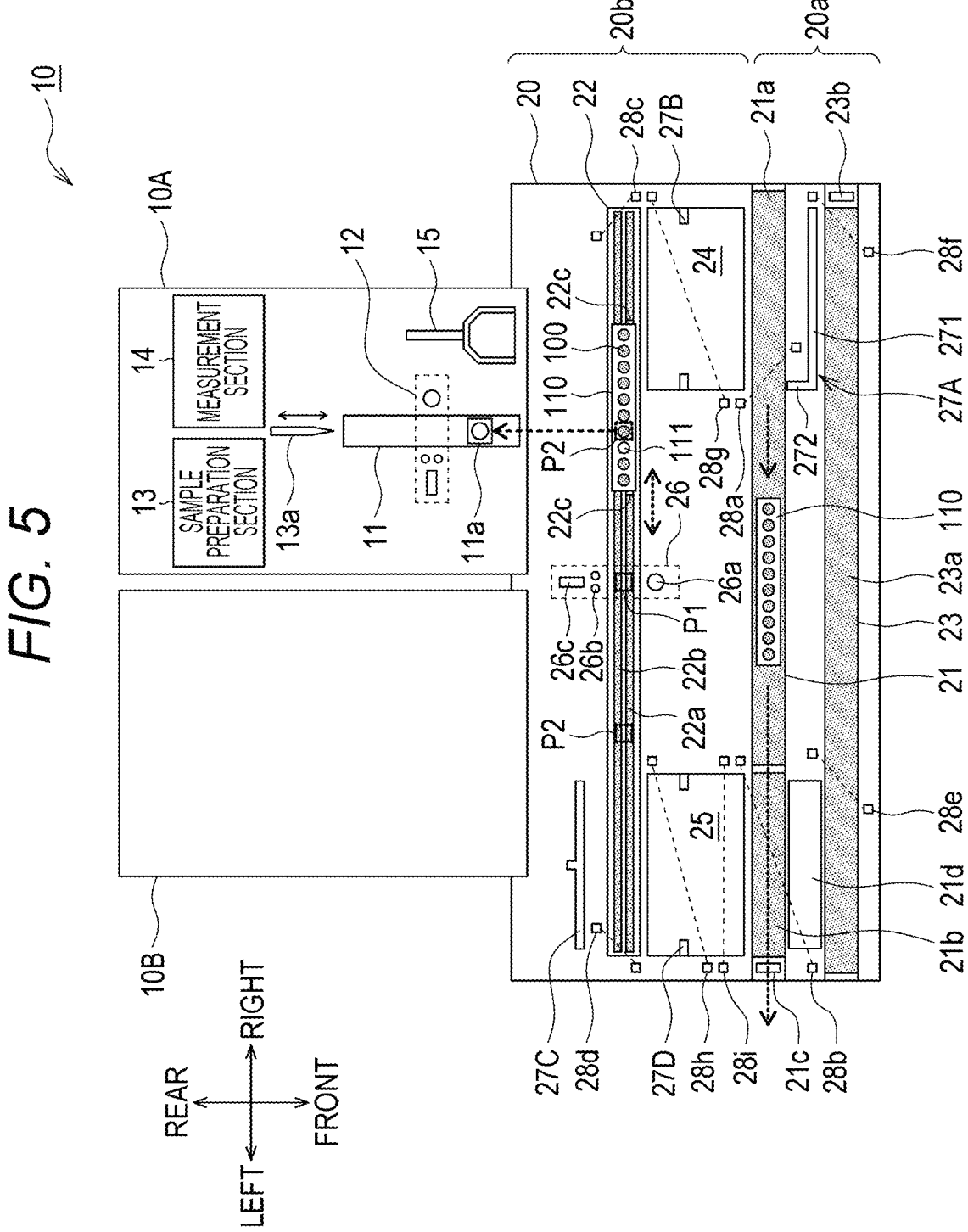
FIG. 5 is a diagram schematically showing configurations of measurement units and a transport unit constituting a specimen analysis system.
Figure 6:
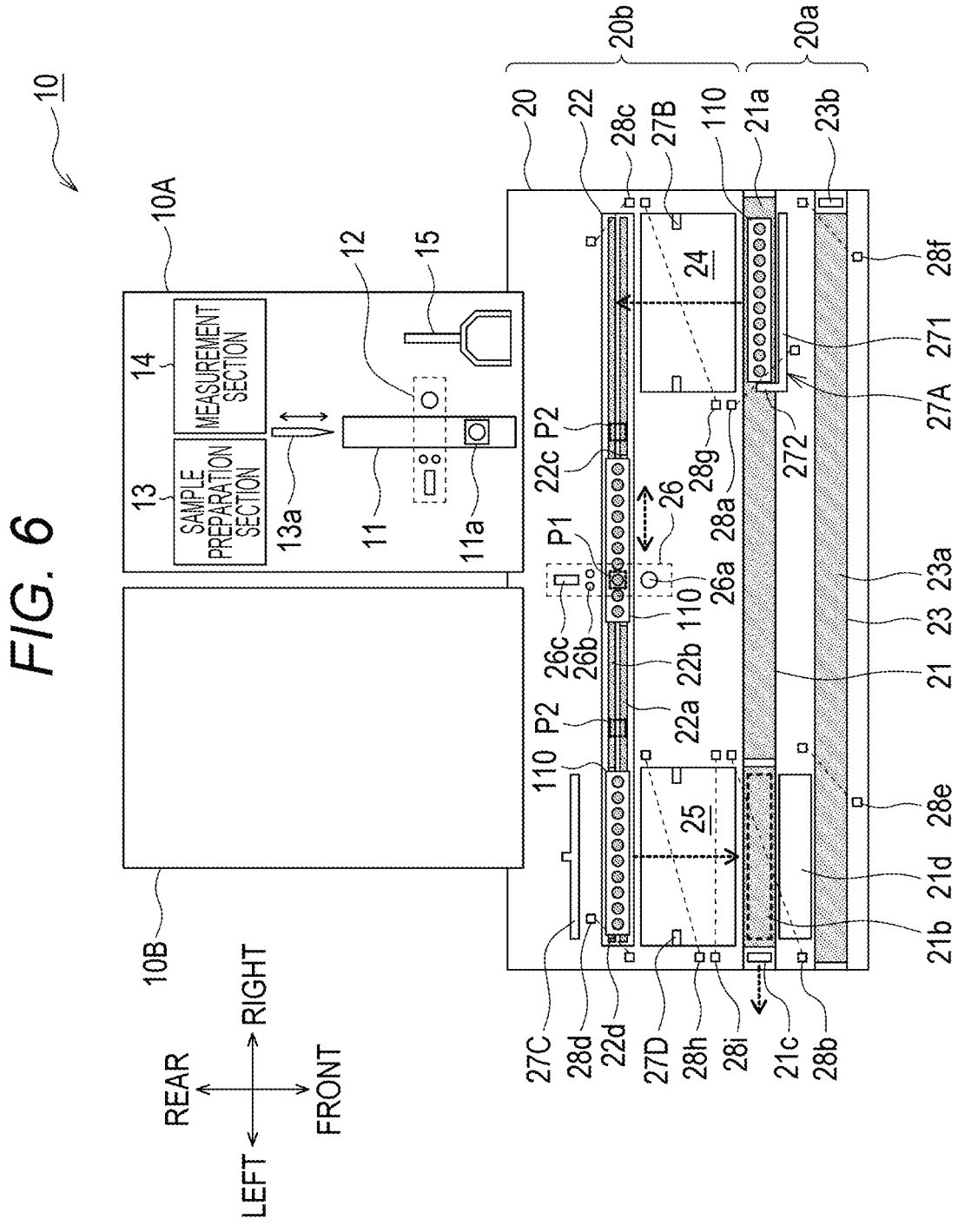
FIG. 6 is a diagram schematically showing configurations of measurement units and a transport unit.

Hereinafter, configurations of the measurement block and the transport unit 20 will be described in detail with reference to FIGS. 5 and 6. In FIG. 5, a plate 272 of a first delivery section 27A is at a position retracted from the first transport path 21. In FIG. 6, the plate 272 is present on the first transport path 21.

Measurement Block (First Measurement Unit 10A, Second Measurement Unit 10B)

As shown in FIGS. 5 and 6, the first measurement unit 10A and the second measurement unit 10B are arranged next to the transport unit 20 in the front-rear direction and behind the transport unit 20. The first measurement unit 10A and the second measurement unit 10B take out the specimen container 100 from the specimen rack 110 transported to the second transport path 22 of the transport unit 20. The first measurement unit 10A and the second measurement unit 10B measure the blood specimen housed in the specimen container 100. Although a configuration of the first measurement unit 10A is illustrated in FIGS. 5 and 6, the second measurement unit 10B also has the same device structure.

The first measurement unit 10A can measure, for example, CBC items and DIFF items. The CBC items include WBC (white blood cell count), RBC (red blood cell count), HGB (hemoglobin content), HCT (hematocrit value), MCV (mean corpuscular volume), MCH (mean corpuscular hemoglobin), MCHC (mean corpuscular hemoglobin concentration), PLT (platelet count), and the like. The DIFF items include NEUT # (neutrophil count), LYMPH # (lymphocyte count), MONO # (monocyte count), EO # (eosinophil count), BASO # (basophil count), and the like. The second measurement unit 10B can measure, for example, RET items, PLT-F items, and WPC items, in addition to the CBC items and the DIFF items. The RET items include RET # (reticulocyte count) and the like. The PLT-F items include, for example, PLT # (platelet count). In the WPC items, for example, abnormal leukocytes of blast cell and lymphocytic system are detected and flagged.

In one embodiment or embodiments, the first measurement unit 10A measures the CBC items and the DIFF items as the initial test. The second measurement unit 10B measures the CBC items and the DIFF items as the initial test. The second measurement unit 10B measures the RET items, the PLT-F items or the WPC items as the retest as necessary. That is, the first measurement unit 10A is a measurement unit dedicated to the initial test, and the second measurement unit 10B is a measurement unit capable of performing the retest in addition to the initial test.

The first measurement unit 10A includes a container transfer section 11, an information reading section 12, a sample preparation section 13, and a measurement section 14. The first measurement unit 10A includes a robot hand 15 for taking out the specimen container 100 from the housing portion 111 of the specimen rack 110 at a predetermined take-out position P2 of the second transport path 22, shaking the taken-out specimen container 100 a predetermined number of times, overturning and stirring the taken-out specimen container 100, and installing the stirred specimen container 100 in the container transfer section 11. The container transfer section 11 has a holding portion 11a that can hold the specimen container 100 in an upright state. The container transfer section 11 is configured such that the holding portion 11a moves in the front-rear direction together with the container transfer section 11. The information reading section 12 is arranged at a position between an installation position where the specimen container 100 is installed by the robot hand 15 and a suction position by a suction tube 13a described later in a transfer route of the specimen container 100 by the container transfer section 11. The information reading section 12 reads the specimen ID from the machine-readable label 103 of the specimen container 100 set in the holding portion 11a.

The sample preparation section 13 includes a suction tube 13a. The sample preparation section 13 penetrates the cap 102 of the specimen container 100 set in the holding portion 11a by the suction tube 13a. The sample preparation section 13 sucks the specimen through the suction tube 13a. The sample preparation section 13 includes, for example, a reaction vessel. The sample preparation section 13 prepares a measurement sample by mixing the sucked specimen and a reagent in the reaction vessel. The reagent is, for example, a diluent, a hemolytic agent, or a staining solution. The measurement section 14 includes, for example, an optical detection part, an electric resistance detection part, and a hemoglobin measurement part. The measurement section 14 measures the measurement sample. When the suction of the specimen is finished, the specimen container 100 is transported forward by the container transfer section 11, and the specimen container 100 is returned to the original housing portion 111 of the specimen rack 110 by the robot hand 15.

The first measurement unit 10A, the second measurement unit 10B, and the second transport mechanism 20b (see FIG. 3), which is a part of the transport unit 20, are controlled by the control unit 30. When performing an initial test, the control unit 30 inquires the host computer 120 about the measurement order of the initial test based on the read specimen ID, and the control unit 30 acquires the measurement order of the specimen from the host computer 120. The control unit 30 stores a retest rule for determining whether or not to perform a retest based on the measurement result of the initial test. When it is determined to perform a retest according to the rule, the control unit 30 generates a measurement order of the retest.

At the time of the initial test, the plurality of specimen containers 100 housed in the specimen rack 110 from the leftmost housing portion 111 to the rightmost housing portion 111 are taken into the first measurement unit 10A or the second measurement unit 10B, in order, and the specimens are measured. At this time, the measurement unit into which the specimen container 100 is taken is determined so that a load of the measurement unit is dispersed. For example, specimen containers 100 with an odd number of housing position number shown in FIG. 4 are taken into the second measurement unit 10B, and specimen containers 100 having an even number of housing position number are taken into the first measurement unit 10A.

Transport Unit 20

As described above, the transport unit 20 includes a first transport path 21, a second transport path 22, and a third transport path 23. The three transport paths extend in the left-right direction and are arranged parallel to each other. The first transport path 21 transports the specimen rack 110 from the upstream side to the downstream side (right to left) of the specimen analysis system 1. The second transport path 22 is capable of transporting the specimen rack 110 to both right-to-left and left-to-right.

The third transport path 23 transports the QC specimen rack 160 from the downstream side to the upstream side (left to right) of the specimen analysis system 1. The QC specimen container 150 contains the quality control material used for multiple measurements, and the quality control material needs to be cooled and stored in the supply unit 80. Therefore, the QC specimen container 150 is returned to the supply unit 80 after finish of the measurement in the measurement unit. In the present embodiment or embodiments, since the used specimen rack 110 is transported to the collection unit 60, the third transport path 23 does not transport the specimen rack 110.

The transport unit 20 is provided with movable stoppers 21c and 23b at the downstream end of the first transport path 21 and the downstream end of the third transport path 23, respectively. A movable stopper 21d is provided between the first transport path 21 and the third transport path 23, at a position aligned with the second storage section 25 described later in the front-rear direction. Hereinafter, content common to the transport of the specimen rack 110 and the QC specimen rack 160 will be described by taking the specimen rack 110 as an example to explain the configuration of the transport unit 20.

The first transport path 21, the second transport path 22, and the third transport path 23 are arranged apart from each other in the front-rear direction. Between the first transport path 21 and the second transport path 22, the first storage section 24 and the second storage section 25, which are spaces capable of storing the specimen rack 110, are provided. The right end of the second transport path 22 is connected to the upstream end of the first transport path 21 via the first storage section 24, and the left end of the second transport path 22 is connected to the downstream end of the first transport path 21 via the second storage section 25.

The transport unit 20 further includes a plurality of rack delivery sections for transferring the specimen rack 110 between the transport paths and between the transport path and the storage section, and a plurality of sensors for detecting the position of the specimen rack 110 on the transport path and the storage section. The transport unit 20 includes an information reading section 26 that reads the specimen ID and the rack ID from the machine-readable label 103 of the specimen container 100 and the machine-readable label 112 of the specimen rack 110, respectively. The information reading section 26 is arranged at the center of the second transport path 22 in the length direction. The information reading section 26 is arranged so as to read the machine-readable labels 103 and 112 described above, between a right take-out position P2 corresponding to the first measurement unit 10A and a left take-out position P2 corresponding to the second measurement unit 10B.

The transport unit 20 includes a first delivery section 27A, a second delivery section 27B, a third delivery section 27C, and a fourth delivery section 27D as the rack delivery sections. Each of the four rack delivery sections is a rack transport device configured to be movable in the front-rear direction. The first delivery section 27A is configured to push out the specimen rack 110 from the upstream position of the first transport path 21 to the first storage section 24. The second delivery section 27B transports the specimen rack 110 from the first storage section 24 to the right end position of the second transport path 22. The third delivery section 27C transports the specimen rack 110 from the left end position of the second transport path 22 to the second storage section 25. The fourth delivery section 27D transports the specimen rack 110 from the second storage section 25 to the downstream position of the first transport path 21.

The transport unit 20 includes four sensors 28a, 28b, 28c, and 28d as sensors for detecting the specimen rack 110 on the first transport path 21 and the second transport path 22. The transport unit 20 also includes sensors 28e and 28f as sensors for detecting the specimen rack 110 on the third transport path 23. The transport unit 20 includes sensors 28g, 28h, and 28i as sensors for detecting the specimen rack 110 in the first storage section 24 and the second storage section 25.

Hereinafter, components of the transport unit 20 will be described along a transportation route of the specimen rack 110. In FIG. 5 and FIG. 6, the components of the transport unit 20 will be described by illustrating the module 10 arranged on the upstream side of the specimen analysis system 1, out of the two modules 10.

The first transport path 21 includes transport belts 21a and 21b for transporting the specimen rack 110 carried in from the supply unit 80 to the module 10 on the downstream side. The transport belts 21a and 21b are independently driven by the corresponding stepping motors, respectively. That is, the first transport path 21 includes two conveyor belts. The transport belt 21b is provided from the front position of the second storage section 25 to the downstream end of the first transport path 21. The transport belt 21a is provided from the upstream end of the first transport path 21 to the vicinity of the transport belt 21b.

The specimen rack 110 is transported in the first transport path 21 under control of the transport controller 70. Specifically, the transport controller 70 sends a control signal to the stepping motors connected to the transport belts 21a and 21b, and the motor is driven based on the control signal. Similarly, the specimen rack 110 in the other transport path and the rack delivery section is transported under control of the transport controller 70 or the control unit 30.

The specimen rack 110 carried from the supply unit 80 to the upstream position of the first transport path 21 is transported toward the downstream side by the transport belt 21a. The specimen rack 110 is detected by the sensor 28a and is sent to the first storage section 24 by the first delivery section 27A. The sensor 28a is, for example, an optical sensor having a light emitter and a light receiver, and the light emitter and the light receiver are arranged so as to sandwich the first transport path 21 from the front and rear. The sensor 28a detects the specimen rack 110 by blocking light emitted from the light emitter by the specimen rack 110 and lowering a light receiving level of the light receiver. The similar optical sensor as the sensor 28a can be applied to the other sensors installed in the transport unit 20.

The first delivery section 27A provided at the upstream position of the first transport path 21 has a plate 271 along the length direction of the first transport path 21 and a plate 272 along the width direction of the first transport path 21, as an engagement part that engages with the specimen rack 110. For example, the plates 271 and 272 are connected to each other and are arranged in a substantially L-shape in a plan view. The first delivery section 27A is configured to be movable in the front-rear direction between a retracted position (see FIG. 5) in which the plates 271, 272 do not interfere with the transport of the specimen rack 110 through the first transport path 21, a stop position (see FIG. 6) that stops the specimen rack 110 transported through the first transport path 21, and a position where the specimen rack 110 is pushed out to the first storage section 24.

In a state where the first delivery section 27A is in the stop position, only the plate 272 is arranged on the first transport path 21 as shown in FIG. 6. The specimen rack 110 transported by the transport belt 21a is caught by the plate 272 and stopped. By moving the first delivery section 27A (plate 271) backward from this state, the specimen rack 110 is pushed out to the first storage section 24. The specimen rack 110 transported to the first storage section 24 is detected by the sensors 28g arranged so as to sandwich the first storage section 24 from the left and right.

The first storage section 24 is a space for storing the specimen rack 110 received from the first transport path 21. For example, the first storage section 24 is constituted by arranging plate members whose upper surfaces are parallel to the horizontal plane between the first transport path 21 and the second transport path 22. The specimen rack 110 sent out to the first storage section 24 is detected by the sensor 28g and is sent out to the second transport path 22 by the second delivery section 27B at an appropriate timing. The second delivery section 27B has, for example, an engagement part that abuts on the front surface of the specimen rack 110. The second delivery section 27B pushes the left and right ends of the front surface of the specimen rack 110 backward to push out the specimen rack 110 to the right end position of the second transport path 22. The sensor 28c is installed near the right end position of the second transport path 22, and the specimen rack 110 transported to the right end position is detected by the sensor 28c.

The second transport path 22 includes two transport belts 22a and 22b that independently transport the specimen rack 110 in the left-right direction. The transport belts 22a and 22b are independently driven by stepping motors provided corresponding to each belt. The transport belts 22a and 22b are arranged side by side in the front-rear direction. The transport belts 22a and 22b extend in the left-right direction from the right end position to the left end position of the second transport path 22. The transport belt 22a is provided with two protrusions 22c into which the specimen rack 110 fits. Similarly, the transport belt 22b is provided with two protrusions 22d into which the specimen rack 110 fits. The specimen rack 110 is sent out to the second delivery section 27B so as to fit between these protrusions 22c and 22d. The specimen rack 110 is transported to the left and right by driving the transport belts 22a and 22b while being fitted between the protrusions 22c.

According to the second transport path 22, the two specimen racks 110 can be separately transported in the left-right direction. As shown in FIG. 6, two specimen racks 110 can be carried into the second transport path 22 at the same time. Hereinafter, a specimen rack 110 sent to the second transport path 22 first is referred to as a "leading rack", and a specimen rack 110 sent to the second transport path 22 after the leading rack is referred to as a "trailing rack". In this case, it is possible to measure the specimen on the leading rack and measure the trailing rack in parallel.

The information reading section 26 includes rollers 26a and 26b arranged so as to sandwich the second transport path 22, and a reading portion 26c. The rollers 26a and 26b can move in directions close to each other, and the roller 26a rotates with the specimen container 100 sandwiched in the front-rear direction. As a result, the specimen container 100 rotates. The reading portion 26c reads the machine-readable label 103 of the rotating specimen container 100 from a gap between the rollers 26b. The reading portion 26c can also read the rack ID of the specimen rack 110. The reading portion 26c is, for example, a barcode reader. The specimen ID and rack ID are read by the information reading section 26, and the specimen is measured in the measurement unit under control of the control unit 30.

The specimen container 100 whose specimen ID has been read is transported to the take-out position P2 corresponding to either the first measurement unit 10A or the second measurement unit 10B, is taken out from the specimen rack 110 by the robot hand 15, and is taken into the measurement unit. At this time, the measurement unit into which the specimen container 100 is taken is determined so that the load of each measurement unit is dispersed. The initial test is performed in the measurement unit, and when the initial test is finished, the specimen container 100 is returned to the original housing portion 111 at the take-out position P2. When the initial test and necessary retest for all the specimen containers 100 housed in the specimen rack 110 are all finished, the specimen rack 110 is transported to the downstream end of the second transport path, that is, to the rear of the second storage section 25, and the specimen rack 110 is transported to the second storage section 25 by the third delivery section 27C.

Even when the initial test is finished for all the specimen containers 100 in the leading rack, the leading rack needs to stay on the second transport path 22 until necessity of retest is determined for all the specimen containers 100. At this time, since it takes a predetermined time to determine the necessity of reinspecting the specimen container 100 in which the initial test was finally performed. Therefore, in order to improve measurement efficiency, the trailing rack is sent to the second transport path 22, and the initial test of the trailing rack is started. The leading rack in standby is retracted to the left end position of the second transport path 22 so as not to interfere with the transport of the trailing rack.

The sensor 28d is installed near the left end position of the second transport path 22. The specimen rack 110 in which the initial test and necessary retest are all finished is pushed out by the third delivery section 27C from the left end position to the second storage section 25 provided in front of the third delivery section 27C. The second storage section 25 is a space for storing the specimen rack 110 received from the second transport path 22. The second storage section 25 is constituted by arranging plate members whose upper surfaces are parallel to the horizontal plane, like the first storage section 24. The specimen rack 110 in the second storage section 25 is detected by the sensors 28h and 28i and is pushed out to the first transport path 21 by the fourth delivery section 27D at an appropriate timing.

The rack in the second storage section is transported to the first transport path 21 or the third transport path, according to the next transport destination determined by the transport controller 70.

For example, when the rack in the second storage section is the specimen rack 110 housing the specimen container 100 and the next transport destination is the process unit 40 or the collection unit 60, the specimen rack 110 needs to be transported to the left direction. Therefore, the specimen rack 110 is sent to the first transport path 21. For example, when the rack in the second storage section is the QC specimen rack 160 housing the QC specimen container 150 and the next transport destination is the adjacent measurement block, the QC specimen rack 160 needs to be transported to the left direction. Therefore, the QC specimen rack 160 is sent to the first transport path 21. When the next transport destination is the supply unit 80, the QC specimen rack needs to be transported to the right direction. Therefore, the QC specimen rack is sent to the third transport path.

When the rack in the second storage section 25 is transported to the first transport path 21, the fourth delivery section 27D pushes the rack forward with the stopper 21d raised to a position higher than the belt of the first transport path 21. The rack pushed forward stops at the downstream position of the first transport path 21 by hitting the stopper 21d. When the transport belt 21b is driven with the stopper 21c lowered, the rack is transported to the left direction.

When the rack in the second storage section 25 is transported to the third transport path 23, the fourth delivery section 27D pushes the rack forward with the stopper 21d lowered to a position equal to or lower than the belt height of the first transport path 21. The rack pushed forward passes over the stopper 21d and is sent to the upstream position of the third transport path 23.

The third transport path 23 includes a transport belt 23a. The transport belt 23a is driven by a stepping motor, like the transport belts 21a and 21 b described above. The rack transported to the third transport path 23 is transported to the right direction by the transport belt 23a.

Supply Unit 80

Hereinafter, a configuration of the supply unit 80 will be described in detail with reference to FIGS. 7, 8, 9, 10, 11, 12, 13, 14, 15, 16, 17, 18, 19, 20, 21, 22, 23, 24, 25, 26, 27, 28, 28 and 29.

As described above, the supply unit 80 is a device for supplying the specimen rack 110 housing the specimen container 100 to the measurement unit. The supply unit 80 further cools and stores the QC specimen container 150 containing a quality control material. The supply unit 80 adjusts the temperature of the quality control material to the measurement temperature according to a schedule previously registered by a user. Thereafter, the QC specimen container 150 containing the temperature-controlled quality control material is set in the rack and transported toward the target measurement unit.

The QC specimen container 150 is housed in the empty rack 170. The QC specimen container 150 is transported to the second transport path 22 of the transport unit 20 as the QC specimen rack 160 in which the QC specimen container 150 is housed, like the specimen rack 110.

The QC specimen container 150 differs from the specimen container 100 in housing a quality control material containing a cell with a known concentration. The QC specimen container 150 includes a tube 101 and a cap 102, like the specimen container 100. A machine-readable label 103 indicating a specimen ID including lot number, concentration level, and expiration date of the QC specimen is attached to the side surface of the tube 101. The machine-readable label 103 is a barcode label. The QC specimen container 150 may use a container with a shape different from that of the specimen container 100. The specimen container 100 and the QC specimen container 150 may use two or more types of containers, respectively.

The quality control material is also generally referred to as a control sample or a QC specimen. In the specimen analysis system 1, it is necessary to periodically confirm that there is no abnormality in the measurement result of the analyzer using a quality control material and manage measurement accuracy. For example, before starting the measurement of specimen once a day, the specimen analysis system 1 transports the QC specimen container 150 to the first measurement unit 10A and the second measurement unit 10B which are analyzers, and measures the quality control material. The measured values of the quality control material, for example, values of red blood cell count, white blood cell count, platelet count, hemoglobin concentration, and the like, are compared with, for example, the upper limit value and the lower limit value stored in advance in the control section 31 of the control unit 30. When the measured value of the quality control material is within the range of the upper limit and the lower limit, the quality control result is determined to be normal. When the measured value of the quality control material is out of the range, the quality control result is determined to be abnormal.

The quality control material is control blood preferably used for quality control of an automatic blood cell counter. The quality control material contains a whole blood component adjusted to a known concentration. The whole blood component is, for example, a blood cell, which includes a red blood cell, a white blood cell, and a platelet. As such a quality control material, there is XN-CHECK (manufactured by Sysmex Corporation). The quality control material may include three types of quality control materials adjusted to three concentration levels of low concentration, standard concentration, and high concentration. In the following, low-concentration quality control materials are referred to as level 1, standard-concentration quality control materials are referred to as level 2, and high-concentration quality control materials are referred to as level 3.

In the supply unit 80, for example, a plurality of QC specimen containers 150 are cooled and stored. The supply unit 80 is preferably cooled and stored in two or more types of containers each containing a plurality of types of quality control materials with different concentration levels.

Figure 7:
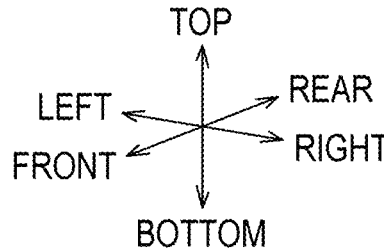
FIG. 7 is a perspective view of a supply unit constituting a specimen analysis system.

FIG. 7 is a perspective view showing an appearance of the supply unit 80. The supply unit 80 includes a first transport path 811 (see FIG. 8 illustrated later) of the conveyor section 81 accessible from outside by the user to set the rack. On the front surface of the supply unit 80, a first charging port 831A in which the QC specimen container 150 is set and a first cover 832A that covers the first charging port 831A are provided.

The first cover 832A covers the entire first charging port 831A. The first cover 832A is opened and closed by the user. The first cover 832A is configured such that, for example, the left end portion is rotatably supported with respect to a housing and rotates to the left to open. When the first cover 832A is opened, a transfer holder 834 (see FIG. 8 and the like) that holds the QC specimen container 150 and transfers the QC specimen container 150 to the inside of the supply unit 80 is exposed. As will be described in detail later, the QC specimen container 150 is set in the transfer holder 834.

The supply unit 80 further includes a second charging port 831B in which a cleaning agent container 180 (see FIG. 8 and the like) is set, and a second cover 832B that covers the second charging port 831B. The second charging port 831B is arranged adjacent to the right side of the first charging port 831A. The second cover 832B is configured such that, for example, the rear end portion is rotatably supported with respect to the housing and rotates upward to open.

A monitor 91 is provided on the front surface of the supply unit 80. The monitor 91 is, for example, a display device for displaying information on the state of the supply unit 80 including information on the charged QC specimen container 150, information necessary for operating the supply unit 80, and the like. The monitor 91 is composed of a touch panel that can also be used as an operation section.

Figure 8:
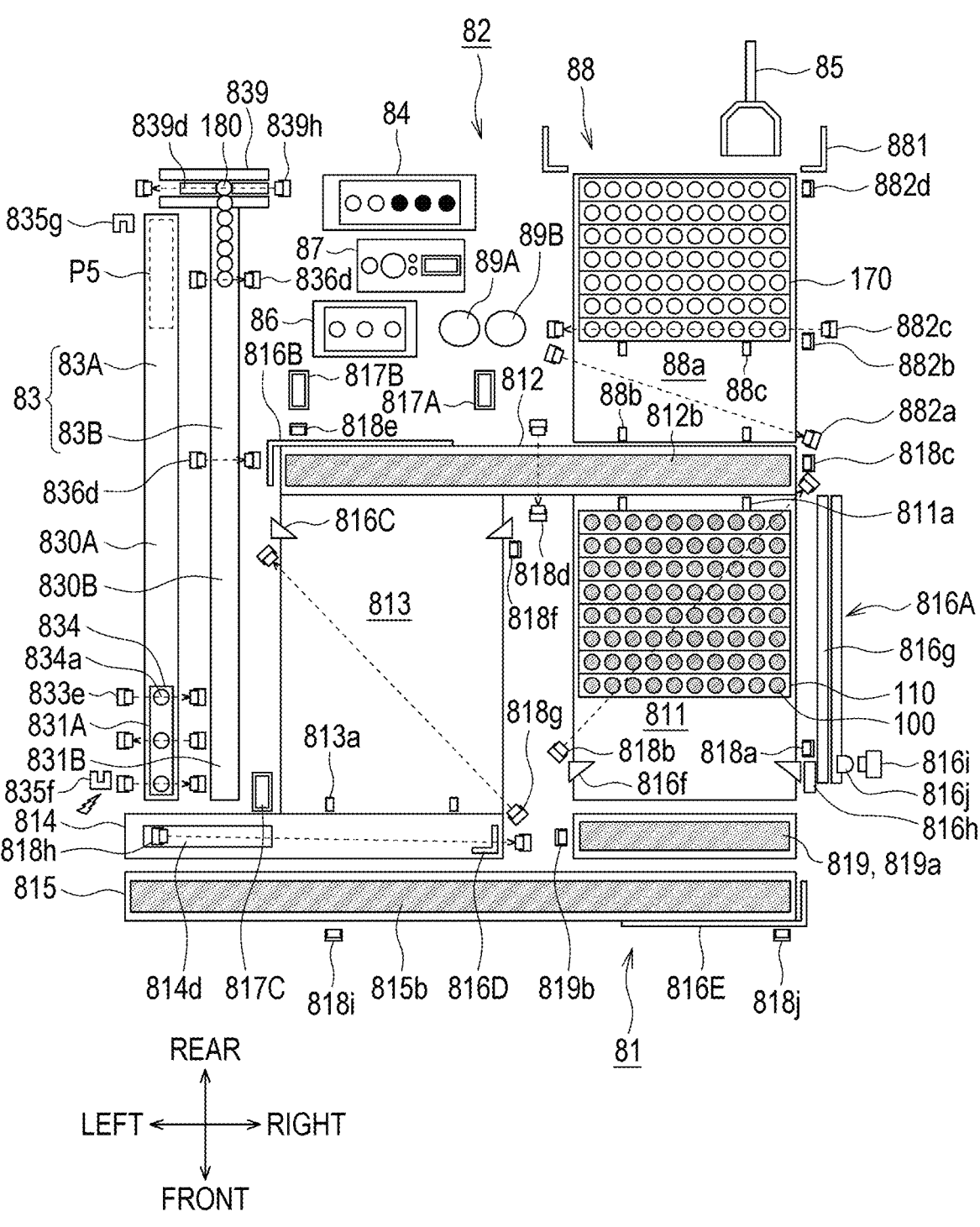
FIG. 8 is a diagram schematically showing a configuration (e.g., internal layout) of a supply unit, showing a state in which a specimen rack is set on a conveyor section.

FIG. 8 is a diagram schematically showing the internal layout of the supply unit 80. The supply unit 80 includes the conveyor section 81 and the storage adjustment unit 82 as main components. The storage adjustment unit 82 includes a charging section 83, a cold insulation section 84, a transfer section 85, a heating section 86, an information reading section 87, and a rack housing section 88. In the following description, content common to the transport of the specimen rack 110 and the transport of the QC specimen rack 160 will be described by taking the transport of the specimen rack 110 as an example.

Conveyor Section 81

The conveyor section 81 includes a plurality of rack transport paths for transporting the specimen rack 110 in the supply unit 80. The conveyor section 81 includes the first transport path 811, a second transport path 812, a third transport path 813, and a fourth transport path 814 in this order from the upstream side. These four transport paths are connected, and the specimen rack 110 set in the first transport path 811 is sent to the fourth transport path 814 via the second transport path 812 and the third transport path 813. The fourth transport path 814 is connected to the transport unit 20 of the module 10, and the specimen rack 110 is transported from the fourth transport path 814 to the first transport path 21 of the transport unit 20.

The conveyor section 81 further includes a fifth transport path 815 connected to the third transport path 23 of the transport unit 20, for receiving the QC specimen rack 160 that has returned via the third transport paths 23 of the adjacent transport units 20. The fifth transport path 815 is arranged in the front of the conveyor section 81 with respect to the fourth transport path 814. The fifth transport path 815 is a rack transport path for returning the QC specimen rack 160 to the storage adjustment unit 82, which is connected to the first transport path 811.

Figure 49:
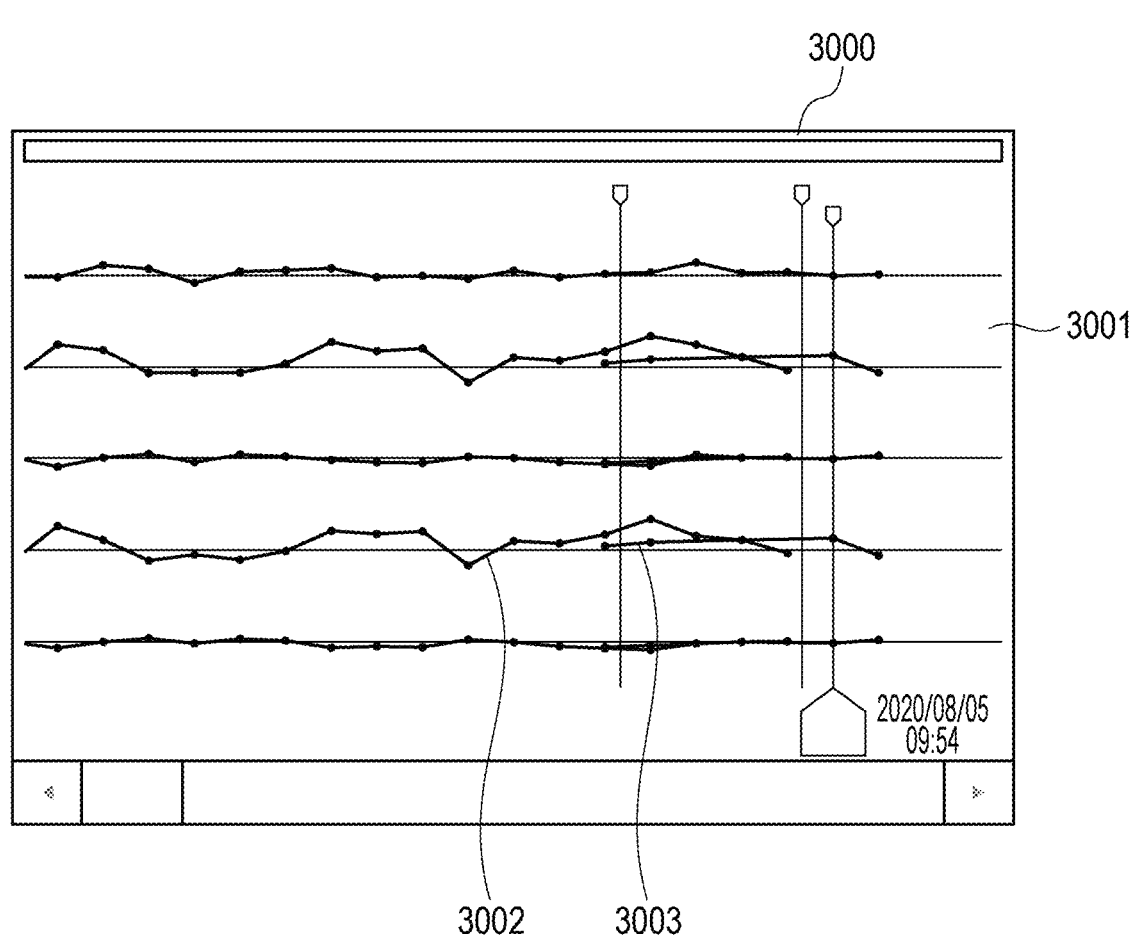
FIG. 49 is an example of a screen for comparing quality control results of old lot and new lot displayed on a monitor of a specimen analysis system.

The conveyor section 81 is provided with a sixth transport path 819 between the first transport path 811 and the fifth transport path 815. When an additional supply unit is provided, as shown in FIG. 49 illustrated later, the sixth transport path 819 is used when the specimen rack 110 is carried in from the additional supply unit. The sixth transport path 819 includes a transport belt 819a that transports the specimen rack 110 from right to left. A sensor 819b for detecting the specimen rack 110 is installed near the left end position of the sixth transport path 819.

The first transport path 811 and the third transport path 813 are arranged parallel to each other. The first transport path 811 is a transport path for transporting the specimen rack 110 from the front to the rear. The third transport path 813 is a transport path for transporting the specimen rack 110 from the rear to the front. The second transport path 812 is provided extending in the left-right direction. The right end of the second transport path 812 is aligned with the rear end of the first transport path 811. The left end of the second transport path 812 is aligned with the rear end of the third transport path 813. With such a configuration, the second transport path 812 can receive the rack sent out from the first transport path 811, and the second transport path 812 can transport the rack in the left-right direction. The third transport path 813 can receive the rack transported to the left end by the second transport path 812.

The first transport path 811 and the third transport path 813 are formed long in the front-rear direction. The first transport path 811 and the third transport path 813 can store a plurality of specimen racks 110 at a time. The first transport path 811 is provided with a stopper 811a for supplying the specimen rack 110 to the second transport path 812 one by one. The stopper 811a is a movable stopper that moves in the vertical direction. The stopper 811a is arranged at a boundary between the first transport path 811 and the second transport path 812.

The stopper 811a is provided so as to be rotatable in the front-rear direction. When the stopper 811a is rotated from the rear to the front, the stopper 811a is in a state of protruding upward, and when the stopper 811a is rotated in the opposite direction, the stopper 811a is contained downward. When the specimen rack 110 on the first transport path 811 is transported to the second transport path 812, the stopper 811a is put in a state of not protruding from the upper surface. When the transport of the rack to the second transport path 812 is completed, the stopper 811a rotates forward, and the stopper 811a is positioned so as to intervene between the specimen rack 110 on the second transport path 812 and the specimen rack 110 on the first transport path 811. The two racks are separated by inserting the stopper 811a between the specimen racks 110. The third transport path 813 is also provided with a movable stopper 813a similar to the stopper 811a at a boundary between the third transport path 813 and the fourth transport path 814.

The second transport path 812, the fourth transport path 814, and the fifth transport path 815 extend in the left-right direction and are arranged parallel to each other. The second transport path 812 is provided with a transport belt 812b capable of transporting the specimen rack 110 to both right-to-left and left-to-right. The fourth transport path 814 is a transport path for transporting the specimen rack 110 to the first transport path 21 of the transport unit 20, and the third transport path 813 is connected to the right end side of the fourth transport path 814. The fifth transport path 815 includes a transport belt 815*b* capable of transporting the QC specimen rack 160 carried in from the third transport path 23 of the transport unit 20 in the right direction.

The conveyor section 81 includes a plurality of rack delivery sections for transferring the specimen rack 110 between the transport paths, and a plurality of sensors for detecting the position of the specimen rack 110 on the transport path. Further, the conveyor section 81 includes a first information reading section 817A, a second information reading section 817B, and a third information reading section 817C.

The conveyor section 81 includes a first delivery section 816A, a second delivery section 816B, a third delivery section 816C, a fourth delivery section 816D, and a fifth delivery section 816E as the rack delivery sections. The first delivery section 816A includes an engagement part 816*f* that abuts on the front surface of the specimen rack 110 and pushes the specimen rack 110 backward, and driving mechanisms that move the engagement part 816*f* in the front-rear direction along the first transport path 811. The first delivery section 816A is configured to push out the specimen rack 110 from the first transport path 811 to the second transport path 812.

The first delivery section 816A includes a belt 816*g* arranged along the first transport path 811, a connecting member 816*h* connecting the engagement part 816*f* and the belt 816*g*, and a motor 816*i* driving the belt 816*g*, as the driving mechanisms. For the motor 816*i*, for example, a stepping motor is used. In the first transport path 811, the specimen rack 110 pushed by the engagement part 816*f* hits the preceding rear specimen rack 110 and stops. Therefore, the first delivery section 816A is provided with a torque sensor 816*j* capable of detecting this state.

The first delivery section 816A is configured to return the engagement part 816*f* to the origin position shown in FIG. 8 when the torque sensor 816*j* operates. For example, when the engagement part 816*f* is returned to the origin position, the engagement part 816*f* is rotatably supported rearward with respect to the connecting member 816*h* so that the specimen rack 110 is not pushed forward even when the engagement part 816*f* hits the subsequent specimen rack 110. The third delivery section 816C has the similar structure as the first delivery section 816A. The third delivery section 816C is configured to push the specimen rack 110 from the third transport path 813 to the fourth transport path 814.

The second delivery section 816B transports the specimen rack 110 from the second transport path 812 to the third transport path 813. The fourth delivery section 816D transports the specimen rack 110 from the fourth transport path 814 to the first transport path 21 of the transport unit 20. The fifth delivery section 816E transports the QC specimen rack 160 from the fifth transport path 815 to the first transport path 811.

The conveyor section 81 includes sensors 818*a* and 818*b* as sensors for detecting the specimen rack 110 on the first transport path 811. The conveyor section 81 includes sensors 818*c* and 818*e* as sensors for detecting the specimen rack 110 on the second transport path 812. The conveyor section 81 includes sensors 818*f* and 818*g* as sensors for detecting the specimen rack 110 on the third transport path 813. The conveyor section 81 includes a sensor 818*h* as a sensor for detecting the specimen rack 110 on the fourth transport path 814. The conveyor section 81 includes sensors 818*i* and 818*j* as sensors for detecting the specimen rack 110 on the fifth transport path 815.

The conveyor section 81 further includes a sensor 818*d* for detecting a container housed in a rack moving on the second transport path 812. The sensor 818*d* is provided in the middle portion of the second transport path 812. The presence or absence of a container in the rack moving on the second transport path 812 can be known from detection information of the sensor 818*d*. Therefore, when the container is not detected by the sensor 818*d*, it can be determined that the rack on the second transport path 812 is an empty rack 170. The detection information of the sensor 818*d* is used to determine the transport destination of the rack moving on the second transport path 812.

For the sensors 818*a*, 818*c*, 818*e*, 818*f*, 818*i* and 818*j*, for example, a reflective optical sensor in which a light emitter and a light receiver are integrated is used. For the sensors 818*b*, 818*d*, 818*g* and 818*h*, a photointerrupter optical sensor in which a light emitter and a light receiver are separated is used. An opening 814*d* with a size that does not interfere with the transportation of the specimen rack 110 is formed in the fourth transport path 814. A light emitter of the sensor 818*h* is arranged under the opening 814*d*, and a light receiver is arranged near the right end position of the fourth transport path 814.

When the specimen rack 110 is set in the first transport path 811, the specimen rack 110 is detected by the sensor 818*b*, and the specimen rack 110 is transported to the right end position of the second transport path 812 by the first delivery section 816A. The specimen rack 110 carried into the right end position of the second transport path 812 is detected by the sensor 818*c*. The specimen rack 110 is transported to the left end position of the second transport path 812 by the transport belt 812*b*. In the specimen rack 110 that moves from right to left on the second transport path 812, the presence or absence of a container housed in the rack is detected by the sensor 818*d* arranged in the middle portion of the second transport path 812.

At the left end position of the second transport path 812, the specimen rack 110 is detected by the sensor 818*e*. The first information reading section 817A and the second information reading section 817B are provided behind the second transport path 812. The first information reading section 817A and the second information reading section 817B are provided movably in directions close to each other. The first information reading section 817A and the second information reading section 817B read the specimen ID of the specimen container 100 housed in the specimen rack 110 in order. The first information reading section 817A and the second information reading section 817B have, for example, the similar structure as the information reading section 87, and two rollers are arranged so as to sandwich the second transport path 812. In FIG. 8, the rollers are omitted for simplification of the illustration.

The first information reading section 817A reads specimen IDs of specimen containers 100 with housing position numbers 6 to 10 shown in FIG. 4, and the second information reading section 817B reads specimen IDs of specimen containers 100 with housing position numbers 1 to 5, respectively. The first information reading section 817A further reads the rack ID from the machine-readable label 112 of the specimen rack 110.

The third information reading section 817C has, for example, a reading section that is a barcode reader, and reads the rack ID. The third information reading section 817C is arranged behind the fourth transport path 814.

The specimen rack 110 transported from the second transport path 812 to the third transport path 813 by the second delivery section 816B is detected by the sensors 818*f* and 818*g*, and is transported to the fourth transport path 814 by the third delivery section 816C. The specimen rack 110 carried into the fourth transport path 814 is detected by the sensor 818*h*, and is transported to the first transport path 21 of the transport unit 20 by the fourth delivery section 816D. As described above, the specimen rack 110 transported to the transport unit 20 is collected by the collection unit 60 arranged on the downstream side of the specimen analysis system 1. Therefore, the specimen rack 110 transported to the transport unit 20 does not return to the supply unit 80.

The QC specimen rack 160 in which the QC specimen container 150 is housed is supplied from the rack housing section 88 to the right end position of the second transport path 812. Thereafter, the QC specimen rack 160 is transported to the first transport path 21 of the transport unit 20, via the second transport path 812, the third transport path 813, and the fourth transport path 814, like the specimen rack 110 The QC specimen rack 160 is collected from the third transport path 23 of the transport unit 20 to the fifth transport path 815. The QC specimen rack 160 carried into the fifth transport path 815 is detected by the sensor 818*i*, and is transported to the right end position of the fifth transport path 815 by the transport belt 815*b*. The QC specimen rack 160 is detected by the sensor 818*j* at the right end position of the fifth transport path 815, and is transported to the first transport path 811 by the fifth delivery section 816E.

Charging Section 83

As shown in FIG. 8, the charging section 83 includes a first charging section 83A for transferring the QC specimen container 150 from the first charging port 831A to the take-out position P5, and a second charging section 83B for transferring a cleaning agent container 180 from the second charging port 831B to a take-out section 839. The take-out position P5 is a position where the QC specimen container 150 accessible by the transfer section 85 is taken out, and the rear end of the first charging section 83A is the take-out position P5. The take-out section 839 includes a transfer plate 839*d*, a sensor 839*h*, and the like. The take-out section 839 is provided at the rear end of the second charging section 83B.

The first charging section 83A includes a transfer path 830A for the QC specimen container 150 extending in the front-rear direction. Similarly, the second charging section 83B includes a transfer path 830B for the cleaning agent container 180 along the front-rear direction. In the present embodiment or embodiments, the transfer paths 830A and 830B are formed parallel to each other. Sensors 835*f* and 835*g* for detecting the transfer holder 834 are provided in the vicinity of the first charging port 831A and the vicinity of the take-out position P5, respectively. For the sensors 835*f* and 835*g*, for example, proximity sensors such as magnetic sensors and eddy current sensors are used.

In the first charging section 83A, a plurality of sensors 833*e* are installed in the first charging port 831A. In the second charging section 83B, a plurality of sensors 836*d* are installed along the transfer path 830B. The transfer path 830B of the second charging section 83B is a passage for transferring the cleaning agent container 180. The transfer path 830B also functions as a storage section for storing a plurality of cleaning agent containers 180. Therefore, the plurality of sensors 836*d* for detecting the cleaning agent container 180 present in the transfer path 830B are installed along the transfer path 830B. The number of cleaning agent containers 180 stored in the transfer path 830B can be confirmed from detection information of the plurality of sensors 836*d*.

Figure 9:
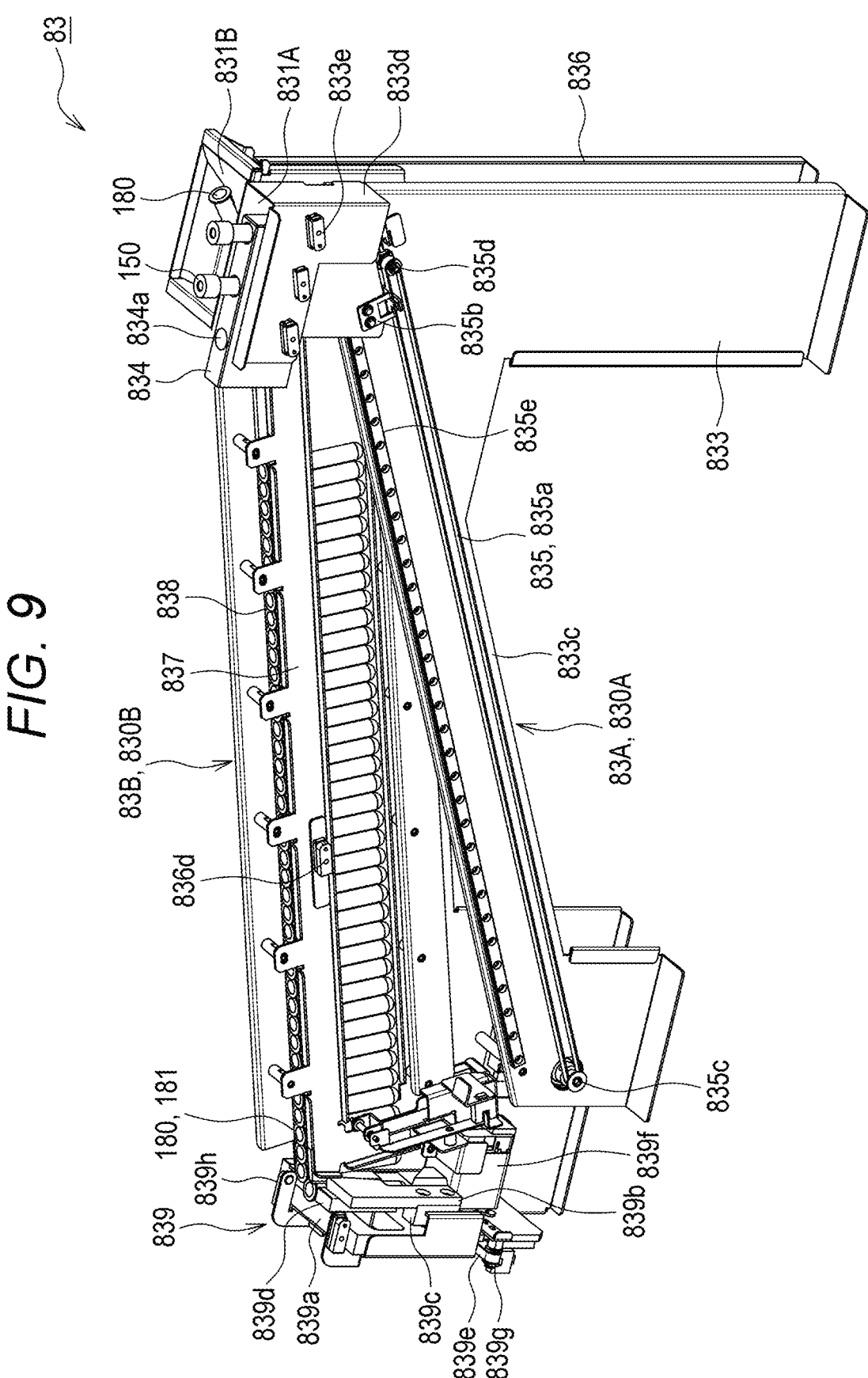
FIG. 9 is a perspective view of a charging section constituting a supply unit, showing a state in which QC specimen containers are set in a charging port.
Figure 10:
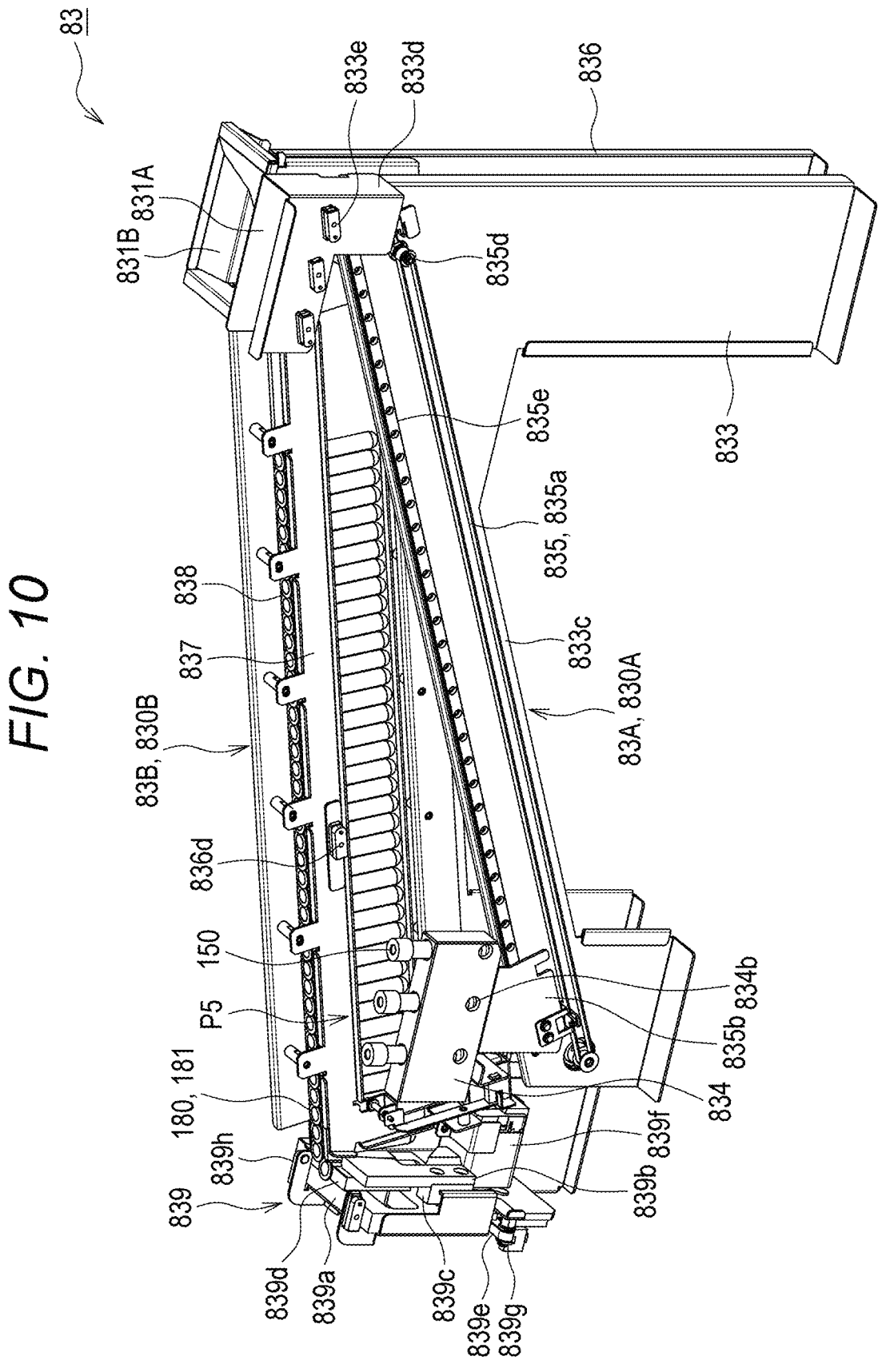
FIG. 10 is a perspective view of a charging section, showing a state in which a QC specimen containers are transported to an inside of a storage adjustment unit.

FIGS. 9 and 10 are perspective views of the charging section 83. FIG. 9 shows a state in which the transfer holder 834 is located at the first charging section 83A, and FIG. 10 shows a state in which the transfer holder 834 is located at the take-out position P5. As shown in FIGS. 9 and 10, the charging section 83 is a device in which the first charging section 83A and the second charging section 83B are integrated. The charging section 83 includes frames 833 and 836 that shape the transfer paths 830A and 830B inclined from the front to the rear.

The first charging section 83A includes a transfer holder 834 and a driving mechanism 835 that moves the transfer holder 834 in the front-rear direction. The transfer holder 834 is provided with a plurality of housing portions 834*a* capable of storing the QC specimen container 150 one by one. The transfer holder 834 is formed in a block shape as a whole. The plurality of housing portions 834*a*, which are holes into which the QC specimen container 150 can be inserted, are formed on the upper surface of the transfer holder 834. The housing portion 834*a* is preferably formed so that the upper portion of a tube 101 gripped by arms 85*b* of the transfer section 85 protrudes from the upper surface of the transfer holder 834 with the QC specimen container 150 inserted.

Through holes 834*b* communicating with the housing portion 834*a* are formed on the side surface of the transfer holder 834. The through holes 834*b* are formed on both side surfaces of the transfer holder 834 side by side in the left-right direction. In the present embodiment or embodiments, there are three housing portions 834*a* arranged in a row in the front-rear direction, and one on each side for each housing portion 834*a*, a total of six through holes 834*b* are formed. The light emitter and the light receiver constituting the sensor 833*e* are installed on both side surfaces of a frame body 833*d* so that light passes through the housing portion 834*a* through the through hole 834*b*. As a result, the presence or absence of the QC specimen container 150 in each housing portion 834*a* can be detected in the first charging port 831A.

The driving mechanism 835 includes an endless belt 835*a* extending along an inclined portion 833*c*, a connecting member 835*b* connecting the transfer holder 834 and the belt 835*a*, a motor 835*c* including a rotating shaft on which the belt 835*a* is suspended, a pulley 835*d* on which the belt 835*a* is suspended, and a rail 835*e* guiding a movement of the transfer holder 834. The transfer holder 834 is movably attached to the frame 833 via the driving mechanism 835.

The transfer holder 834 is configured to automatically move from the first charging port 831A to the take-out position P5 when the QC specimen container 150 is housed in at least one housing portion 834*a* and the first cover 832A is closed. When the transfer holder 834 arrives at the take-out position P5, the QC specimen container 150 is taken out from the housing portion 834*a* by the transfer section 85, and the QC specimen container 150 is transferred to the information reading section 87. When all the QC specimen containers 150 are taken out from the transfer holder 834, the transfer holder 834 automatically moves, for example, to the first charging port 831A.

As described above, the first cover 832A that covers the first charging port 831A is locked so as not to open when the transfer holder 834 is not present at the position shown in FIG. 9 (also referred to as the origin position). When the transfer holder 834 arrives at the first charging port 831A and the transfer holder 834 is detected by the sensor 835f, the first cover 832A is unlocked.

The second charging section 83B includes a facing plate 837 attached with a gap from the frame 836, so that the gap can hold the cleaning agent container 180. A rail 838 is provided between the frame 836 and the facing plate 837 to support a flange 181 of the cleaning agent container 180 in a state where the cleaning agent container 180 is slidable. The cleaning agent container 180 slides in the transfer path 830B in a state where the flange 181 is supported and suspended by the rail 838. The cleaning agent container 180 is also stored in the transfer path 830B.

The take-out section 839 includes a transfer plate 839d that moves in the left-right direction while holding the cleaning agent container 180. The take-out section 839 is configured so that the cleaning agent container 180 is projected upward when the transfer plate 839d moves to the left end side of the take-out section 839. The take-out section 839 includes two support plates 839a and 839b that movably hold the transfer plate 839d, an inclined block 839c fixed to the lower part of the support plates 839a and 839b, and driving mechanisms for the transfer plate 839d. The take-out section 839 is provided with a belt 839e, a motor 839f, a pulley 839g, and the like, as the driving mechanisms.

The transfer plate 839d is formed with a holding portion capable of housing the cleaning agent container 180 in the center of the plate. When the transfer plate 839d moves to the left direction while holding the cleaning agent container 180, the lower end of the cleaning agent container 180 abuts on the upper surface of the inclined block 839c. The upper surface of the inclined block 839c is inclined so as to be higher toward the left side. Therefore, the cleaning agent container 180 is pushed up along the upper surface of the inclined block 839c so that the cleaning agent container 180 can be gripped by the transfer section 85.

The take-out section 839 is provided with a sensor 839h for detecting upward protrusion of the cleaning agent container 180. The light emitter and the light receiver constituting the sensor 839h are attached to the support plate 839a. The light emitter and the light receiver are arranged so that an optical axis along the left-right direction is formed on the transfer plate 839d. When the upward protrusion of the cleaning agent container 180 is detected by the sensor 839h, the cleaning agent container 180 is transferred from the take-out section 839 to the empty rack 170 of the rack housing section 88 by the transfer section 85.

Cold Insulation Section 84

Figure 11:
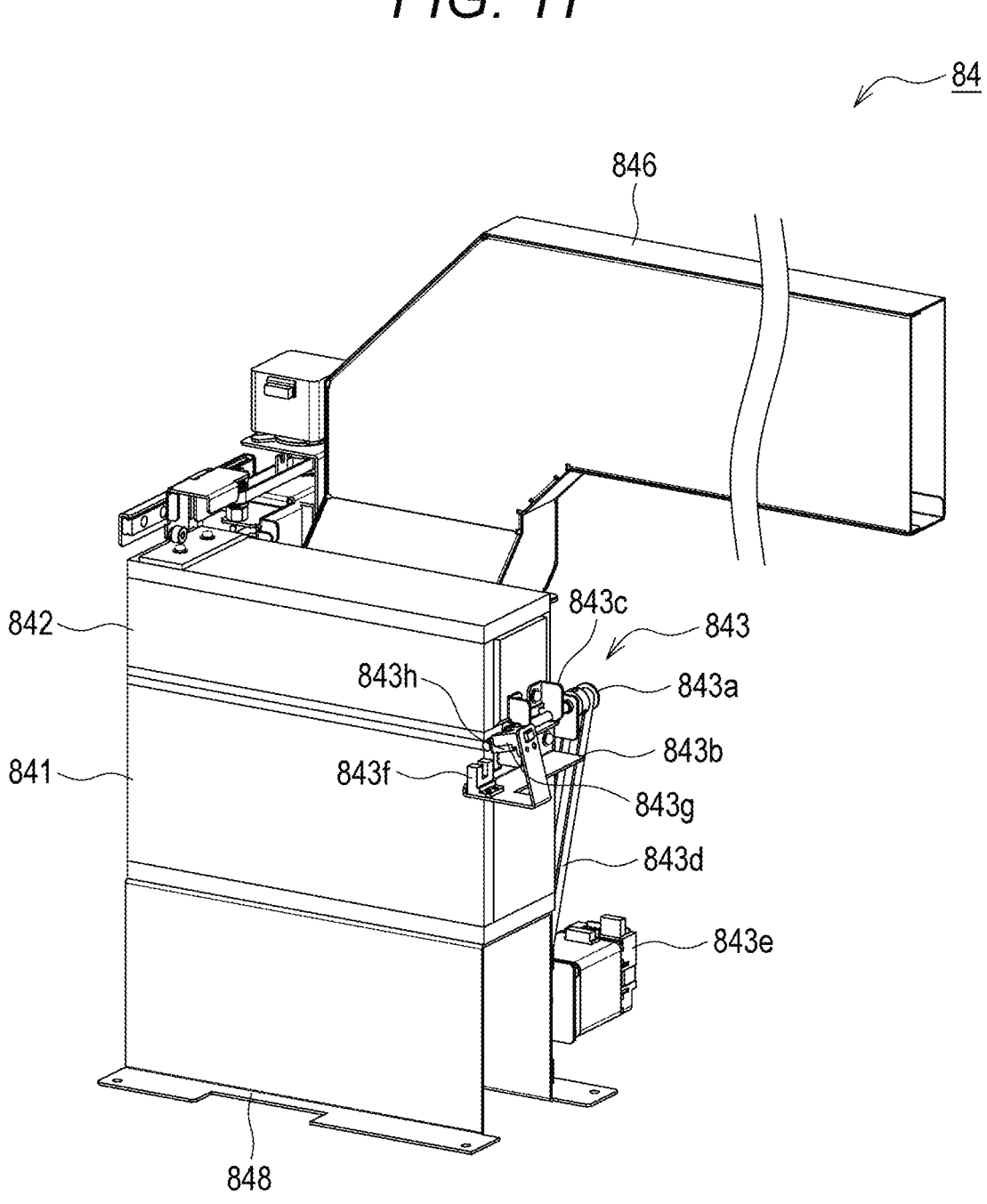
FIG. 11 is a perspective view of a cold insulation section constituting a supply unit, showing a state where a cover is closed.
Figure 12:
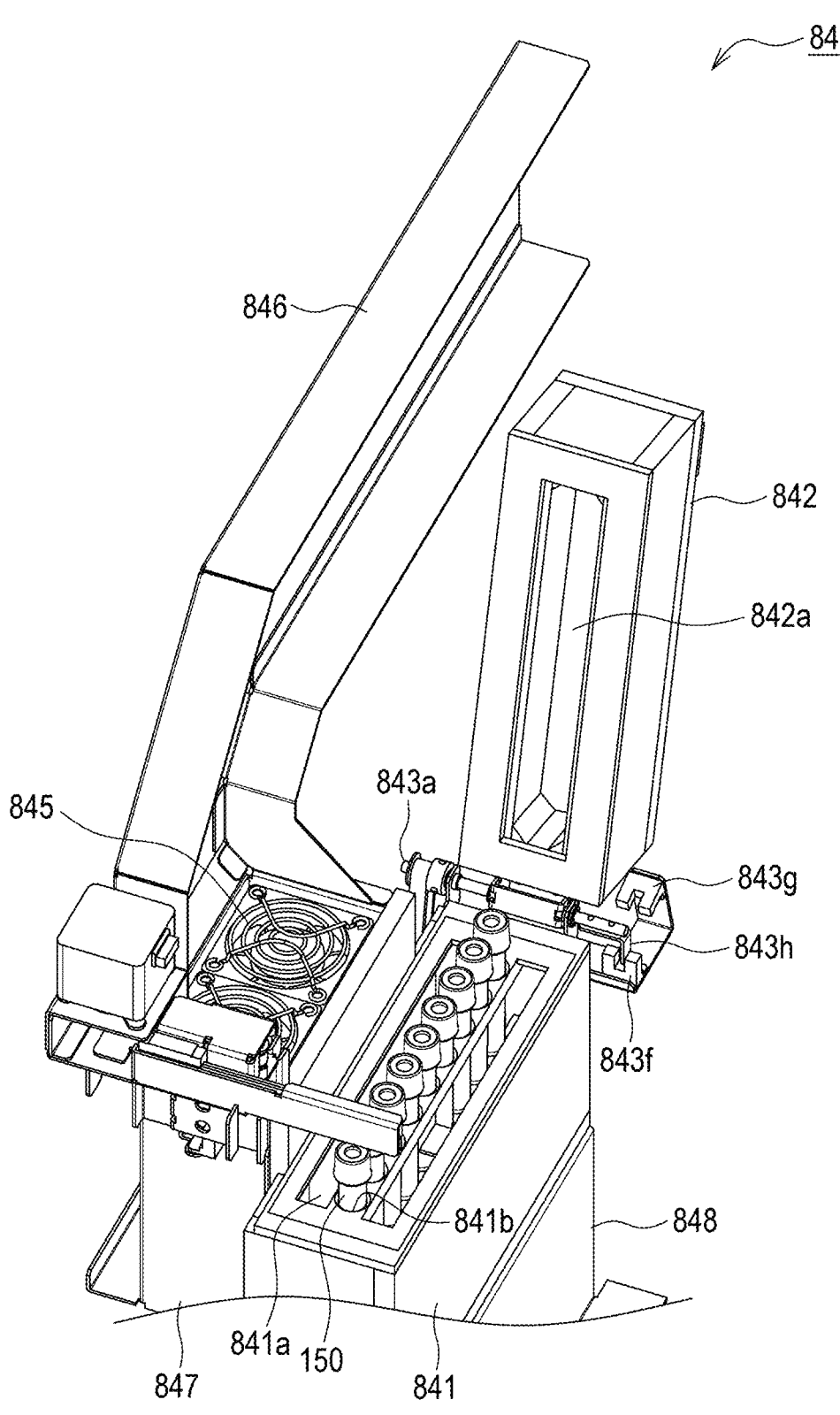
FIG. 12 is a perspective view of a cold insulation section, showing a state where a cover is opened.

FIGS. 11 and 12 are perspective views of the cold insulation section 84. FIG. 11 shows a state where a cover 842 of the cold insulation section 84 is closed. FIG. 12 shows a state in which the cover 842 of the cold insulation section 84 is open. FIG. 12 shows a state where a part of an intake duct 846 is removed. The cold insulation section 84 is a storage for storing the QC specimen container 150. The cold insulation section 84 has a function of cooling the QC specimen container 150. The cold insulation section 84 includes a block-shaped cold insulation section main body 841 that forms a cold insulation chamber 841a for cooling and storing the QC specimen container 150, a cover 842 that covers the cold insulation chamber 841a, and an opening/closing mechanism 843 for the cover 842. The cold insulation section main body 841 and the cover 842 have a rectangular shape in a plan view that is long in the left-right direction. The cold insulation section 84 includes a pedestal 848 on which the cold insulation section main body 841 is placed.

In the cold insulation section 84, temperature of the cold insulation chamber 841a, opening/closing of the cover 842 and the like are controlled by the control section 82a. The cold insulation chamber 841a is at a temperature of, for example, 2° C. to 8° C., and is constantly controlled to a substantially constant temperature. The cooling of the cold insulation section 84 is continued even after the specimen analysis system 1 is shut down. The cover 842 is automatically opened and closed when the QC specimen container 150 is taken in and out.

The cold insulation section main body 841 includes a plurality of housing portions 841b for housing the QC specimen container 150 one by one in an upright state in the cold insulation chamber 841a covered with the cover 842. The housing portion 841b is a hole into which the QC specimen container 150 opened upward can be inserted. In the example shown in FIG. 12, nine housing portions 841b are formed in a row in the left-right direction. The housing portion 841b is formed so that the upper portion of the tube 101 gripped by the arms 85b of the transfer section 85 protrudes from the upper surface of the cold insulation section main body 841 with the QC specimen container 150 inserted.

A vaporization compression type cooling device including a compressor may be used as a cooling means in the cold insulation section main body 841. In the present embodiment or embodiments, a Perche element is built in from the viewpoint of miniaturization of the device, and the like. The cold insulation section main body 841 is provided with a fan 845 as a heat radiating means of the Perche element. The cold insulation section main body 841 is provided with a metal cooling block, heat radiation fins, a temperature sensor, and the like, which are cooled by the Perche element.

The cover 842 closes the opening of the cold insulation chamber 841a to keep the inside of the cold insulation chamber 841a airtight and at a low temperature. The cover 842 is formed in a block shape like the cold insulation section main body 841. The cover 842 has a recess 842a formed on the inner surface facing the cold insulation section main body 841 side. The inner surface of the cover 842 has a flat peripheral edge that abuts on the upper surface of the cold insulation section main body 841, and the recess 842a is formed in the center along the longitudinal direction of the cover 842. A rubber packing may be attached to the peripheral edge of the inner surface of the cover 842.

The cover 842 is configured to rotate to the right and open by the opening/closing mechanism 843 provided at the right end portion of the cold insulation section main body 841.

The opening/closing mechanism 843 includes a rotating shaft 843a, a bearing member 843b fixed to the right end portion of the cold insulation section main body 841 and rotatably supporting the rotating shaft 843a, a connecting member 843c connecting the right end portion of the cover 842 and the rotating shaft 843a, and driving mechanisms for rotating the rotating shaft 843a. The opening/closing mechanism 843 has an endless belt 843d suspended at the rear end of the rotating shaft 843a and a rotating shaft on which the belt 843d is suspended, and is provided with a motor 843e for driving the belt 843d, as the driving mechanisms for the rotating shaft 843a. The rotating shaft 843a extends in the front-rear direction. The motor 843e is fixed to the pedestal 848.

The opening/closing mechanism 843 includes two sensors 843f and 843g attached to the bearing member 843b and a metal plate 843*h* fixed to the front end of the rotating shaft 843*a*. Suitable examples of the sensors 843*f* and 843*g* are proximity sensors such as magnetic sensors or eddy current type sensors. The sensors 843*f* and 843*g* are configured to be able to detect the opening and closing of the cover 842 by, for example, detecting the proximity of the metal plate 843*h* that moves with the rotation of the rotating shaft 843*a*. In the present embodiment or embodiments, the sensor 843*f* detects the open state of the cover 842, and the sensor 843*g* detects the closed state of the cover 842.

The fan 845 is a heat radiating means for releasing the heat of the Perche element. The fan 845 is installed behind the cold insulation section main body 841. The intake duct 846 and an exhaust duct 847 are connected to the fan 845. The intake duct 846 extending to the right is provided above the fan 845, and the exhaust duct 847 extending downward is provided below the fan 845. When the fan 845 operates, air is sucked from a suction port of the intake duct 846, passes through a heat generating portion, and is exhausted from an exhaust port of the exhaust duct 847.

Transfer Section 85

Figure 13:
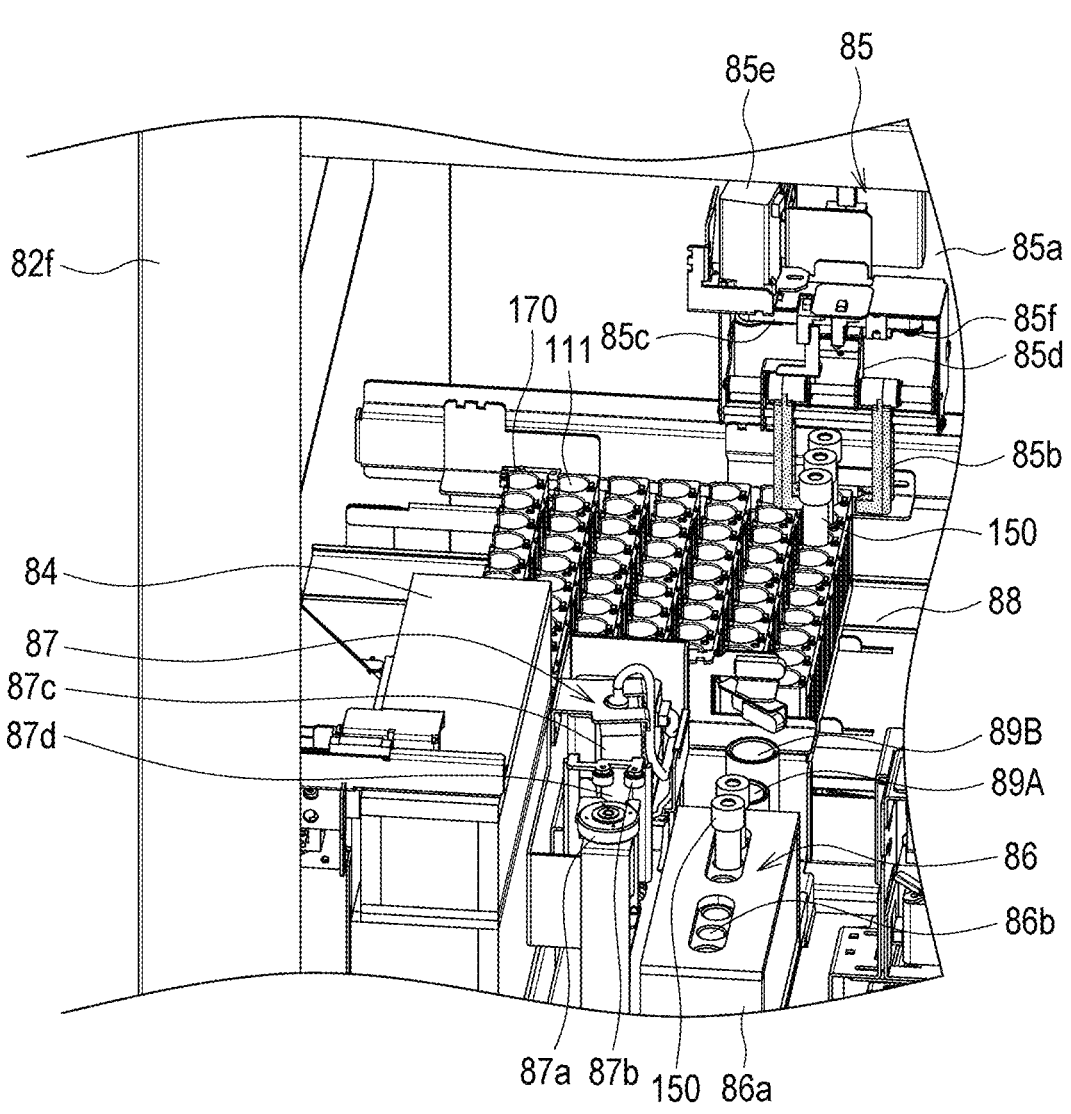
FIG. 13 is a perspective view showing an internal structure of the supply unit.

As shown in FIG. 13, the transfer section 85 includes a plate-shaped base portion 85*a* that is long in the vertical direction and a pair of arms 85*b* that grip the QC specimen container 150. The base portion 85*a* is provided so that the plate surface is along the vertical direction and the front-rear direction. The pair of arms 85*b* are arranged at intervals in the front-rear direction. The pair of arms 85*b* can move in directions close to and away from each other. The QC specimen container 150 is gripped when the pair of arms 85*b* approach, and the QC specimen container 150 is released when the pair of arms 85*b* are separated.

The transfer section 85 is configured to take out the QC specimen container 150 from the transfer holder 834 of the first charging section 83A and transfer the transfer holder 834 to the cold insulation section 84 via the information reading section 87. The QC specimen container 150 is taken out from the cold insulation section 84. The QC specimen container 150 is transferred to the rack housing section 88 via the heating section 86. The transfer section 85 returns the QC specimen container 150 collected in the rack housing section 88 after the measurement in the measurement unit to the cold insulation section 84. Alternatively, the transfer section 85 charges the used QC specimen container 150 into the first collection section 89A for disposal.

The transfer section 85 is configured to take out the cleaning agent container 180 from the second charging section 83B, and the cleaning agent container 180 is transferred to the rack housing section 88. The cleaning agent container 180 is taken out from the take-out section 839 (see FIG. 8 and the like) of the second charging section 83B. The cleaning agent container 180 is directly transferred to a front end rack of the rack housing section 88. The transfer section 85 charges the used cleaning agent container 180 collected in the rack housing section 88 after cleaning of the measurement unit into the second collection section 89B for disposal.

The base portion 85*a* is provided with the endless belt 85*c* extending in the front-rear direction, a pair of connecting members 85*d* connecting the pair of arms 85*b* and the belt 85*c*, a motor 85*e* including a rotating shaft on which the belt 85*c* is suspended, and a pulley 85*f* on which the belt 85*c* is suspended, as driving mechanisms for the arms 85*b*. The pair of arms 85*b* are movably attached to the base portion 85*a* by these driving mechanisms. For the motor 85*e*, for example, a stepping motor is used.

Figure 14:
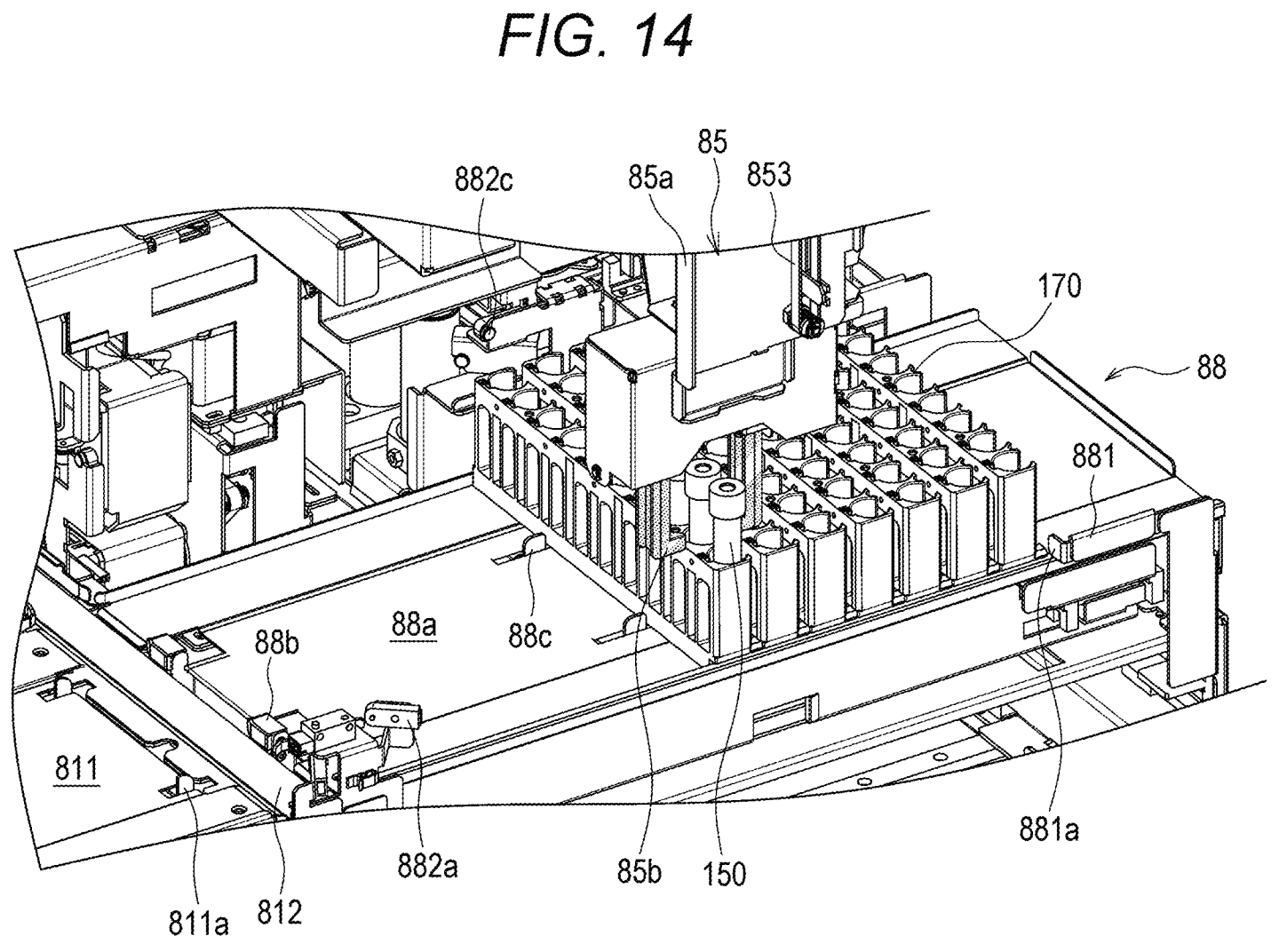

The pair of arms 85*b* can also move in three directions: front-rear, left-right, and up-down. The transfer section 85 includes a first driving mechanism that moves the base portion 85*a* to which the arms 85*b* are attached in the front-rear direction, and a second driving mechanism that moves the base portion 85*a* in the left-right direction. The upper end of the base portion 85*a* is suspended by engaging with the first driving mechanism and the second driving mechanism, and is supported so as to be movable front and rear and left and right with respect to the frame 82*f*. The base portion 85*a* is provided with a third driving mechanism 853 (see FIG. 14 illustrated later) that moves the driving mechanism for the arms 85*b* including the pair of arms 85*b*, the belt 85*c* and the like, in the vertical direction.

The pair of arms 85*b* grip, for example, the upper portion of the tube 101 of the QC specimen container 150. Since the QC specimen container 150 includes a cap 102 with a larger outer diameter than that of the tube 101, the arms 85*b* grip the upper portion of the tube 101, so that the arms 85*b* are caught by the cap 102, and pull out of the QC specimen container 150 can be more reliably prevented. Since the cleaning agent container 180 is formed with a flange 181 protruding outward in the radial direction at the upper end of the container, the pair of arms 85*b* grip a portion slightly below the flange 181.

Heating Section 86

As shown in FIG. 13, the heating section 86 includes a block-shaped heating section main body 86*a* and a housing portion 86*b* for housing the QC specimen container 150. The housing portion 86*b* is a hole into which the QC specimen container 150 opened upward can be inserted. A plurality of housing portions 86*b* are formed in the heating section main body 86*a*. The housing portion 86*b* stores the QC specimen container 150 one by one in an upright state. In the example shown in FIG. 13, six housing portions 86*b* are formed in a row in the left-right direction.

The housing portion 86*b* is preferably formed so that the upper portion of the tube 101 gripped by the arms 85*b* of the transfer section 85 protrudes from the upper surface of the heating section main body 86*a* when the QC specimen container 150 is inserted. The heating section 86 does not have a cover, and there are no large protrusions on the upper surface of the heating section main body 86*a*. The number, arrangement and the like of the housing portions 86*b* are not particularly limited, and for example, the housing portions 86*b* may be arranged in a staggered pattern.

As described above, the heating section 86 has a function of heating the QC specimen container 150 that has been cooled and stored in the cold insulation section 84 and adjusting the temperature of the quality control material contained in the QC specimen container 150 to the measurement temperature in the measurement unit. The measurement temperature is 23° C.±3° C. Since the suitable cooling storage temperature is 2° C. to 8° C., the heating section 86 needs to raise the temperature of the quality control material by, for example, about 12° C. to 24° C. The heating section 86 heats the QC specimen container 150 inserted in the housing portion 86*b* so that the quality control material in the QC specimen container 150 reaches the measurement temperature.

The heating section 86 includes a heater that generates heat by electric power. The heater is preferably an aluminum block heater. Since the aluminum block heater uses an aluminum block as a heat medium, it is suitable because the aluminum block heater does not contaminate the container as compared with the case where a liquid medium is used. Since the aluminum block has high heat transfer property, the time required for raising the temperature can be shortened. By providing a heater, it is possible to quickly adjust the temperature even in an environment where the room temperature is low.

The set temperature of the heater is set to be higher than the measurement temperature as long as the quality control material is not deteriorated. The set temperature of the heater is set to 23° C.±3° C. in a preferable example. The heating section 86 may include an air blowing means such as a fan that blows air to the housing portion 86b, and the quality control material is heated by blowing air into the QC specimen container 150 by the air blowing means. The heating section 86 may include a heater and a fan.

Information Reading Section 87

As shown in FIG. 13, the information reading section 87 includes rollers 87a and 87b arranged so as to sandwich a housing portion 87d of the QC specimen container 150 and a reading portion 87c that reads the QC specimen ID from the machine-readable label 103 of the QC specimen container 150. At least one of the rollers 87a and 87b is configured to be movable and rotate in a direction close to each other. The information reading section 87 drives at least one of the rollers 87a and 87b to rotate the QC specimen container 150 arranged in the housing portion 87d, and the reading portion 87c reads the QC specimen ID. The reading portion 87c is, for example, a barcode reader.

The QC specimen container 150 is transferred from the first charging section 83A to the information reading section 87, and the QC specimen container 150 whose QC specimen ID has been read in the information reading section 87 is transferred to the cold insulation section 84 for cooling and storage. The information reading section 87 transmits the information on the read QC specimen ID to the control section 82a, and the control section 82a executes a process related to quality control using the information. As will be described in detail later, the control section 82a manages a housing position of the QC specimen container 150 in the cold insulation section 84 by using the QC specimen ID to enable selection of the QC specimen container 150 to be used for quality control measurement.

Rack Housing Section 88

Figure 15:
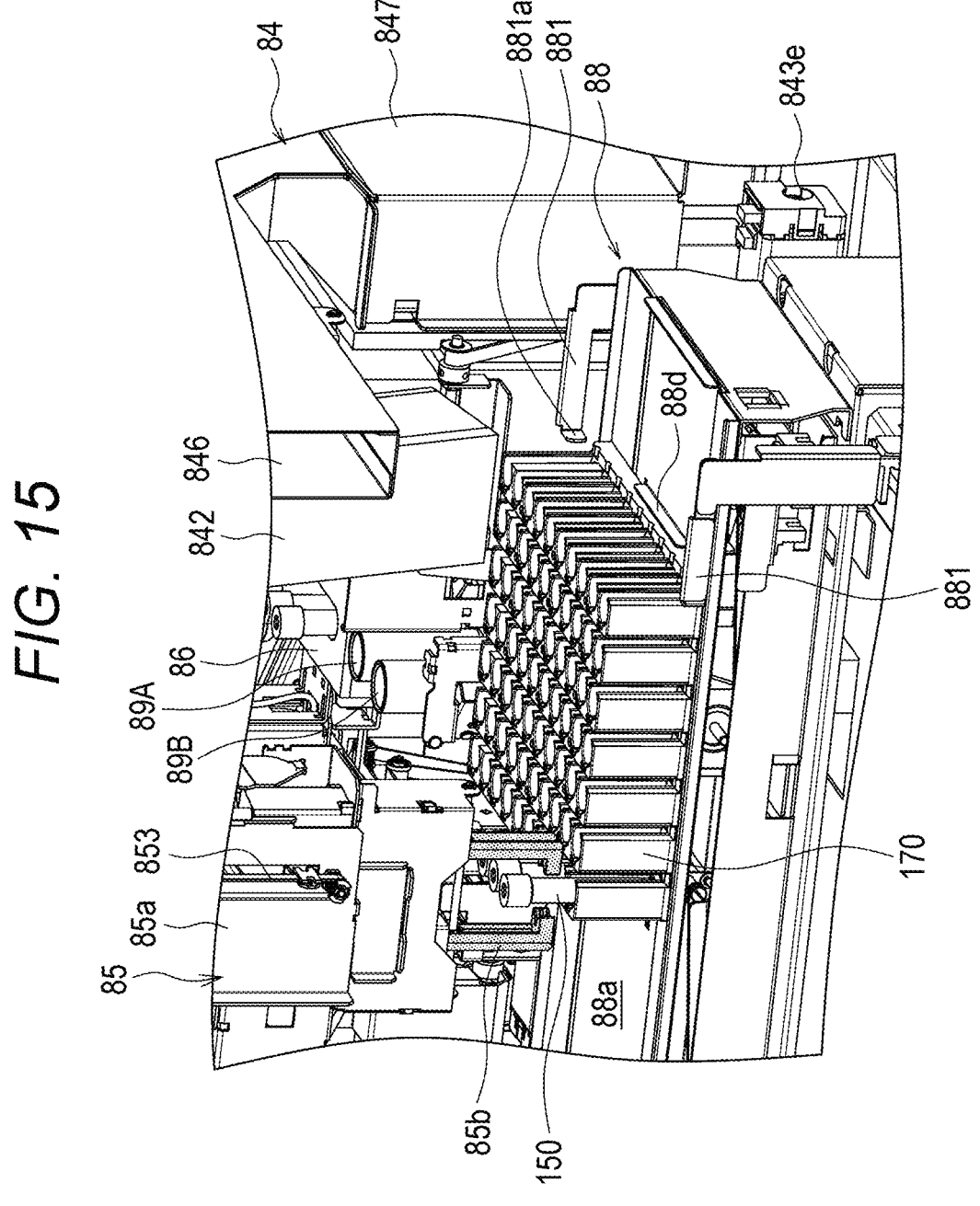
FIG. 15 is a perspective view showing an internal structure of a supply unit, viewing a rack housing section from rear side.

FIGS. 14 and 15 are perspective views showing an internal structure of the storage adjustment unit 82, which show the rack housing section 88 in an enlarged view. The rack housing section 88 includes a transport path 88a capable of transporting the empty rack 170 in the front-rear direction and capable of storing a plurality of empty racks 170. The transport path 88a extends long in the front-rear direction at the right end portion of the storage adjustment unit 82. In the present embodiment or embodiments, a maximum of seven empty racks 170 can be stored in the transport path 88a.

The transport path 88a is provided with three stoppers 88b, 88c and 88d in order from the front. The stopper 88c is arranged at the center of the transport path 88a in the front-rear direction. The stopper 88c regulates forward movement of the empty rack 170 stored in the transport path 88a. The stopper 88d is arranged on the rear end side of the transport path 88a more than the stopper 88c. The stopper 88d regulates backward movement of the empty rack 170. An area sandwiched between the stoppers 88c and 88d becomes an area in which the empty rack 170 can be stored. In the present embodiment or embodiments, a distance between the stoppers 88c and 88d in the front-rear direction corresponds to a length of seven empty racks 170 in the front-rear direction.

As described above, the rack housing section 88 is also a place for housing the QC specimen container 150 and the cleaning agent container 180 in the empty rack 170. Since the QC specimen container 150 and the cleaning agent container 180 are housed in the front end rack located at the frontmost of the plurality of empty racks 170, a space to serve as a passage of the transfer section 85 is secured above the front end rack of the transport path 88a and the vicinity thereof. The position of the front end rack is determined by the stopper 88c that stops the empty rack 170 from moving forward. In the present embodiment or embodiments, the position of the front end rack is arranged side by side in the left-right direction with the first collection section 89A, the second collection section 89B, and the heating section 86.

The rack housing section 88 includes transport arms 881 for transporting the empty rack 170, the QC specimen rack 160 in which the QC specimen container 150 is housed, and a rack in which the cleaning agent container 180 (hereinafter, referred to as "cleaning agent rack") in the front-rear direction. The transport arms 881 can push the empty rack 170 or the like forward. The transport arms 881 also can pull the empty rack 170 or the like backward. The rack housing section 88 is provided with a pair of transport arms 881 so as to sandwich the transport path 88a from both the left and right sides. At tips of the pair of transport arms 881, a claw portion 881a projecting inward of the transport path 88a is formed.

Figure 16:
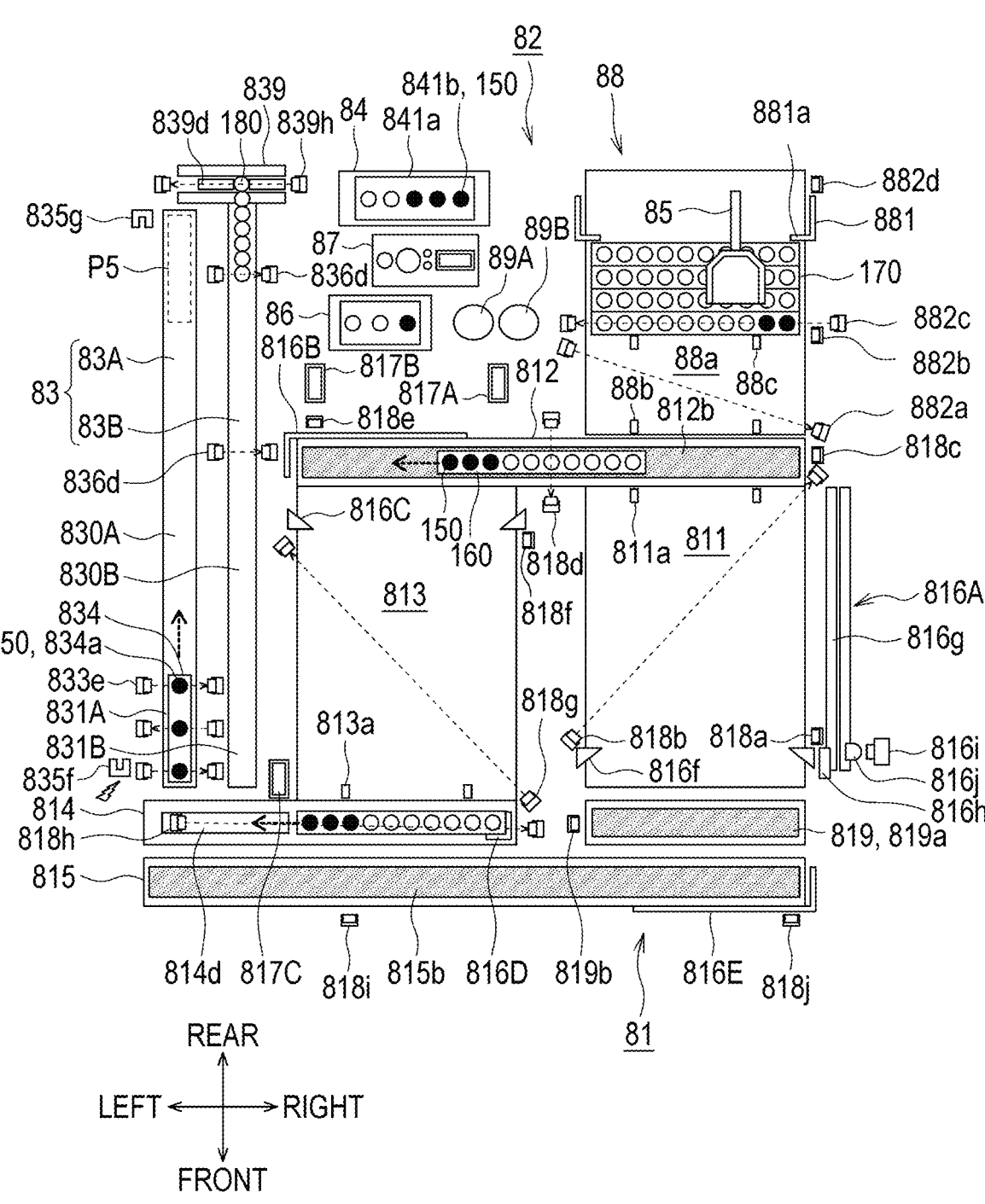
FIG. 16 is a diagram schematically showing a configuration (e.g., internal layout) of a supply unit which is an example of an embodiment or embodiments, showing a state of supplying QC specimen racks.
Figure 17:
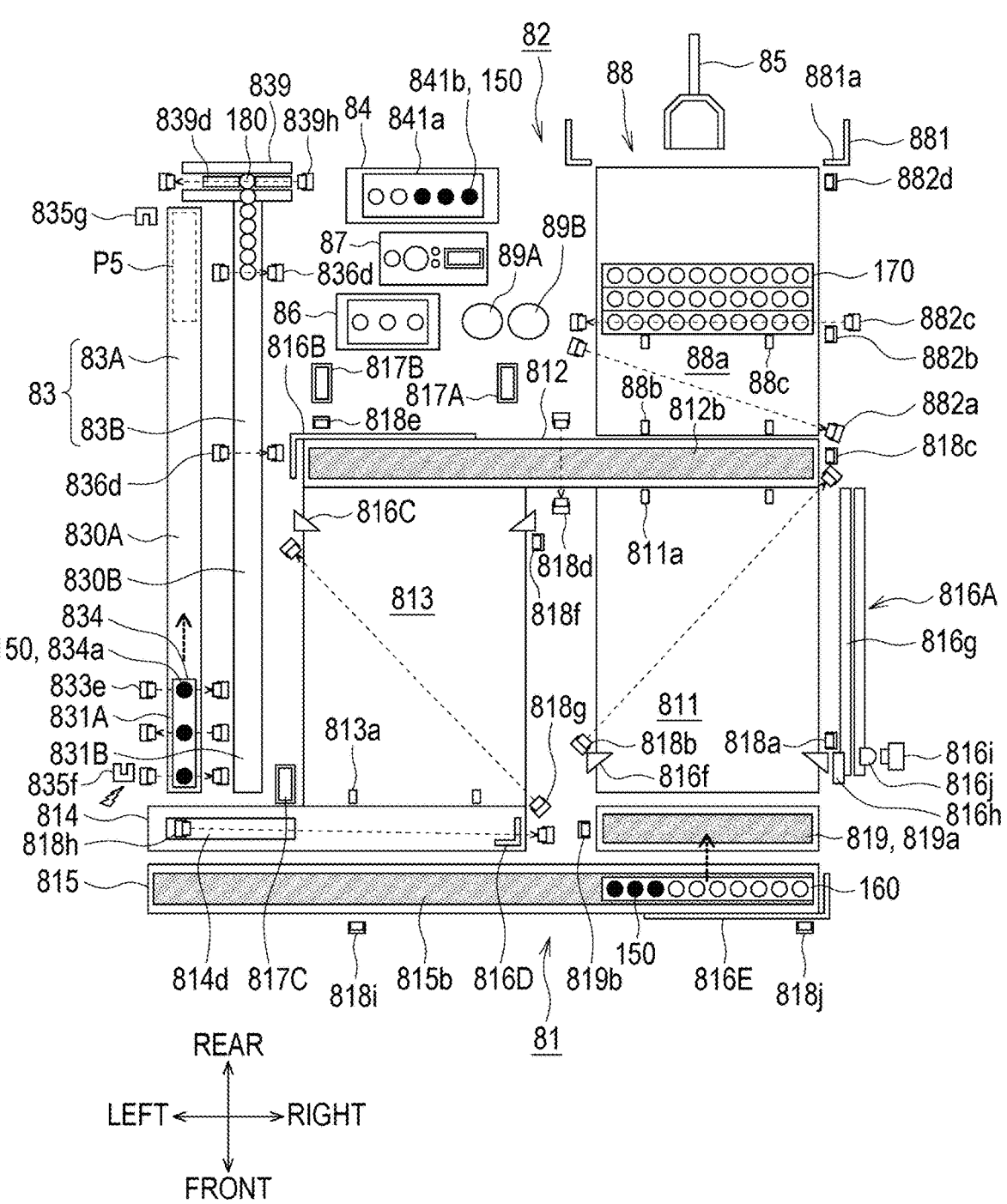
FIG. 17 is a diagram schematically showing a configuration (e.g., internal layout) of a supply unit which is an example of an embodiment or embodiments, showing a state of collecting the QC specimen rack.

Hereinafter, a configuration of the rack housing section 88 will be described in more detail with reference to FIGS. 16 and 17. The transport path 88a of the rack housing section 88 is connected to the second transport path 812 of the conveyor section 81. The transport path 88a is arranged so as to face the first transport path 811 with the second transport path 812 in between. That is, the first transport path 811 and the transport path 88a are arranged side by side in the front-rear direction. The transport path 88a is connected to the right end side of the second transport path 812. The transport path 88a is connected to the first transport path 811 and the third transport path 813 via the second transport path 812.

The stopper 88b in the transport path 88a is a movable stopper arranged at the front end of the transport path 88a. The stopper 88b prevents the specimen rack 110 or the like pushed out from the first transport path 811 to the second transport path 812 from entering the transport path 88a. The stopper 88b is lowered so as not to protrude from the upper surface of the transport path 88a when the empty rack 170 or the like is carried into the transport path 88a. Since the empty rack 170 and the like are transported to the rear of the stopper 88c, the stopper 88c is lowered interlocking with the stopper 88b. The stoppers 88b and 88c may be mechanically connected by, for example, a link mechanism or the like.

The transport arms 881 can move to the front of the second transport path 812 along the front-rear direction. The transport arms 881 can push out the QC specimen rack 160 or the like to the second transport path 812. The transport arms 881 also can pull the QC specimen rack 160 or the like from the second transport path 812 into the transport path 88a. The QC specimen rack 160 is transported from the rack housing section 88 to the third transport path 813 and the fourth transport path 814 via the second transport path 812. The QC specimen rack 160 returned to the supply unit 80 by the fifth transport path 815 is collected in the rack housing section 88 via the first transport path 811 and the second transport path 812.

The transport arms 881 move in the front-rear direction by driving mechanisms similar to those of the first delivery section 816A. The two transport arms 881 are configured to be movable in directions close to and away from each other. The two transport arms 881 can send out the QC specimen rack 160 or the like to the second transport path 812 one by one. Specifically, the transport arms 881 can move in the left-right direction between an engaging position where the claw portion 881*a* of the transport arm 881 is located on the transport path 88*a* and engages with the rack on the transport path 88*a*, and a retracted position where the claw portion 881*a* retracts from the transport path 88*a*.

For example, when the transport arms 881 are moved forward from the rear of the transport path 88*a* beyond the empty rack 170 and the QC specimen rack 160 (front end rack) is pushed out to the second transport path 812, the transport arms 881 in the retracted position are moved to the position of the QC specimen rack 160. Then, the transport arms 881 are moved to the engaging position, and the claw portion 881*a* is inserted between the QC specimen rack 160 and the empty rack 170 one behind the QC specimen rack 160. By moving the transport arms 881 forward in this state, the rear surface of the front end rack is pushed by the claw portion 881*a* of the transport arms 881, and the QC specimen rack 160 is pushed out to the second transport path 812.

The rack housing section 88 is provided with four sensors 882*a*, 882*b*, 882*c* and 882*d* in order from the front along the transport path 88*a*. The sensor 882*a* detects a rack between the stoppers 88*b* and 88*c* on the front end side of the transport path 88*a*, and the sensor 882*b* detects the front end rack. When the empty rack 170 is stored in the rack housing section 88, the transport arms 881 transfer the empty rack 170 forward so that there is always a front end rack capable of housing the QC specimen container 150 and the cleaning agent container 180.

The sensor 882*c* detects the QC specimen container 150 and the cleaning agent container 180 housed in the front end rack. The sensor 882*d* detects the presence or absence of a rack on the rear end side of the transport path 88*a*, specifically, the empty rack 170 immediately before the stopper 88*d* (see FIG. 15). When the sensor 882*d* does not detect the empty rack 170, it means that a rack housing either the QC specimen container 150 or the cleaning agent container 180 is transported to the measurement unit, or there is a space to house the empty rack 170 in the rack housing section 88.

For the sensors 882*a*, 882*b*, 882*c* and 882*d*, an optical sensor can be used, like the sensor of the conveyor section 81. For example, an optical sensor in which a light emitter and a light receiver are separated is used for the sensors 882*a* and 882*c*, and a reflective optical sensor in which a light emitter and a light receiver are integrated is used for the sensors 882*b* and 882*d*. As will be described in detail later, the control section 82*a* controls the stoppers 88*b* and 88*c* and the transport arms 881 based on detection information of each sensor and the like to execute rack transport in the rack housing section 88.

Operation Screen of Monitor 91

Hereinafter, a screen displayed on the monitor 91 of the supply unit 80 will be described in detail with reference to FIGS. 18, 19, 20, 21, 22, 23, 24, 25, 26, and 27.

Figure 18:
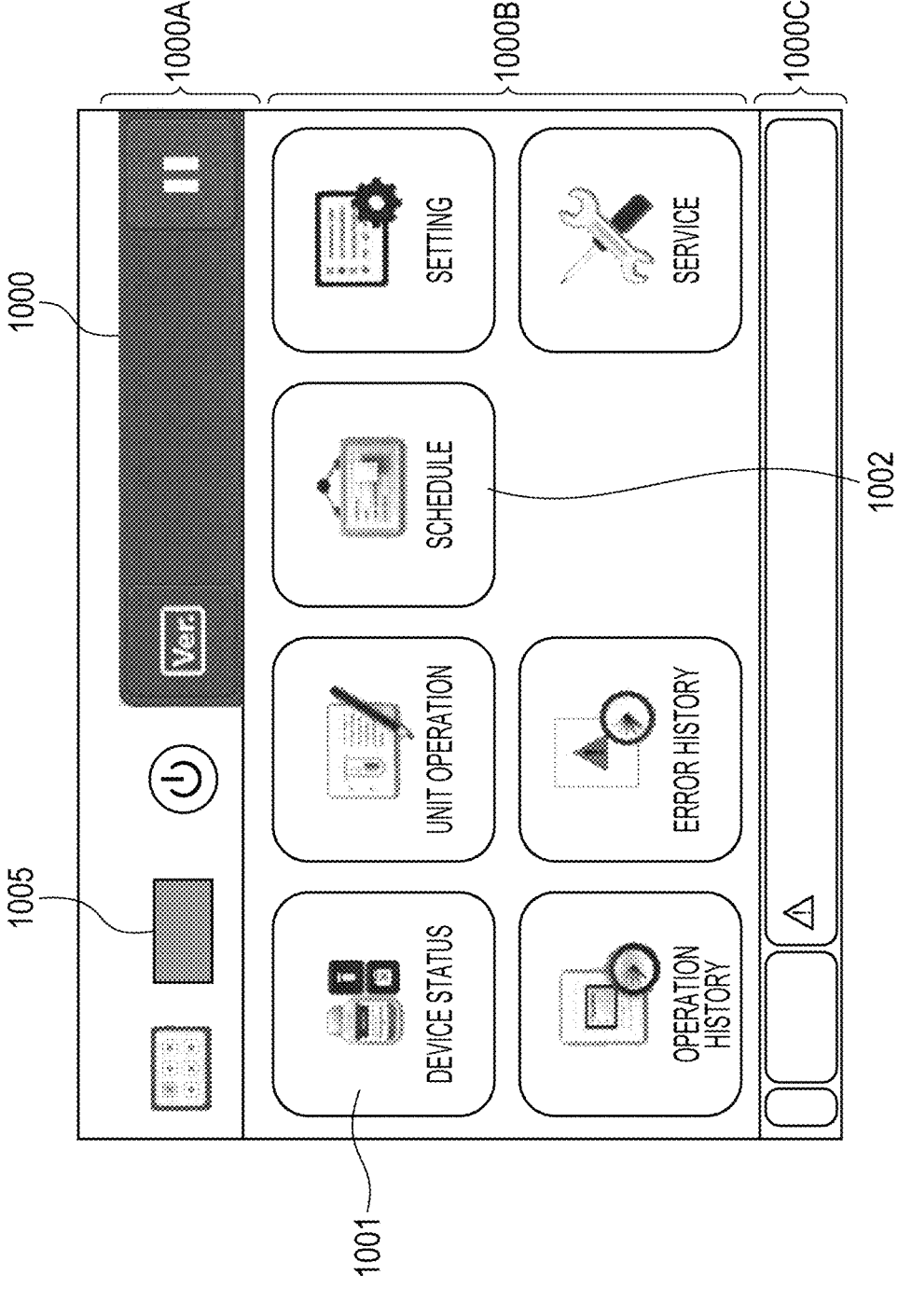
FIG. 18 is an example of a home screen displayed on a monitor of a supply unit.
Figure 27:
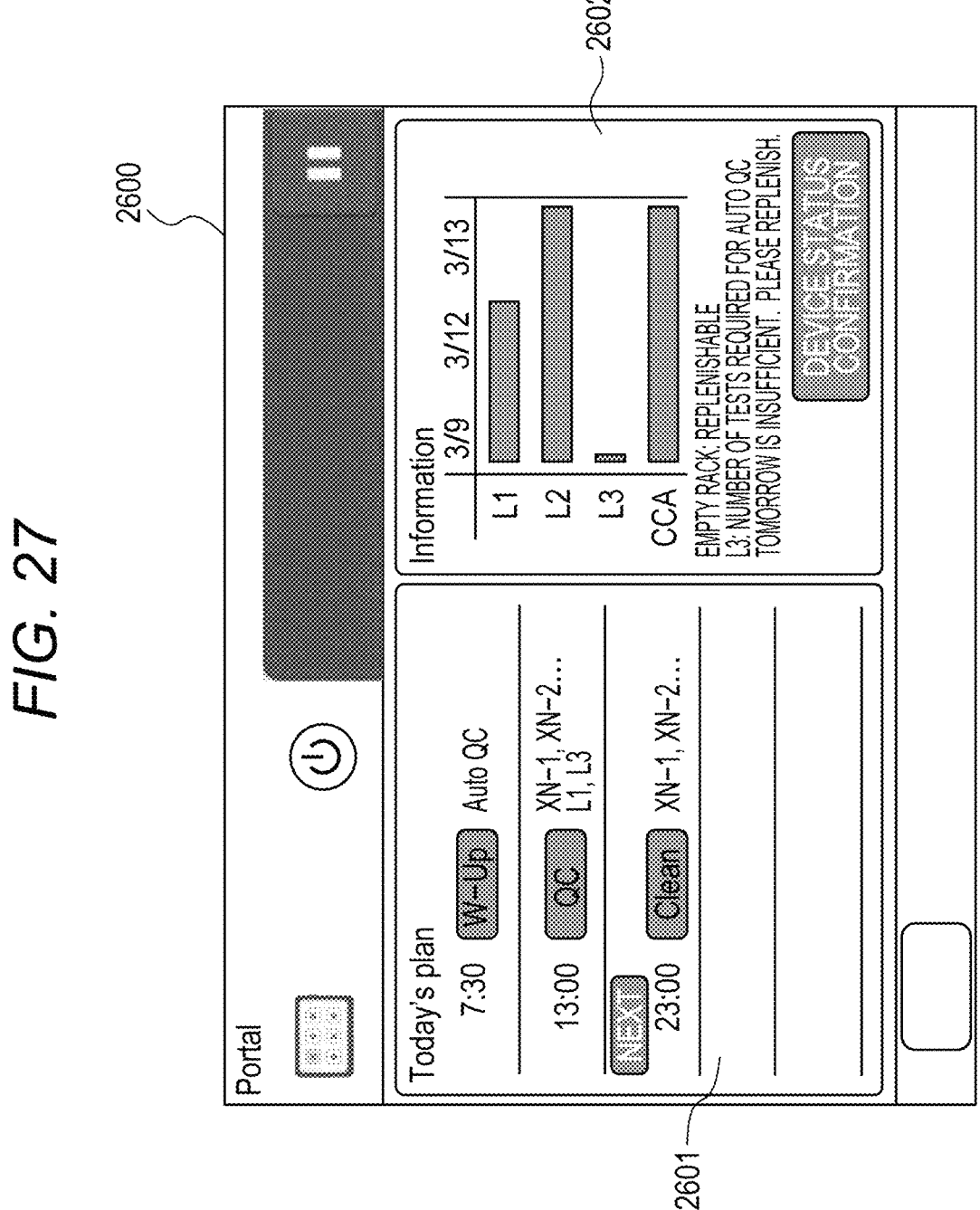
FIG. 27 is an example of a portal screen including a schedule display area and an inventory display area.

FIG. 18 is an example of a home screen 1000 displayed on the monitor 91 of the supply unit 80. The home screen 1000 includes a toolbar 1000A, a main area 1000B on which an operation menu is displayed, and a status display area 1000C on which a status is displayed. As described above, the monitor 91 is composed of a touch panel, and all icons displayed on the screen 1000 are displayed so that a user can select. On the toolbar 1000A, a portal screen display icon 1005 for displaying a portal screen 2600 shown in FIG. 27 illustrated later is arranged.

In the main area 1000B, a device status icon 1001 for checking the status of the supply unit 80 or replenishing consumables for the supply unit 80 and a schedule icon 1002 for registering and editing a schedule are displayed. The main area 1000B may include additional icons, as shown in FIG. 18.

FIG. 19 is an example of a device status screen 2000 displayed in response to selection of the device status icon 1001. The device status screen 2000 includes a QC status window 2001, a cleaning agent container inventory window 2006, an empty rack inventory window 2007, a disposal box window 2008, and a temperature display window 2009, as contents to be displayed in the main area.

The QC status window 2001 includes a QC specimen list 2001A that displays a list of information on QC specimens under the control of the supply unit 80, and a remaining amount display part 2001B that displays remaining amounts for each concentration level of the QC specimens under control.

The QC specimen list 2001A displays a list of information on the QC specimen containers 150 under the control of the supply unit 80. The QC specimen list 2001A contains, for example, nine rows corresponding to nine housing portions 841*b* provided in the cold insulation section 84, as shown in FIG. 19. The QC specimen list 2001A includes, in order from the leftmost column, a first column showing the position number of the housing portion 841*b*, a second column showing the concentration level of the QC specimen, a third column showing the lot number, a fourth column showing the number of remaining tests, and a fifth column showing the expiration date.

In the example of FIG. 19, for example, the information on the QC specimen container 150 housed in the housing portion 841*b* at position number 1 is displayed in a row corresponding to the position number "1". In the example of FIG. 19, for the QC specimen container 150 housed in the position number "1", information is registered with a concentration level of "level 1", a lot number of "A001XXXX", a remaining amount of 3 tests, and an expiration date of "Mar. 30, 2021".

Figure 28:
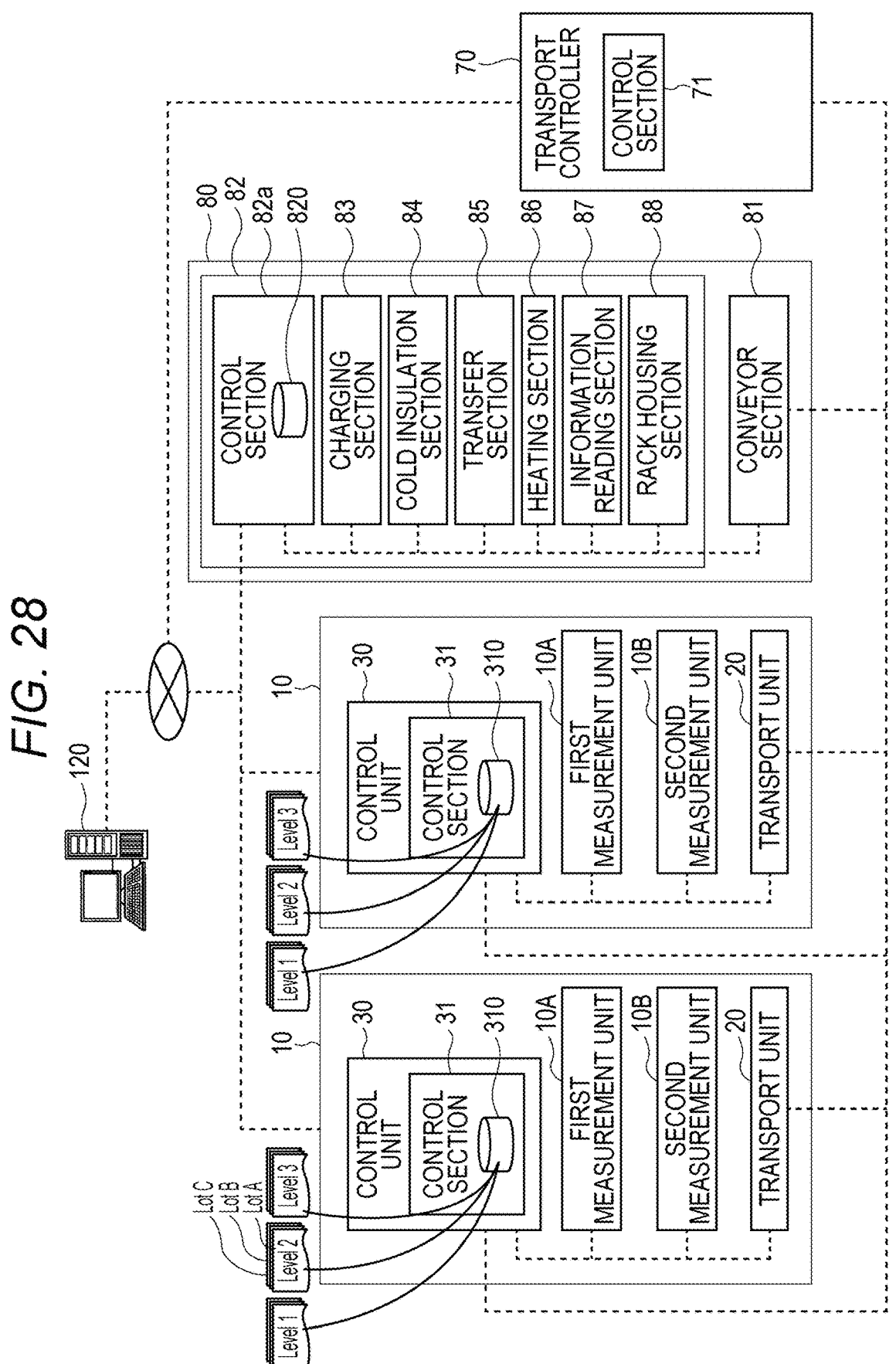
FIG. 28 is a block diagram showing a configuration of a supply unit, also showing a connection relationship between a supply unit, a measurement unit, and a transport controller.

The information on the QC specimen list 2001A is registered by reading the information on the QC specimen container 150 set via the charging section 83 described above by the information reading section 87. The machine-readable label 103 of the QC specimen container 150 stores attribute information including the concentration level, lot number, number of remaining tests and expiration date of the QC specimen. The information reading section 87 acquires the above information based on the information read from the machine-readable label 103. The information reading section 87 transmits the acquired information to the control section 82*a*. The QC specimen container 150 whose information has been read is housed by the transfer section 85 in one empty housing portion 841*b* of the cold insulation section 84. The control section 82*a* stores the above information read by the information reading section 87 in a database 820 (see FIG. 28 illustrated later) in association with the position number of the housing portion 841*b* in which the QC specimen container 150 is housed.

The information on the QC specimen list 2001A displays a list of information on the QC specimen containers 150 under the control of the supply unit 80. Even when the QC specimen container 150 is in the state of being taken out from the cold insulation section 84 (for example, in the state of being transported for quality control measurement), the information on the QC specimen containers 150 are displayed in the row of the position number corresponding to the QC specimen containers 150. The information on the QC specimen container 150 taken out from the cold insulation section 84 is displayed in a different background color as shown by hatching in FIG. 19 so as to be distinguished from the QC specimen container 150 stored in the cold insulation section 84.

As shown in FIG. 19, when the number of remaining tests falls below a predetermined value, the QC specimen list 2001A highlights the corresponding cell in the fourth column displaying the remaining amount. For example, in the example of FIG. 19, the color of the cell corresponding to the QC specimen container 150 at position number 3 where the number of remaining tests is less than 1 is reversed and displayed. The threshold value to be highlighted can be set as appropriate. For example, the cell may be highlighted when the number of remaining tests is less than 5. As a result, the user can easily grasp the presence of the QC specimen container 150 whose remaining amount is low or zero.

As shown in FIG. 19, when the expiration date of the QC specimen container 150 housed in the cold insulation section 84 has expired, the QC specimen list 2001A highlights the corresponding cell in the fifth column displaying the expiration date. For example, in the example of FIG. 19, the color of the cell corresponding to the QC specimen container 150 at position number 6 whose expiration date has passed is reversed and displayed. The conditions for highlighting can be set as appropriate. For example, the cell may be highlighted when the number of days remaining until the expiration date falls below the threshold value. For example, the cell may be highlighted when the number of days remaining until the expiration date falls below 10 days. As a result, the user can easily grasp the presence of the QC specimen container 150 whose expiration date is approaching or has passed.

In the example of FIG. 19, only the cells in the fourth or fifth column are highlighted, but the entire row may be highlighted.

The remaining amount display part 2001B is provided above the QC specimen list 2001A. The remaining amount display part 2001B displays the total number of remaining uses for each type of control blood, that is, for each concentration level of the QC specimen container 150. In the example of FIG. 19, the numbers of remaining tests for QC specimens at concentration levels 1, 2 and 3 are displayed as 44 tests, 53 tests, and 1 test, respectively. The values of the remaining amount display part 2001B are equal to values obtained by adding the numbers of remaining tests of the QC specimens displayed in the QC specimen list 2001A for each concentration level. According to the remaining amount display part 2001B, it is not necessary for the user to calculate the number of remaining tests for each concentration level, and management is easy.

The cleaning agent container inventory window 2006 displays the remaining number of cleaning agent containers 180 stored in the supply unit 80. As described above, a plurality of sensors 836d are installed in the second charging section 83B along the transfer path 830B. Of these, the sensor 836d on the front side of the device (lower side of the paper in FIG. 8) is arranged at a position where a 15th cleaning agent container from the beginning can be detected. The control section 82a displays the remaining number of the cleaning agent containers 180 based on output from the sensor 836d on the front side of the device. For example, when the cleaning agent container 180 is detected by the sensor 836d, as shown in FIG. 19, "15+" indicating that the remaining number is 15 or more is displayed. After the sensor 836d detects the cleaning agent container 180, when the sensor 836d stops detecting the cleaning agent container 180 due to consumption of the cleaning agent container 180, the control section 82a displays the number of inventory with reducing the number used from 15.

In a supply unit 80K of a modified example described later, since the number of all the cleaning agent containers set in the unit is recognized by the control section 82a, the displayed number of inventory is changed according to the number of cleaning agent containers used by the supply unit 80.

The empty rack inventory window 2007 displays the number of empty racks 170 housed in the rack housing section 88. The control section 82a recognizes the number of empty racks 170 based on outputs of the sensors 882c and 882d. The control section 82a displays the number in the empty rack inventory window 2007.

In the disposal box window 2008, the number of containers that can be disposed of is displayed in the first collection section 89A and the second collection section 89B, which are disposal boxes.

In the temperature display window 2009, temperature inside the cold insulation section 84, temperature of a heating block of the heating section 86, and temperature of outside air temperature are displayed.

Figure 21:
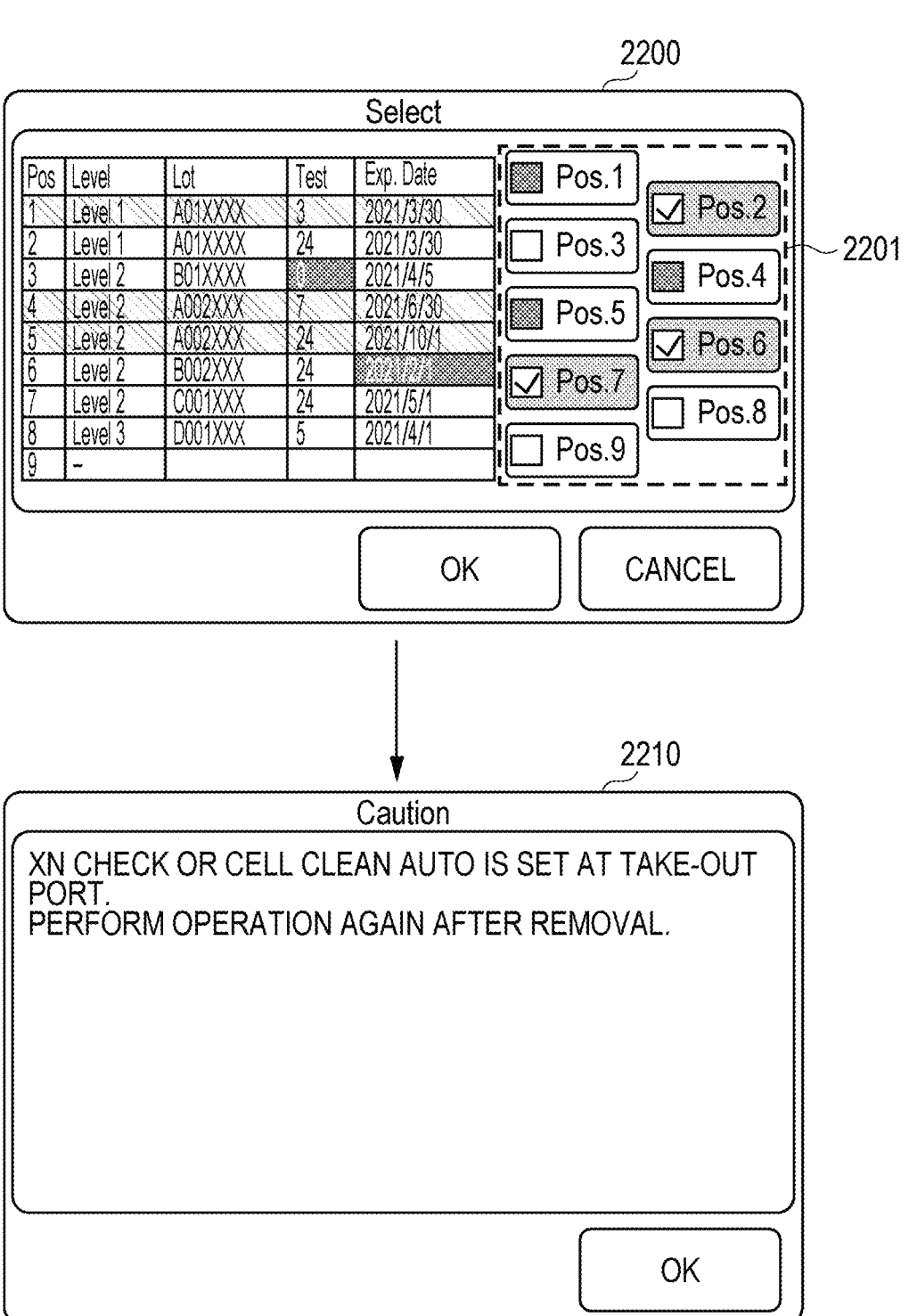
FIG. 21 is an example of a QC specimen take-out screen displayed when a take-out icon on a device status screen is pressed.

On a toolbar of the device status screen 2000, a shut down icon 2003, a take-out icon 2004, and a charge icon 2005 are displayed. The shut down icon 2003 is used to shut down all or part of the specimen analysis system 1. The take-out icon 2004 is used to take out the QC specimen container 150 stored in the cold insulation section 84. The take-out icon 2004 will be described with reference to FIG. 21 illustrated later. The charge icon 2005 is used to set the QC specimen container 150 in the first charging section 83A of the charging section 83.

Figure 20:
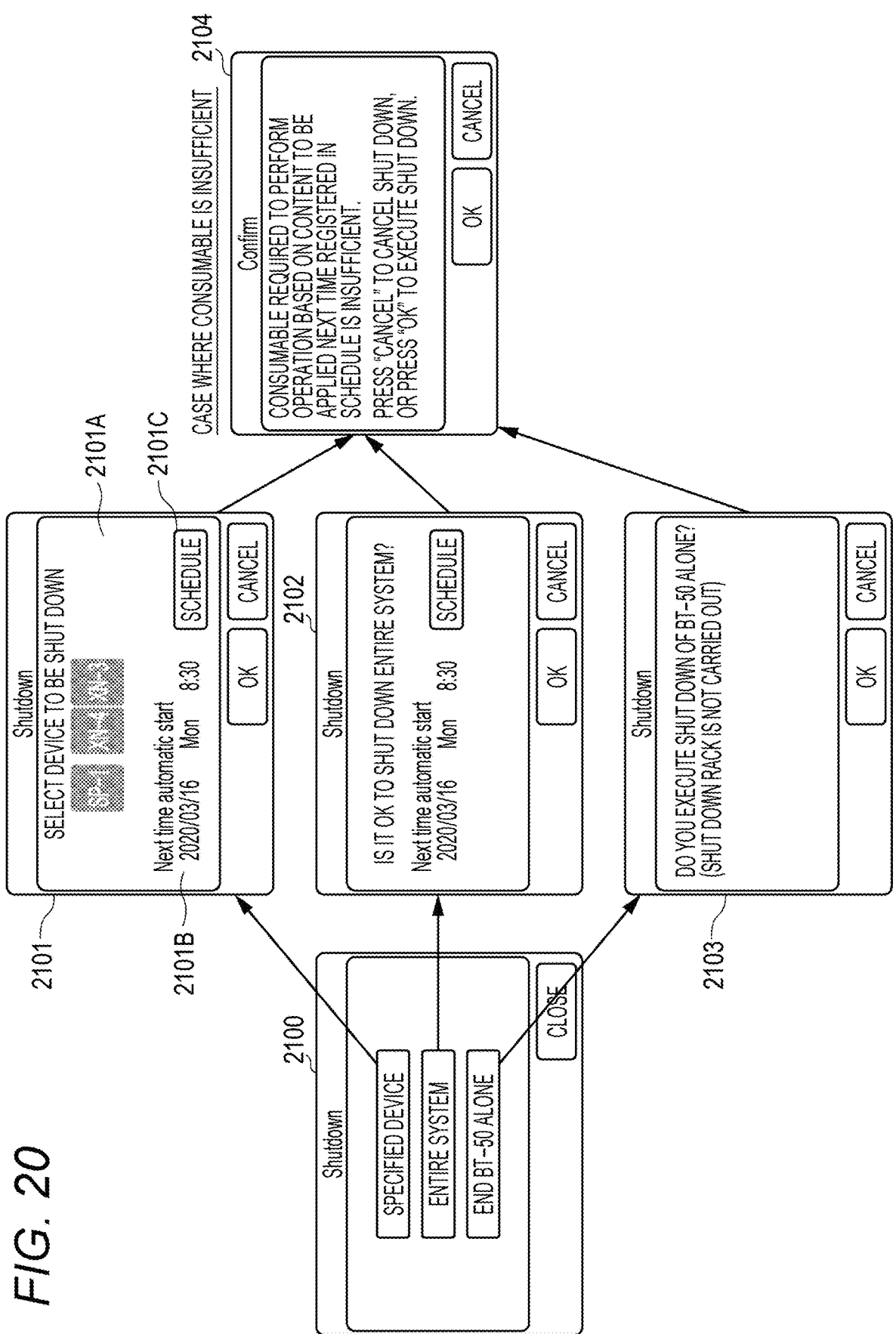
FIG. 20 is an example of a shut down screen displayed when a shut down icon on a device status screen is pressed.

FIG. 20 is an example of a shut down screen 2100 displayed when the shut down icon 2003 on the device status screen 2000 is pressed. The shut down screen 2100 displays a shut down menu. The shut down menu includes three choices: "DESIGNATED DEVICE", "ENTIRE SYSTEM", and "END SUPPLY UNIT (BT-50) ALONE".

When the "DESIGNATED DEVICE" is selected on the shut down screen 2100, a device selection screen 2101 is displayed. The device selection screen 2101 includes a device selection area 2101A that selectably displays a plurality of devices, namely, the measurement units 10A and 10B, and the process unit 40, according to layout of the specimen analysis system. The user selects a device to shut down according to a guidance on the screen. On the screen 2101, an auto start schedule 2101B planned next and a button 2101C for calling details of the next auto start schedule are displayed together. The user confirms the next auto start schedule displayed on the screen and then presses OK button at the bottom of the screen, thereby shutting down the selected device. Shut down of the measurement unit and the process unit refers that, for example, as described later with reference to FIG. 50, the cleaning agent rack housing the cleaning agent container is transported to the device, cleaning is executed in the device, and the power supply of the device is turned off after the cleaning is completed. In the following, the description will be provided by referring four measurement units constituting the specimen analysis system 1 as "XN-1", "XN-2", "XN-3", and "XN-4", respectively, and referring the process unit 40 as "SP-1".

When the "ENTIRE SYSTEM" is selected on the shut down screen 2100, a system shut down confirmation screen 2102 is displayed. Similar to the screen 2101, the screen 2102 displays the auto start schedule planned next and the button to call the details of the next schedule. When OK button at the bottom of the screen is pressed, the entire system is shut down.

When the "END SUPPLY UNIT ALONE" is selected, a supply unit shut down screen 2103 is displayed, which reconfirms the user that only the supply unit 80 will be shut down. When OK button at the bottom of the screen 2103 is pressed, only the supply unit 80 is shut down by itself. Shutting down the supply unit 80 means turning off the power supply of the supply unit 80, and does not transport the cleaning agent rack.

When the OK button is pressed on the screens 2101 to 2103, a screen 2104 is displayed in a case where a consumable to be used for auto QC associated with the next auto start schedule is insufficient. The screen 2104 contains a message "CONSUMABLE REQUIRED TO PERFORM CONTENT TO BE PERFORMED NEXT TIME REGISTERED IN SCHEDULE IS INSUFFICIENT." This screen 2104 is displayed in a case where the QC specimen container 150 stored in the cold insulation section 84 and the empty rack 170 housed in the rack housing section 88 are insufficient for the amount required to execute auto QC associated with the next auto start schedule when receiving a shut down instruction via the screens 2101 to 2103. The control section 82a of the supply unit 80 stores the number of remaining tests for each concentration level of the QC specimen container 150 stored in the cold insulation section 84, as described with reference to FIG. 19. The control section 82a also stores the number of empty racks 170 housed in the rack housing section 88. The control section 82a determines whether or not the inventory of the QC specimen container 150 is sufficient and whether or not the inventory of the empty rack 110 is sufficient, based on the QC conditions of the auto QC to be executed at the next auto start, and in the case of insufficiency, the control section 82a displays the screen 2104 on the monitor 91. The user presses cancel button to cancel the shut down and replenish consumables. When continuing the shut down, the user presses OK button to continue the shut down as instructed. By displaying the screen 2104 before shutting down, for example, it is possible to prevent the supply unit 80 from shutting down without replenishing the consumables required for auto QC the next day.

On the device selection screen 2101, a desired device can be shut down simply by designating the device on the screen and pressing the OK button. Therefore, it is not necessary for the user to shut down each device, which is highly convenient. It is also convenient in that manual operation by the user such as using a cleaning agent rack including a rack bar code dedicated to the specific device is not required to supply the cleaning agent container 180 to the specific device.

Also, when shutting down the entire system, the user simply presses the OK button on the screen 2102. Therefore, it is not necessary for the user to shut down all the devices. Even when the specimen analysis system 1 is provided with a large number of devices, it is convenient because it is not necessary to manually prepare the cleaning agent container 180 necessary for cleaning all the devices.

FIG. 21 is an example of a QC specimen take-out screen 2200 displayed in response to selection of the take-out icon 2004 on the device status screen 2000. The screen 2200 includes the same QC specimen list as that included in the device status screen 2000, and a position selection button 2201. The user can select the position selection button 2201 corresponding to the position number of the QC specimen container 150 to be taken out while checking the QC specimen list, and select OK button at the bottom of the screen. A maximum of three position selection buttons 2201 can be selected at the same time, corresponding to a maximum of three containers that can be placed on the transfer holder 834. In the example of FIG. 21, the QC specimen containers 150 at position numbers 2, 6 and 7 are selected. As described with reference to FIG. 19, the QC specimen containers 150 at position numbers 1, 4 and 5 are in a state of being taken out from the cold insulation section 84 and cannot be taken out. Therefore, position selection buttons 2201 corresponding to these position numbers are non-selectable, and their check boxes are grayed out.

When the QC specimen container 150 to be taken out is selected by the position selection button 2201 and the OK button is pressed, the selected QC specimen container 150 is taken out from the cold insulation section 84, and set in the transfer holder 834 at the take-out position P5 (position shown in FIG. 10) of the charging section 83. Thereafter, the transfer holder 834 in which the QC specimen container 150 is set moves to the first charging port 831A (position shown in FIG. 9). When the transfer holder 834 moves to the first charging port 831A, the monitor 91 displays a notification screen 2210 notifying the user that the QC specimen container 150 (XN CHECK) has arrived at the first charging port 831A. The user can open the first cover 832A to take out the QC specimen container 150.

Figure 22:
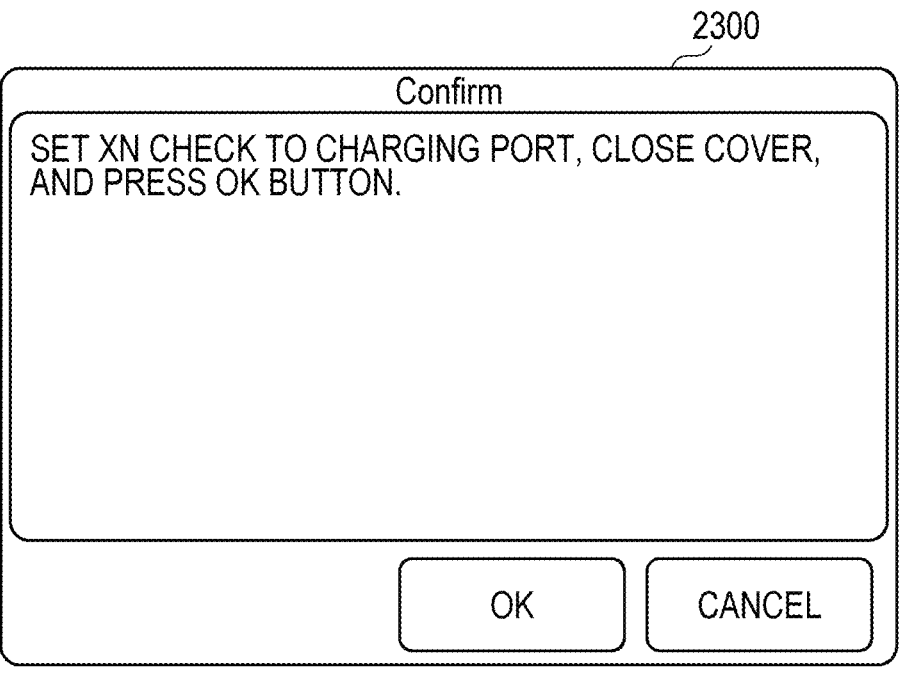
FIG. 22 is an example of a charging screen displayed when a charge icon on a device status screen is pressed.

FIG. 22 is an example of a charge screen 2300 displayed in response to selection of the charge icon 2005 on the device status screen 2000. When the charge icon 2005 is selected, the transfer holder 834 is positioned at the first charging port 831A, and the first cover 832A is unlocked. The screen 2300 is a screen for prompting the user to set the QC specimen container 150. For example, the screen 2300 is displayed on the monitor 91 at the timing when the first cover 832A is unlocked. When the user sets the QC specimen container 150 in the transfer holder 834 and presses OK button at the bottom of the screen, the QC specimen container 150 is transferred to the inside of the supply unit 80 and stored in the cold insulation section 84. This process will be described later.

Figure 23:
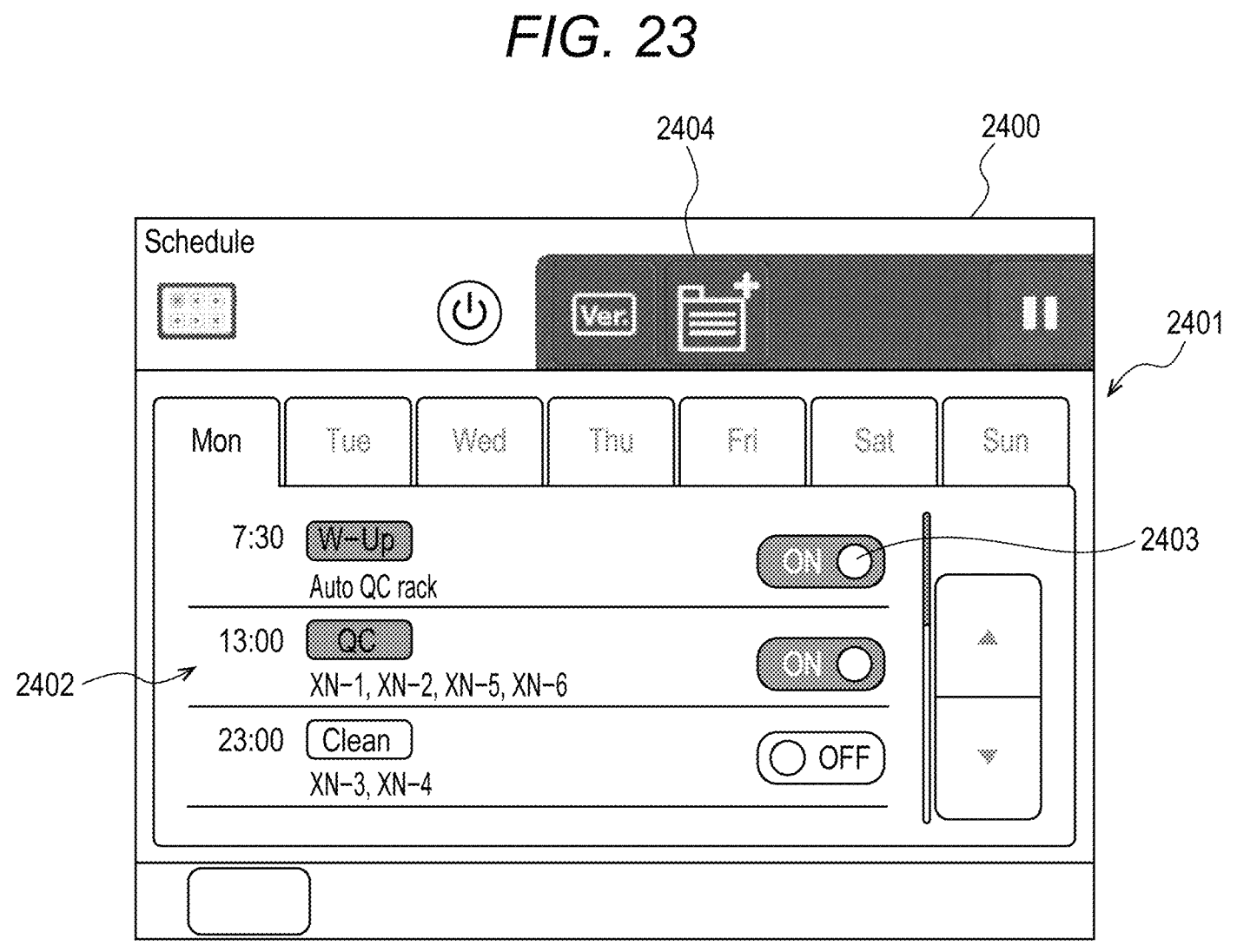

FIG. 23 is an example of a schedule screen 2400 displayed in response to selection of the schedule icon 1002 on the home screen 1000. The schedule screen 2400 includes seven days of the week tabs 2401 provided for each day of the week and a schedule list 2402 that displays schedules in a list. The day of the week tab 2401 selectably displays seven tabs that display seven names of the day of the week, Monday, Tuesday, Wednesday, Thursday, Friday, Saturday, and Sunday. The user can designate the day of the week for which the schedule is set by selecting any tab. Although FIG. 23 shows an example of registering a schedule for each day of the week, for example, the schedule may be registered by designating the date. For example, a weekly or monthly calendar may be displayed so that a schedule can be registered by designating a specific date on the calendar.

FIG. 23 illustrates a state where the Monday tab is selected. In the schedule list 2402, schedules to be executed on designated days of the week are displayed in chronological order. In the example of FIG. 23, wake up (auto start) is scheduled at 7:30 am on Monday, quality control measurement (auto QC) is scheduled at 13:00, and auto cleaning is scheduled at 23:00. A button 2403 for switching ON/OFF is provided corresponding to each schedule in the schedule list 2402. The user operates the button 2403 to set it to "ON" when executing the registered schedule. The user operates the button 2403 to set it to "OFF" when not executing the registered schedule. The schedule set to ON is automatically executed at the same time of day every week unless the schedule is set to OFF.

On a toolbar of the schedule screen 2400, a registration icon 2404 for registering a schedule is selectably displayed. The user presses the registration icon 2404 to add a new automatic execution schedule to the schedule list 2402.

Figure 24:
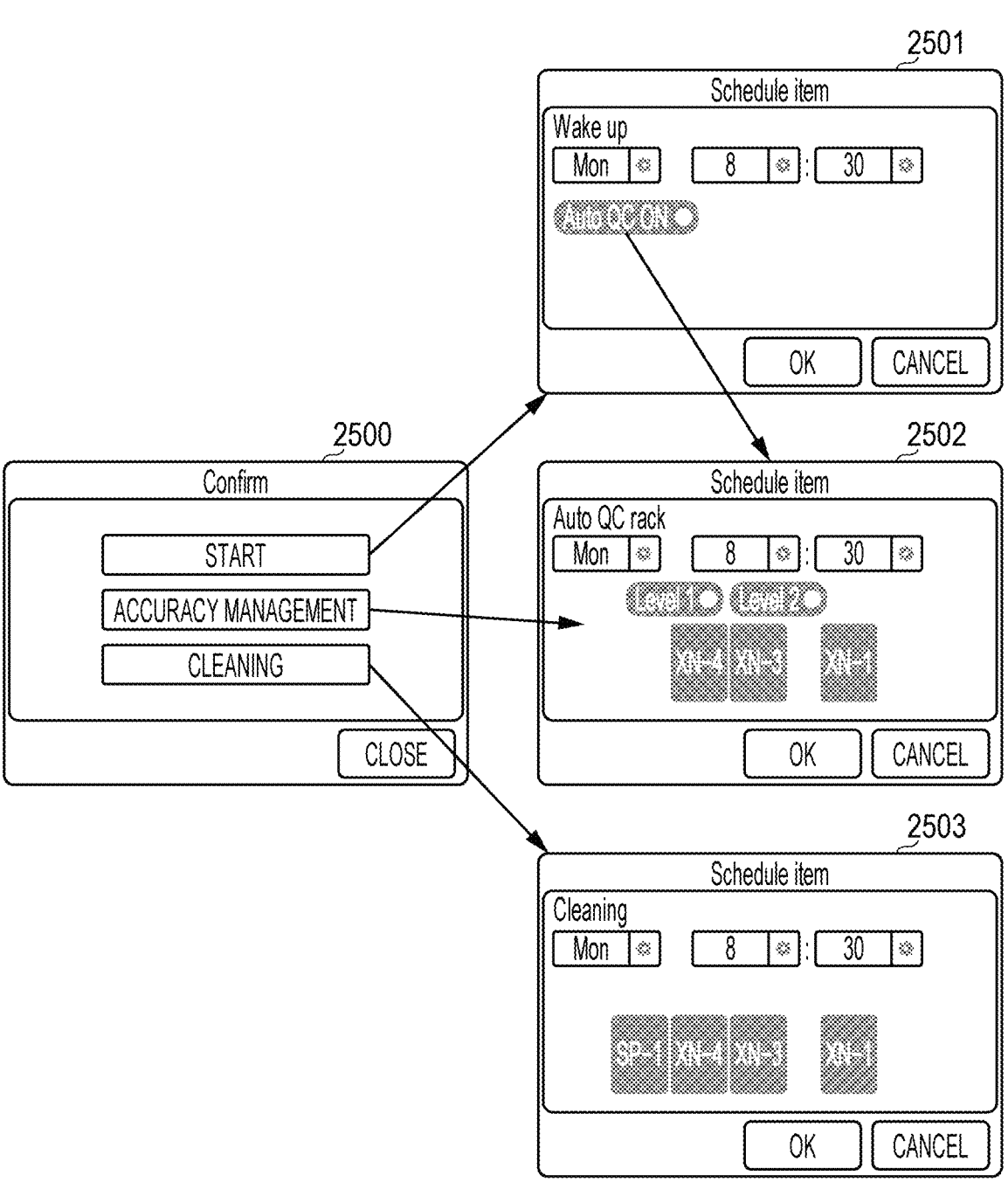
FIG. 24 is an example of a schedule registration screen displayed when a registration icon on a schedule screen is pressed.

FIG. 24 is an example of a schedule registration screen 2500 displayed in response to selection of the registration icon 2404 on the schedule screen 2400. The screen 2500 displays a menu for selecting the process to be automatically executed. In the example of FIG. 24, three menus, "START", "QUALITY CONTROL", and "CLEANING", are selectably displayed. In the present embodiment or embodiments, the registered schedule information is stored in the storage section of the control section 82*a*.

When the "START" menu on the schedule registration screen 2500 is selected, a registration screen 2501 is displayed. The screen 2501 is a screen for registering an auto wake up schedule. The screen 2501 includes multiple pull-down buttons for inputting the day of the week and time of day of the auto wake up. When a pull-down button of the day of the week is selected, a pull-down menu is displayed that includes seven days of the week, Monday, Tuesday, Wednesday, Thursday, Friday, Saturday, and Sunday, as choices. The user can select any day of the week. A pull-down of the time of day includes a pull-down button for designating the time of day by hour unit and a pull-down button for designating the time of day by minute unit. The user can designate the time of day by operating pull-down menus. In the example of FIG. 24, only the pull-down menus are illustrated, but a software keyboard may be displayed to receive input of numerical values from the user. The user can designate the day of the week and time of day to execute auto wake up by operating the screen 2501.

The registration screen 2501 further includes a button for turning on/off the execution of auto QC. The user operates the button to turn it "ON" when performing auto QC. The user operates the button to turn it "OFF" when not performing auto QC. The auto QC is an automatic quality control measurement using the QC specimen container 150 housed in the cold insulation section 84.

When an auto wake up schedule with auto QC set to ON is registered, one or a plurality of measurement unit(s) included in the specimen analysis system 1 are automatically started according to the schedule. Further, the QC specimen container 150 is automatically supplied to one or a plurality of the started measurement unit(s) to perform quality control measurement. When an auto wake up schedule with auto QC set to OFF is registered, a power supply of each unit of the specimen analysis system 1 is automatically turned on, but quality control measurement is not performed.

On the registration screen 2501, when the auto QC button is set to "ON" and "OK" button at the bottom of the screen is pressed, the screen transitions to a registration screen 2502. The registration screen 2502 is also displayed when the "QUALITY CONTROL" menu on the schedule registration screen 2500 is selected. In the specimen analysis system 1, the registration screen 2502 receives setting of the quality control measurement conditions (QC conditions)

from the user. As will be described in detail later, the specimen analysis system 1 determines one or a plurality of QC specimen container(s) 150 to be used for quality control measurement from among a plurality of QC specimen containers 150 stored in the cold insulation section 84, according to the QC conditions and the information on the QC specimen containers 150. The specimen analysis system 1 transports the determined QC specimen container(s) 150 to the measurement unit to measure the QC specimen.

The registration screen 2502 is a screen for creating an auto QC schedule. The screen 2502, like the screen 2501 described above, includes a plurality of pull-down buttons for designating the day of the week and time of day. Below the pull-down buttons, there are three concentration level buttons, "Level 1", "Level 2", and "Level 3", as buttons for selecting the type of QC specimen used in one auto QC. Below the concentration level buttons, a unit selection image for selecting the measurement unit for which quality control measurement is to be performed in auto QC is displayed. The unit selection image includes an image illustrating a plurality of units arranged according to a layout of the specimen analysis system 1.

The user sets the day of the week and time of day to execute auto QC on the registration screen 2502. The operation for setting the day of the week and time of day is as described above. The user operates the concentration level buttons to select the type of QC specimen to be used for auto QC. In the example of FIG. 24, level 1 and level 2 are designated as the concentration levels of the QC specimen. Level 3 is not designated and is off. The user selects a measurement unit for which quality control measurement is to be executed in auto QC from the unit selection image.

In FIG. 24, the measurement unit XN-1 arranged on the far right and the third and fourth measurement units XN-3 and XN-4 from the right are selected. In the setting example shown in FIG. 24, as the conditions for auto QC, quality control measurements using two QC specimen containers 150 in level 1 and level 2 are set for three measurement units, XN-1, XN-3, and XN-4, at 8:30 am on Monday. When "OK" button at the bottom of the screen 2502 is selected, a confirmation screen 2510 described later is displayed, and when confirmation operation is performed, the input schedule is registered in the list. In the present embodiment or embodiments, the registered conditions for auto QC are stored in the storage section of the control section 82*a*.

When the "CLEANING" menu on the schedule registration screen 2500 is selected, a registration screen 2503 is displayed. The screen 2503 is a screen for registering an auto cleaning schedule. The auto cleaning is an automatic cleaning of the measurement unit and the process unit using the cleaning agent container 180 stored in the second charging section 83B. The registration screen 2503 differs from the registration screen 2502 in not including concentration level buttons for selecting the type of QC specimen and in including a process unit 40 (SP-10), which is a smear preparation device, as a selectable unit. However, other than that, the registration screen 2503 has the similar configuration as the screen 2502.

The user operates pull-down buttons at the upper part of the screen to designate the day of the week and time of day to execute auto cleaning on the registration screen 2503. The user selects a unit selection image to designate a unit to be automatically cleaned. When "OK" button at the bottom of the registration screen 2503 is selected, the input schedule is registered in the schedule list through operations on a confirmation screen.

FIG. 25 is an example of the confirmation screen 2510 displayed when the auto QC schedule is input and the "OK" button is pressed on the registration screen 2502. As shown in FIG. 25, the confirmation screen 2510 displays the designated day of the week, time of day, and content to be automatically executed. When an auto QC schedule with a plurality of concentration levels designated is created on the registration screen 2502, a combination of the plurality of concentration levels is displayed as the content of the automatic execution schedule as shown in FIG. 25.

Figure 26:
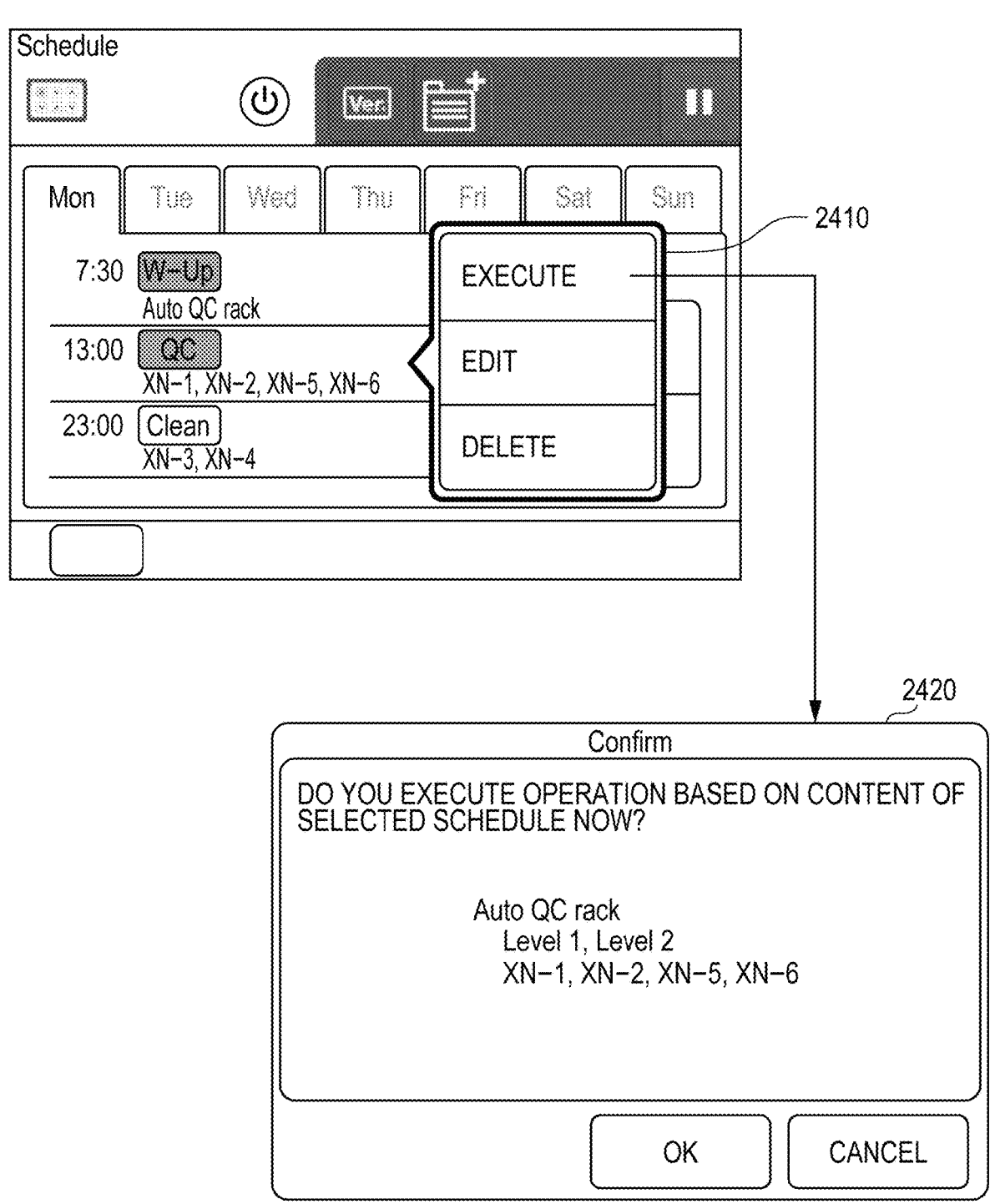
FIG. 26 is an example of an operation menu displayed when a schedule list on a schedule screen is pressed.

FIG. 26 illustrates an operation on the automatic execution schedule displayed in the schedule list from the schedule screen 2400 of FIG. 23. When the user selects an automatic execution schedule to be operated on the screen 2400, an operation menu 2410 is displayed. The operation menu 2410 includes three, "EXECUTE", "EDIT", and "DELETE".

The "EXECUTE" is used to execute the selected schedule earlier than the scheduled time. When the "EXECUTE" of the operation menu 2410 is pressed, a confirmation screen 2420 including the content of the scheduled automatic execution is displayed with a confirmation message "DO YOU EXECUTE CONTENT OF SELECTED SCHEDULE NOW?". When "OK" button is pressed on the confirmation screen 2420, quality control measurement is started according to the scheduled QC conditions. When the schedule is executed earlier than the scheduled time by operating the "EXECUTE" menu, the schedule will not be executed at the originally scheduled time.

The "EDIT" is used to change the content of the schedule that has already been registered. For example, the "EDIT" is used when changing the time to execute auto QC, or when changing the concentration level to be used in auto QC or the object unit for quality control measurement. When the "EDIT" is pressed, the same screen as any of the screens 2501, 2502 and 2503 shown in FIG. 24 is displayed according to the type of schedule to be edited, and editing is possible via the screen. When editing is performed, the content of the schedule list is updated based on the edited content.

The "DELETE" is used to delete the schedule that has already been registered. When deleted, the target schedule is deleted from the schedule list.

FIG. 27 is an example of the portal screen 2600. The portal screen 2600 includes a schedule display area 2601 that displays a list of schedules planned for the current day, and an inventory display area 2602 that displays the inventory status of consumables stored by the supply unit 80. As the contents displayed in the schedule display area 2601, among the automatic execution schedules registered on the schedule registration screen 2500, the planned schedules corresponding to the day of the week of the operation date are displayed in a list in chronological order from the top.

In the inventory display area 2602, the inventory status of consumables stored by the supply unit 80 is displayed by graph. In the example of FIG. 27, remaining amounts of a plurality of types of consumables are displayed as a bar graph on a horizontal axis in which future dates are arranged to the right starting from the current time point. The bar graph displays how long the consumables will be sufficient when the registered schedule is executed as scheduled using the inventory of consumables stored in the supply unit 80. In the example of FIG. 27, a bar graph showing inventories of the QC specimen containers 150 at concentration levels 1, 2 and 3 and the cleaning agent container (CCA) 180 is displayed. Below the graph, a message about the inventory of consumables is displayed. For example, when the number of empty racks 170 stored in the rack housing section 88 falls below a predetermined number, for example, a message "EMPTY RACK: REPLENISHABLE" is displayed as shown in FIG. 27. The message also includes an alert prompting the user to replenish the consumables when the consumables required to execute the scheduled automatic execution schedule are insufficient. For example, in FIG. 27, when the number of remaining tests for QC specimens at concentration level 3 is insufficient for the auto QC schedule planned for the next day, it is displayed as "L3: NUMBER OF TESTS REQUIRED FOR AUTO QC TOMORROW IS INSUFFICIENT. PLEASE REPLENISH." For example, the automatic execution schedule to be alerted may be the one scheduled for the current day, the next day, or the next working day, or may be the auto start schedule planned next. By checking the alert, the user can replenish the consumables in advance. In FIG. 27, dates on which the schedule can be executed within range of the inventory of consumables are displayed by a bar graph, but display format does not have to be a graph, and only the dates may be displayed. The display is not limited to the date, and the number of remaining days or the remaining number of times that the schedule can be executed based on the inventory may be displayed by numerical values or graph.

FIG. 28 is a block diagram showing a configuration of the supply unit 80, also showing a connection relationship between the supply unit 80, the modules 10, and the transport controller 70. The control section 82a is connected to devices of the charging section 83, the cold insulation section 84, the transfer section 85, the heating section 86, the information reading section 87, and the rack housing section 88. The control section 82a sends a control signal to these devices to control an action of each device. In the present embodiment or embodiments, among the processes related to the quality control measurement, the process performed by the storage adjustment unit 82 is executed under control of the control section 82a. The transport of the QC specimen rack 160 by the transport unit 20 of the conveyor section 81 and the module 10 is mainly executed under control of the transport controller 70. The measurement of the quality control material in the measurement unit is executed under control of the control unit 30.

The control section 82a, like the control section 31 of the control unit 30 and the control section 71 of the transport controller 70, is composed of a computer. The control section 82a includes a processor, a storage section, an input/output port, and the like. In the control section 82a, for example, a control program for executing processes such as cooling storage, transfer, and heating of the QC specimen container 150 is installed. The control section 82a also stores the database 820 that stores information on quality control specimens. As described above, the database 820 is information on each QC specimen container 150 associated with the position number of the housing portion 841b of the cold insulation section 84.

The control section 31 of the control unit 30 stores a database 310 about the results of quality control measurement. The database 310 stores QC files, which are measurement results of the QC specimens, for each measurement date and time, and for each concentration level and lot of the QC specimens. FIG. 49 illustrated later shows an example of the QC file stored in the database 310. With this database 310, the user can check, for example, the state of the measurement unit, a lot-to-lot difference of QC specimens described later, and the like.

FIG. 29 is an example of the database 820 stored in the control section 82a. The database 820 includes attribute information and remaining amount information of each QC specimen container 150 housed in the cold insulation section 84. The attribute information preferably includes at least one of the concentration level, lot information, and expiration date of the QC specimen. In the example of FIG. 29, in order from the leftmost column, a first column showing the position number of the housing portion 841*b* of the cold insulation section 84, a second column showing the concentration level of the QC specimen container 150, a third column showing the lot number, a fourth column showing the number of remaining tests, which is the remaining amount information, and a fifth column showing the expiration date. Based on this database 820, the QC specimen list 2001A described above is created to determine one or a plurality of QC specimen container(s) 150 to be used for quality control measurement.

Hereinafter, an example of processes related to auto QC and auto cleaning of the specimen analysis system 1 will be described in detail with reference to FIGS. 30, 31, 32, 33, 34, 35, 36, 37, 38, 39, 40, and 41. The processes related to auto QC and auto cleaning are mainly executed by functions of the control section 31 of the control unit 30 and the control section 82*a* of the supply unit 80. In the following, FIGS. 42, 43, 44, and 45 showing an action of the supply unit 80 will be referred to as appropriate.

Figure 30:
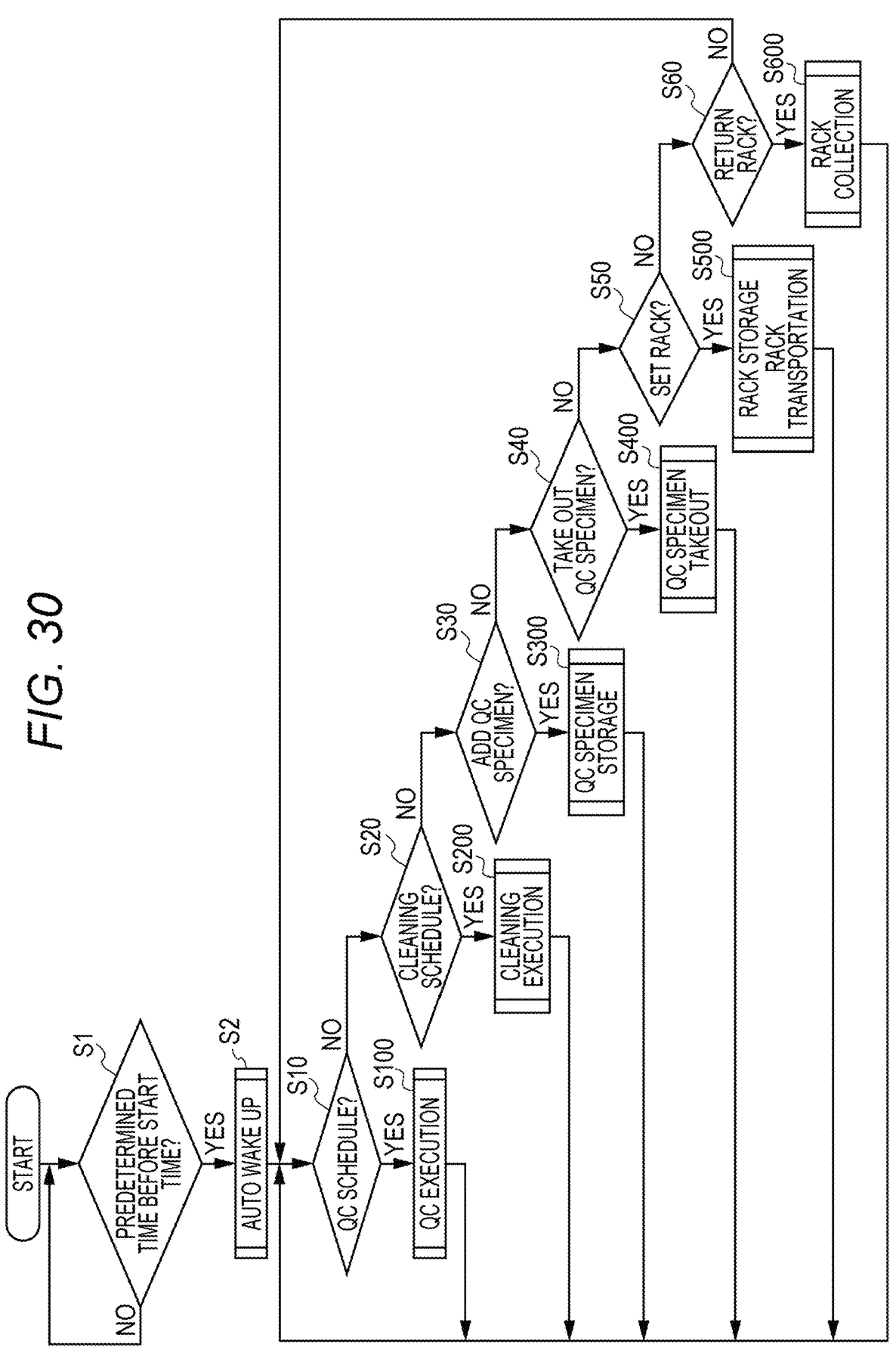
FIG. 30 is a flowchart showing a series of processes of a specimen analysis system.

FIG. 30 is a flowchart showing a series of processes of the specimen analysis system 1. The processes of FIG. 30 are executed by the control section 82*a* of the supply unit 80. When the auto wake up schedule is registered, the control section 82*a* determines whether or not the current time has become before a predetermined time of the designated time (step S1). When the current time has become before the predetermined time of the designated time, the control section 82*a* executes auto wake up (step S2). The process of S2 will be described later with reference to FIG. 31.

When the power of each unit constituting the system is turned on by the auto wake up, the control section 82*a* determines whether or not the scheduled time for auto QC has come (step S10). This determination is made based on the registration information of the auto QC schedule stored in the control section 82*a*. When the control section 82*a* determines that the time for auto QC has come, the control section 82*a* starts quality control measurement using the QC specimen container 150 (step S100). The process of S100 will be described later with reference to FIG. 32.

When NO in step S10, the control section 82*a* determines whether or not the scheduled time for auto cleaning has come (step S20). This determination is made based on the registration information of the auto cleaning schedule stored in the control section 82*a*. When the control section 82*a* determines that the time for auto cleaning has come, the control section 82*a* starts auto cleaning using the cleaning agent container 180 (step S200). The process of S200 will be described later with reference to FIG. 34.

When NO in step S20, the control section 82*a* determines whether or not the addition of the QC specimen container 150 has been instructed by the user (step S30). For example, the control section 82*a* determines whether or not the charge icon 2005 on the device status screen 2000 of FIG. 19 has been operated. When the charge icon 2005 has been operated (YES in step S30), the control section 82*a* performs a process of storing the QC specimen container 150 in the cold insulation section 84 (step S300). The process of S300 will be described later with reference to FIG. 35.

When NO in step S30, the control section 82*a* determines whether or not the removal of the QC specimen container 150 has been instructed by the user (step S40). For example, the control section 82*a* determines whether or not the take-out icon 2004 on the device status screen 2000 of FIG. 19 has been operated. When the take-out icon 2004 has been operated (YES in step S40), the control section 82*a* performs a process of taking out the QC specimen container 150 from the cold insulation section 84 (step S400). The process of S400 will be described later with reference to FIG. 36.

When NO in step S40, the control section 82*a* determines whether or not the rack has been set on the conveyor section 81 of the supply unit 80 (step S50). When the control section 82*a* determines that the rack has been set (YES in step S50), the control section 82*a* performs a process of rack storage or rack transport according to the type of rack (step S500). The process of S500 will be described later with reference to FIG. 40.

When NO in step S50, the control section 82*a* determines whether or not the rack sent out from the supply unit 80 has returned to the conveyor section 81 (step S60). When the control section 82*a* determines that the rack has returned (YES in step S60), the control section 82*a* performs a predetermined collection process according to the type of rack (step S600). The process of S600 will be described later with reference to FIG. 41.

FIGS. 31, 32, 33, 34, 35, 36, 40 and 41 are flowcharts showing an action of the supply unit 80.

Figure 31:
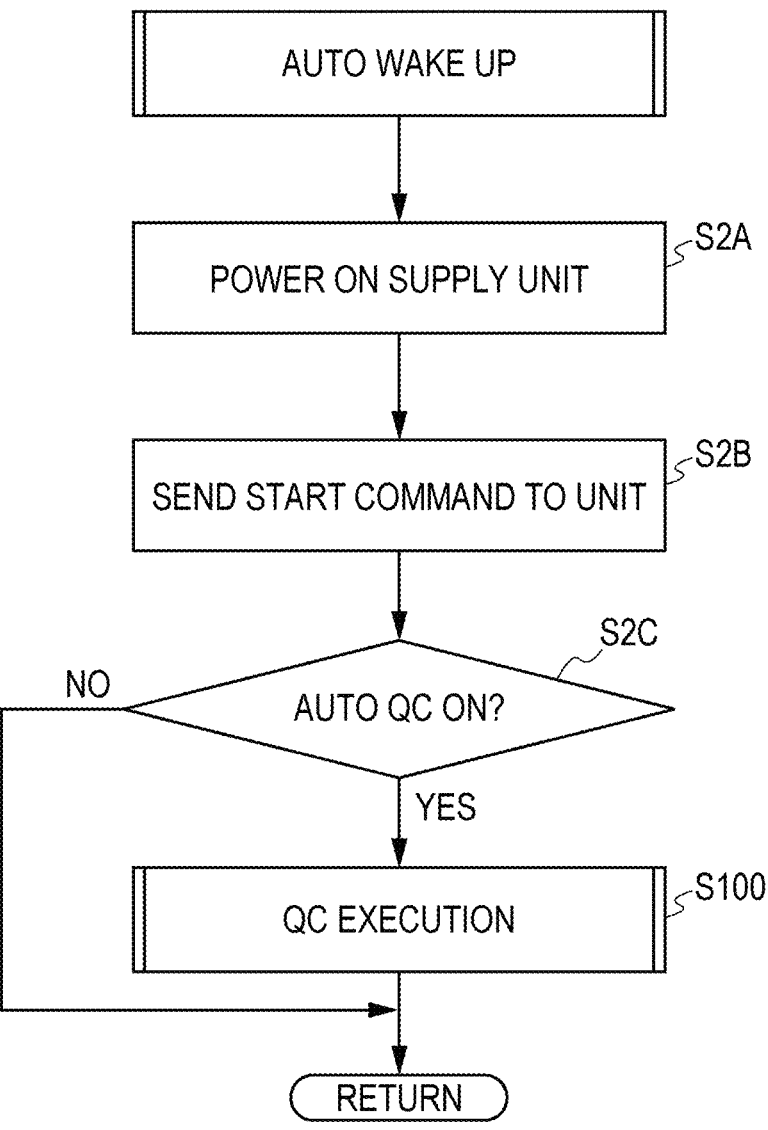
FIG. 31 is a flowchart showing a process procedure of auto wake up.

FIG. 31 is a flowchart showing the auto wake up process. In step S2A, the control section 82*a* turns on the power supply of the supply unit 80. As a result, the supply of electric power to the heater of the heating section 86 is started, and the temperature is raised until the temperature inside the heating section 86 reaches the set temperature (23° C.). In step S2B, the control section 82*a* sends a start command to each unit of the specimen analysis system 1 when the current time has become before the predetermined time of the designated time. As a result, the power supply of all the units constituting the specimen analysis system 1 is turned on. The screen 2502 in FIG. 24 may be configured so that a unit for auto wake up can be designated and a start command is sent only to the designated unit based on the registration information of the schedule.

The predetermined time is preferably longer than a time required to heat the QC specimen container 150 stored in the cold insulation section 84 until the temperature reaches a temperature measurable by the heating section 86 (hereinafter, heating time). For example, when the heating time is 10 minutes, the predetermined time is preferably at least 10 minutes or more. More preferably, the predetermined time includes, in addition to the heating time, a time required to measure the heated QC specimen by the measurement unit and obtain the measurement result. In one example, the predetermined time is, for example, 30 minutes. That is, when the wake up time is set to 8:30, the control section 82*a* sends a start command at 8:00. By doing this, the user can complete from heating to measurement of the QC specimen at the designated time as the wake up time, and the user can immediately start an test using the measurement unit at the designated time. The predetermined time may be fixed or variable depending on the presence or absence of auto QC and QC conditions.

In step S2C, the control section 82*a* determines whether or not the auto QC is set to ON. When the auto QC is set to ON as shown in the screen 2501 in FIG. 24, the control section 82*a* executes the auto QC in step S100 following the auto wake up. That is, when the auto wake up schedule with auto QC set to ON is registered, the power supply of each unit of the specimen analysis system 1 is automatically turned on at the designated time on the designated day of the week, and quality control measurement using the QC specimen container 150 is automatically started. When the auto QC is set to OFF, only auto wake up is executed and quality control measurement is not performed.

Figure 32:
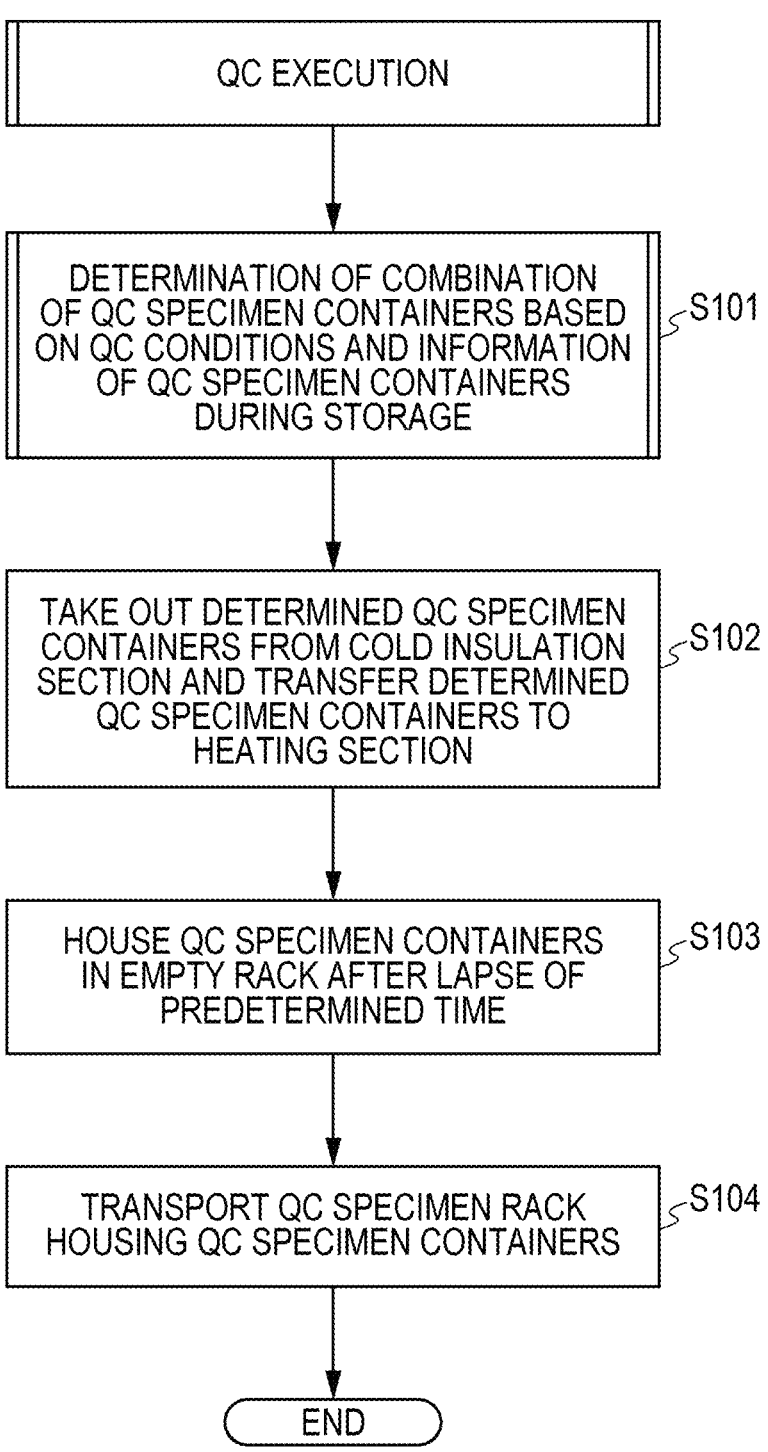
FIG. 32 is a flowchart showing a process procedure of auto QC in a supply unit.

FIG. 32 is a flowchart showing a process of auto QC in the supply unit 80 (step S100 in FIG. 30). The procedure shown in this flowchart is applied not only to the auto QC executed following the auto wake up, but also to auto QC executed at a timing other than the wake up. In step S101, the control section 82a determines a combination of the QC specimen containers 150 to be used for quality control measurement, based on the quality control measurement conditions (QC conditions) and the information on the QC specimens in storage.

One QC specimen container 150 may be used for quality control measurement, but generally, two or more QC specimen containers 150 with different concentration levels of QC specimens are used.

The QC conditions include designation of one or a plurality of measurement unit(s) to perform quality control measurement. When one or a plurality of measurement unit(s) to perform quality control measurement are designated, the control section 82a determines one or a plurality of QC specimen container(s) 150 to be used according to the number of the designated measurement unit(s). The information on the QC specimens includes information on the type of QC specimens, and the QC conditions include designation of the type of QC specimens to be used. The control section 82a determines one or a plurality of QC specimen container(s) 150 to be used, based on the designated type of QC specimens and the information on the type of QC specimens.

The QC conditions may include designation of a plurality of concentration levels as the type of QC specimens, designation of lots of QC specimens to be used, and the like. The control section 82a determines a combination of a plurality of QC specimen containers 150, for example, based on a plurality of designated concentration levels. One or a plurality of QC specimen container(s) 150 are determined based on the designated lots and the lot information of the QC specimens. The information on the QC specimens may include the remaining amount information of the QC specimen in each QC specimen container 150, and one or a plurality of QC specimen container(s) 150 may be determined based on the number of designated measurement units and the remaining amount information.

As will be described in detail later, when the remaining amount of a first QC specimen container 150 to be used for quality control measurement is less than the number of tests performed based on the number of designated measurement units, a combination of the first QC specimen container 150 and a second QC specimen container 150 is determined as the containers to be used. In this case, a container with the same concentration level as the first QC specimen container 150 is selected as the second QC specimen container 150. The remaining amount of the QC specimen container 150 is determined, for example, based on at least the concentration levels and lot information of the QC specimens and the QC conditions.

As described above, the information on the QC specimens includes the attribute information and the remaining amount information of each QC specimen. Examples of the attribute information include the concentration level, lot information, and expiration date of the QC specimen. The remaining amount information is, for example, the number of usable times of the QC specimen. The information on the QC specimens is stored in the storage section of the control section 82a as the database 820. Similarly, the QC conditions are also stored in the storage section.

In step S102, the control section 82a controls to take out the QC specimen container 150 from the cold insulation section 84, and the control section 82a transfers the QC specimen container 150 to the heating section 86. Specifically, the control section 82a controls the cold insulation section 84 to open the cover 842. The control section 82a controls the transfer section 85 to take out the QC specimen container 150 determined in S101 from the cold insulation section 84. The control section 82a stores the information on the QC specimen container 150 in the database 820 in association with the position numbers of nine housing portions 841b in the cold insulation section 84. The control section 82a controls the transfer section 85 so as to take out the container from the housing portion 841b corresponding to the position number of the determined QC specimen container 150 and set the container in the heating section 86. The control section 82a starts time measurement when the QC specimen container 150 is set in the heating section 86.

In step S103, when a predetermined time elapses after the QC specimen container 150 is set in the heating section 86, the control section 82a transfers the QC specimen container 150 temperature-controlled to the measurement temperature from the heating section 86 to the empty rack 170 of the rack housing section 88. The control section 82a controls the transfer section 85 to house the QC specimen container 150 in the empty rack 170.

When a plurality of QC specimen containers 150 are used for quality control measurement, each QC specimen container 150 is housed in an empty rack 170 based on the conditions for auto QC stored in the storage section.

In step S104, the control section 82a controls to transport the QC specimen rack 160 housing the QC specimen container 150 from the supply unit 80. The control section 82a controls the rack housing section 88 to send out the QC specimen rack 160 to the second transport path 812 of the conveyor section 81. The control section 82a controls the conveyor section 81, to transport the QC specimen rack 160 from the supply unit 80 through the third transport path 813 and the fourth transport path 814. The control section 82a notifies the control section 71 of the transport controller 70 of the measurement unit serving as a destination of the QC specimen rack 160. The control section 71 of the transport controller 70 controls each transport unit 20 so that the QC specimen rack 160 is transported to the notified measurement unit.

FIGS. 42A, 42B, and 42C are diagrams showing an action of the supply unit 80 in steps S102 to S104 in FIG. 32. As shown in FIG. 42A, under the control of the control section 82a, the transfer section 85 takes out the QC specimen container 150 from the housing portion 841b of the cold insulation chamber 841a. The transfer section 85 stores the QC specimen container 150 in the housing portion 86b of the heating section 86. Thereafter, when a predetermined time elapses after the QC specimen container 150 is transferred to the heating section 86, the transfer section 85 transfers the QC specimen container 150 to the empty rack 170 of the rack housing section 88, as shown in FIG. 42B.

When the QC specimen containers 150 of the number required for quality control measurement are housed in the housing portion 111 of the empty rack 170 (front end rack), the rack housing section 88 sends out the QC specimen rack 160, which is the front end rack in which the QC specimen containers 150 are housed, is sent out to the second transport path 812 of the conveyor section 81, as shown in FIG. 42C. The QC specimen rack 160 is transported from the supply unit 80 through the third transport path 813 and the fourth transport path 814 of the conveyor section 81.

Figure 33:
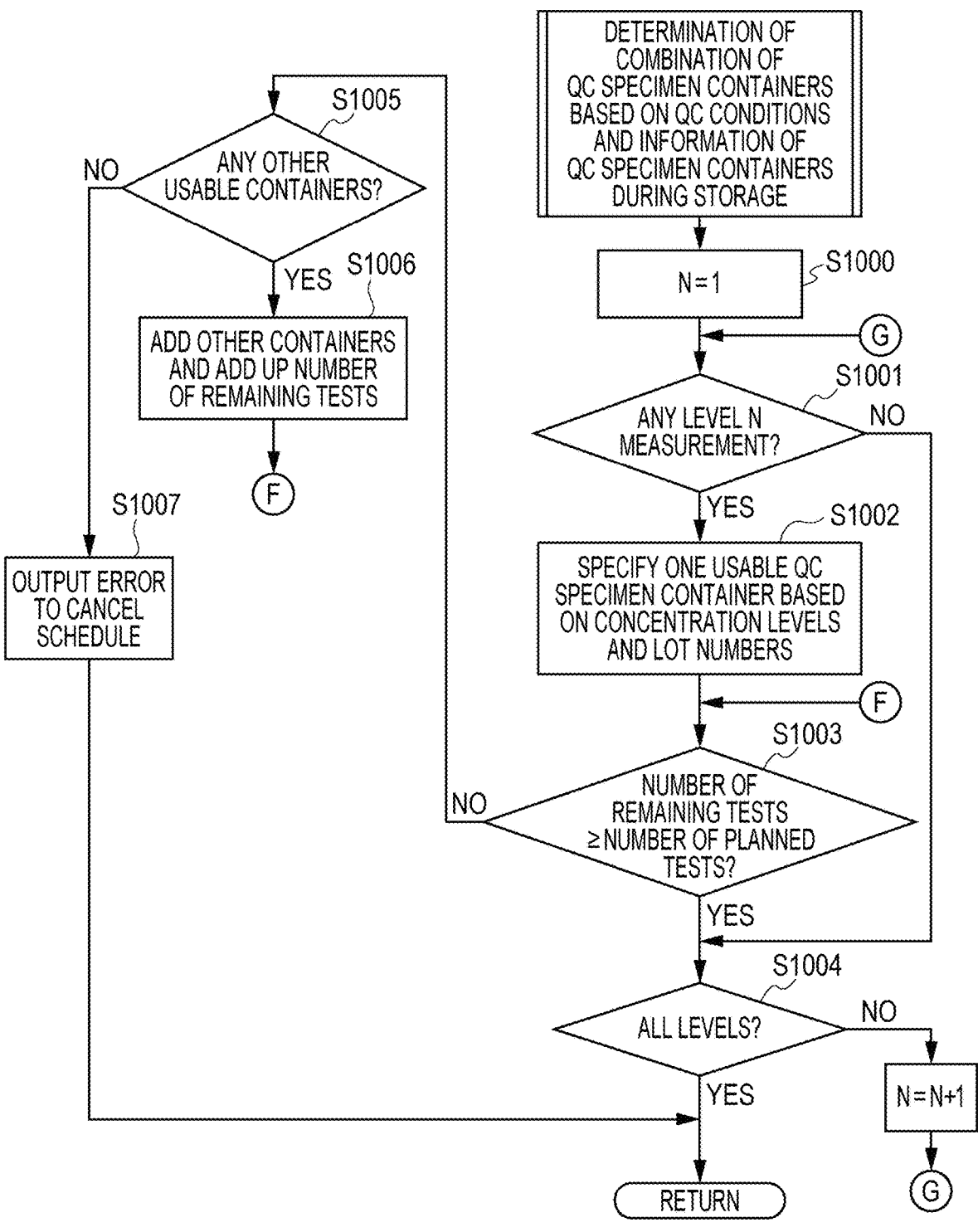
FIG. 33 is a flowchart showing a process procedure for determining a combination of QC specimen containers to be used for quality control measurement in auto QC.

FIG. 33 is a flowchart showing a specific example of a process for determining the combination of the QC specimen containers 150 to be used for quality control measurement (step S101 in FIG. 32). In step S1000, the control section 82*a* sets variable N regarding the concentration level to 1. In step S1001, the control section 82*a* determines whether or not measurement of a QC specimen at concentration level N is necessary. When the variable N is 1, necessity of measuring the QC specimen at concentration level 1 is determined.

The determination in step S1001 is made based on the designation of the concentration level of the QC conditions stored in the storage section. For example, when the QC conditions include the measurement of the QC specimen at concentration level 1 as shown in screen 2502 in FIG. 24, it is determined as YES in step S1001. When the measurement of the QC specimen at concentration level 1 is not designated, steps S1002 and S1003 are skipped and the process proceeds to step S1004.

In step S1002, the control section 82*a* specifies one QC specimen container 150 from the QC specimen containers 150 stored in the cold insulation section 84, based on the concentration levels and lot numbers registered in the database 820. For example, a usable QC specimen container 150 is specified from among the QC specimen containers 150 with the same lot number as the lot number of the QC specimen container 150 at concentration level 1 in operation. When there are a plurality of QC specimen containers 150 with the same lot number, the one with the smallest number of remaining tests is specified.

In step S1003, the control section 82*a* determines whether or not the number of remaining tests of the specified QC specimen container 150 is equal to or greater than the number of tests for quality control measurement. This determination is made based on the information on the number of remaining tests of the QC specimen container 150 registered in the database 820. That is, the number of remaining tests of the specified QC specimen container 150 is compared with the number of tests to be performed for quality control measurement to be performed, and when the number of remaining tests is equal to or greater than the number of tests to be performed, it is determined as YES.

In step S1004, the control section 82*a* determines whether or not the QC specimen containers 150 of all concentration levels required for quality control measurement have been specified. This determination is made based on the designation of the concentration level of the QC conditions stored in the storage section. For example, when the measurement of concentration levels 1 and 2 is designated by the QC conditions, steps S1001 to S1003 are executed for concentration level 2.

When the control section 82*a* determines NO in step S1003, that is, when the number of remaining tests of the specified QC specimen container 150 is less than the number of tests to be performed, in step 1005, whether or not other usable QC specimen containers 150 with the same concentration level are stored in the cold insulation section 84. This determination is made based on database 820. When other usable QC specimen containers 150 with the same concentration level are stored (YES in step S1005), the control section 82*a* adds the number of remaining tests of the other QC specimen containers 150 to the number of remaining tests of the QC specimen container 150 previously specified (step S1006). Then, the process returns to step S1003 again, and whether or not the total number of remaining tests is equal to or greater than the number of tests to be performed is determined.

The procedure of steps S1003, S1005 and S1006 is repeated until it is determined as YES in step S1003. When other usable QC specimen containers 150 with the same concentration level are not stored in the cold insulation section 84 (NO in step S1005), the control section 82*a* outputs an auto QC error in step S1007 to cancel the auto QC schedule. The auto QC error is information output when the stored QC specimen is insufficient for the registered auto QC schedule. Notification of the auto QC error is displayed, for example, on the monitor 91. In this case, the user needs to set the QC specimen container 150 at concentration level 1 in the supply unit 80.

Figure 34:
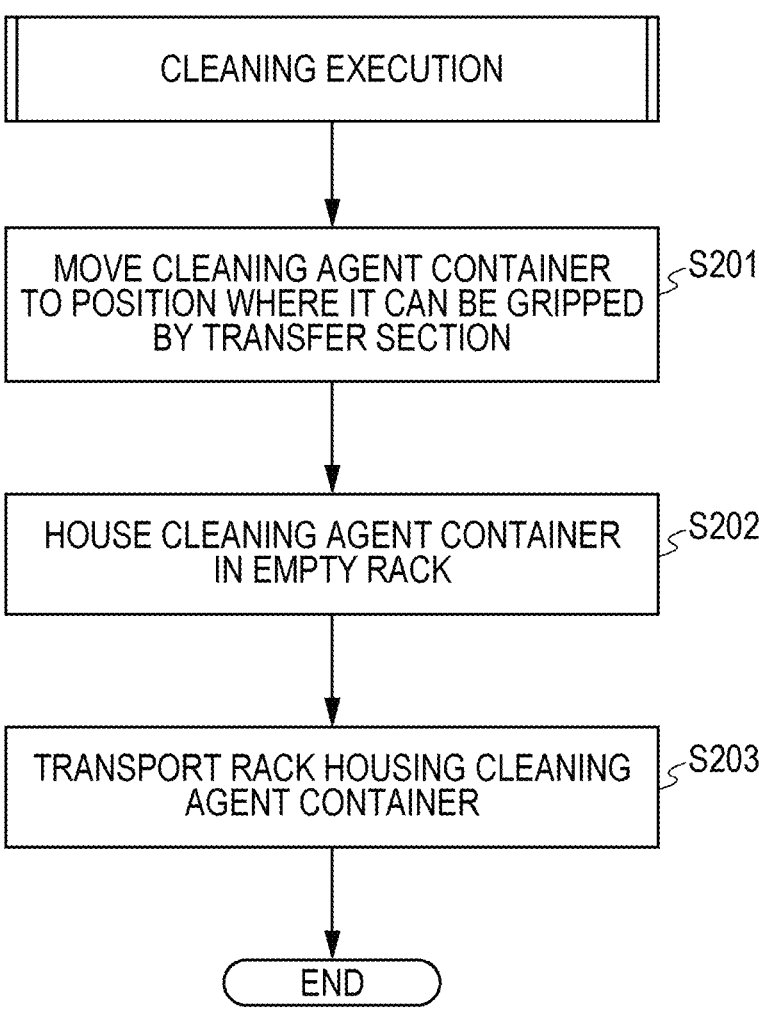
FIG. 34 is a flowchart showing a process procedure of auto cleaning in a supply unit.

FIG. 34 is a flowchart showing a process of auto cleaning in the supply unit 80 (step S200 in FIG. 30). The auto cleaning is performed based on the auto cleaning schedule, and the cleaning agent rack housing a cleaning agent is transported to the unit designated in the schedule. In step S201, the control section 82*a* controls the cleaning agent container 180 stored in the second charging section 83B so as to move the cleaning agent container 180 to a position where the cleaning agent container 180 can be gripped by the transfer section 85. The control section 82*a* controls the take-out section 839 of the second charging section 83B so that the cleaning agent container 180 can be gripped by the transfer section 85.

The control section 82*a* controls in step S202 to transfer the cleaning agent container 180 to the empty rack 170 of the rack housing section 88. The control section 82*a* controls in step S203 to transport the cleaning agent rack housing the cleaning agent container 180 from the supply unit 80.

Figure 43A:
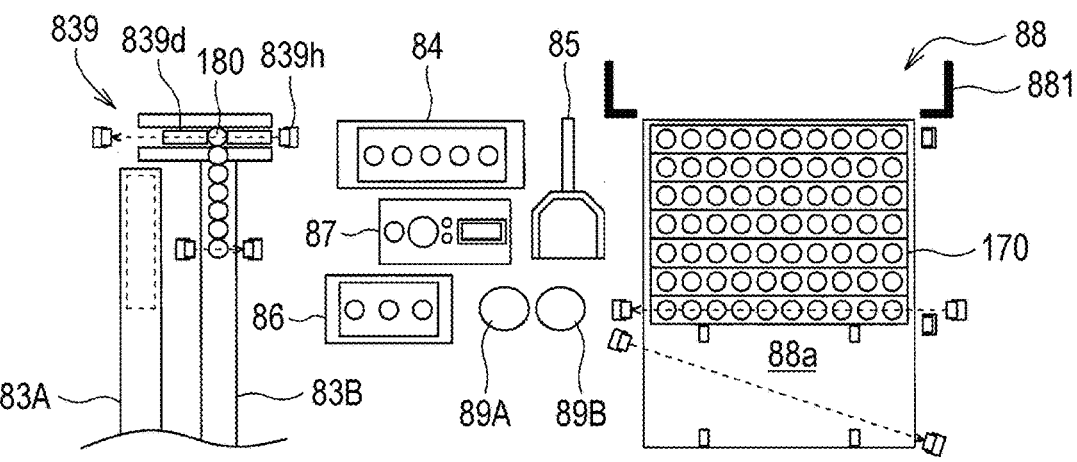
FIGS. 43A, 43B, and 43C are diagrams showing actions of a supply unit in auto cleaning.
Figure 43B:
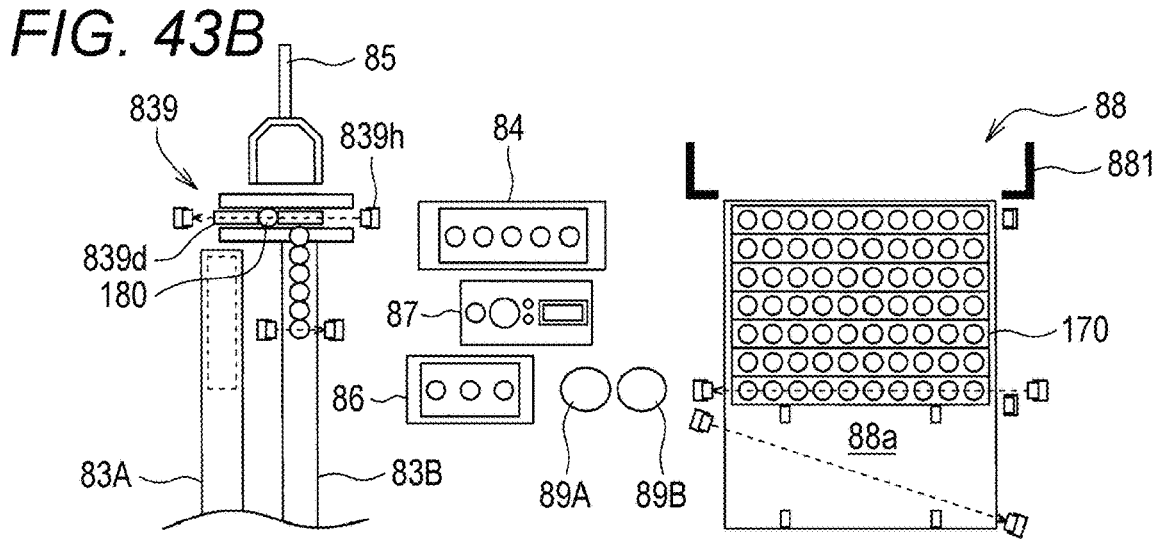

FIGS. 43A, 43B, and 43D are diagrams showing an action of the supply unit 80 in steps S201 to S203 in FIG. 34. The cleaning agent container 180 is transferred from the second charging port 831B (see FIG. 9 and the like) to the take-out section 839 accessible by the transfer section 85 by the second charging section 83B. However, when the transfer plate 839*d* is located on the right end side of the take-out section 839, as shown in FIG. 43A, the transfer section 85 cannot grip the cleaning agent container 180. Therefore, as shown in FIG. 43B, the transfer plate 839*d* housing the cleaning agent container 180 is moved to the left end side of the take-out section 839.

Figure 43C:
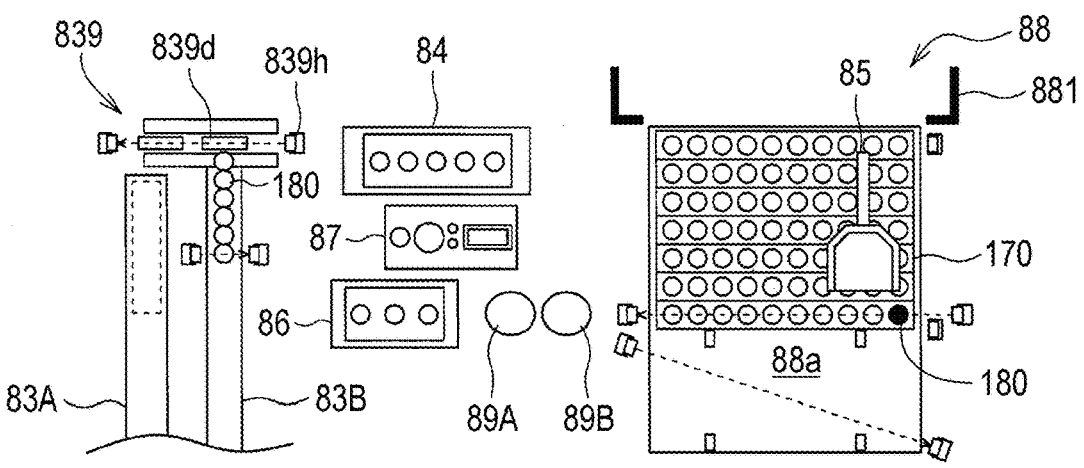

As a result, the lower end of the cleaning agent container 180 abuts on the upper surface of the inclined block 839*c* (see FIG. 9 and the like) arranged below the transfer plate 839*d*, and the cleaning agent container 180 is pushed up so that the cleaning agent container 180 can be gripped by the transfer section 85. At this time, the pushed-up cleaning agent container 180 is detected by the sensor 839*h*. When the cleaning agent container 180 is detected by the sensor 839*h*, the transfer section 85 takes out the cleaning agent container 180 from the take-out section 839, and the transfer section 85 transfers the cleaning agent container 180 to the empty rack 170, as shown in FIG. 43C. Similar to the QC specimen container 150, the cleaning agent container 180 of the number required for cleaning is transferred from the take-out section 839, and the cleaning agent container 180 is housed in the front end rack of the rack housing section 88. Similar to the QC specimen rack 160, the cleaning agent rack housing the cleaning agent container 180 is transported from the supply unit 80 toward the measurement unit, from the rack housing section 88 through the second transport path 812, the third transport path 813, and the fourth transport path 814 of the conveyor section 81.

Figure 35:
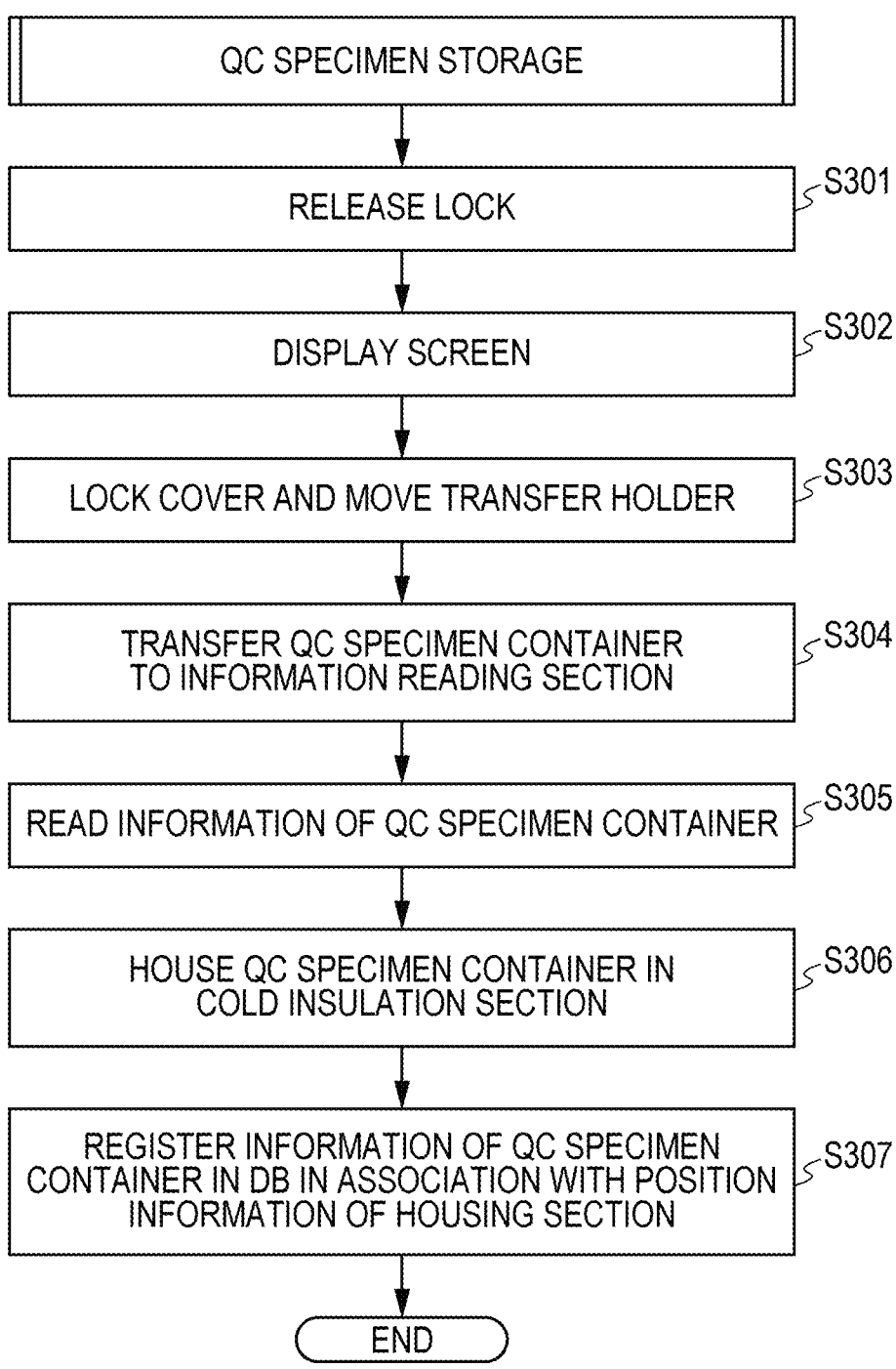
FIG. 35 is a flowchart showing a procedure of a process for storing a QC specimen container in a cold insulation section of a supply unit.

FIG. 35 is a flowchart showing a process of storing the QC specimen container 150 in the cold insulation section 84 of the supply unit 80 (step S300 in FIG. 30). As described above, the process of FIG. 35 is executed when the user operates the charge icon 2005 on the device status screen 2000. In step S301, the control section 82a controls a lock mechanism for the first cover 832A of the first charging section 83A to unlock the first cover 832A. When the first cover 832A is unlocked, in step S302, the control section 82a displays a screen prompting to set the QC specimen container 150. An example of this screen is the charge screen 2300 in FIG. 22, which is displayed on the monitor 91.

In step S303, the control section 82a controls to lock the first cover 832A when the QC specimen container 150 is set in the transfer holder 834, the first cover 832A is closed, and the OK button on the charge screen 2300 is pressed. The control section 82a controls the transfer holder 834 to transfer the QC specimen container 150 to the inside of the storage adjustment unit 82. At this time, the transfer holder 834 moves to the take-out position P5 of the first charging section 83A. In step S304, the control section 82a controls the transfer section 85 to transfer the QC specimen container 150 from the take-out position P5 to the information reading section 87. In step S305, the information reading section 87 reads the information on the QC specimen container 150 under the control of the control section 82a.

In step S306, the control section 82a controls the transfer section 85 to transfer the QC specimen container 150 from the information reading section 87 to the cold insulation section 84. Under the control of the control section 82a, the transfer section 85 houses the QC specimen container 150 in the housing portion 841b of the cold insulation chamber 841a. In step S307, the control section 82a registers the information on the QC specimen container 150 acquired by the information reading section 87 in the database 820 in association with the position number of the housing portion 841b housing the QC specimen container 150. When the information reading section 87 acquires the information, a housing position of the QC specimen container 150 in the cold insulation section 84 may be determined. In that case, when the information reading section 87 acquires the information and transmits the information to the control section 82a, the information on the QC specimen container 150 may be registered in the database 820 in association with the position number of the housing portion 841b.

Figure 44A:
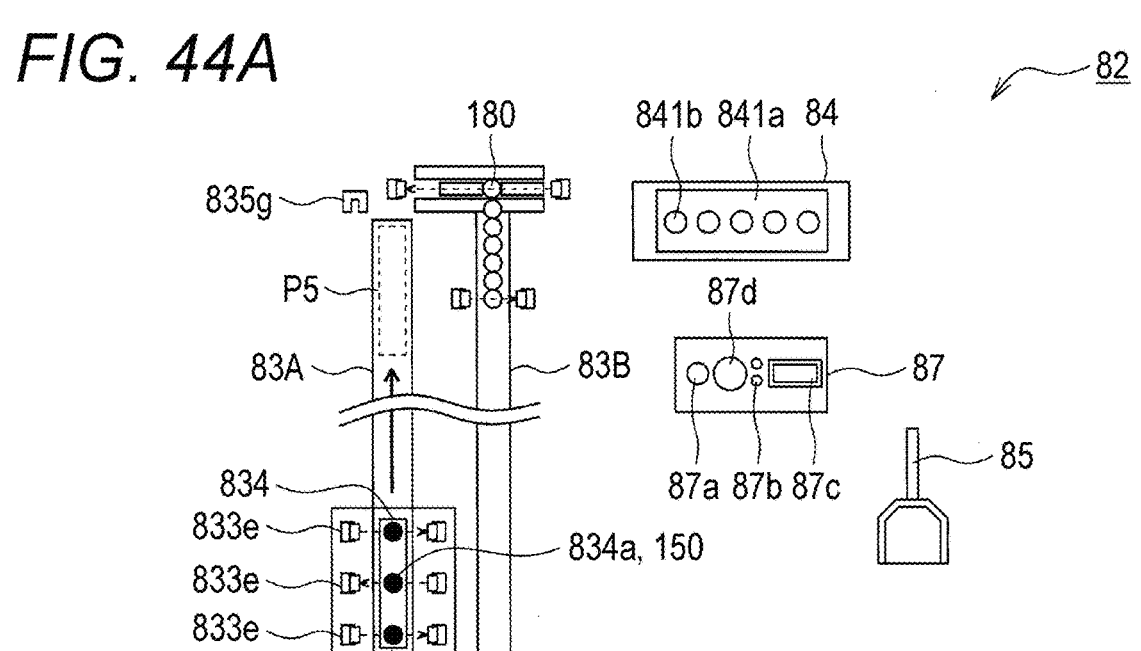
FIGS. 44A, 44B, and 44C are diagrams showing actions of a supply unit when housing a QC specimen containers in a cold insulation section.
Figure 44B:
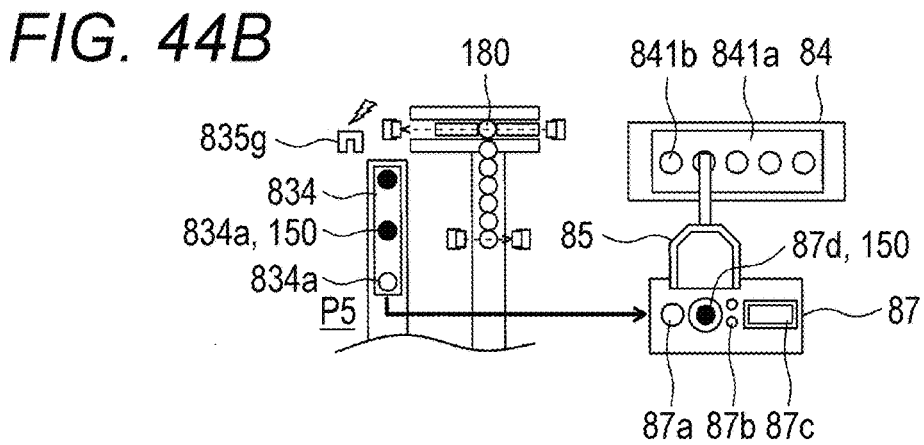
Figure 44C:
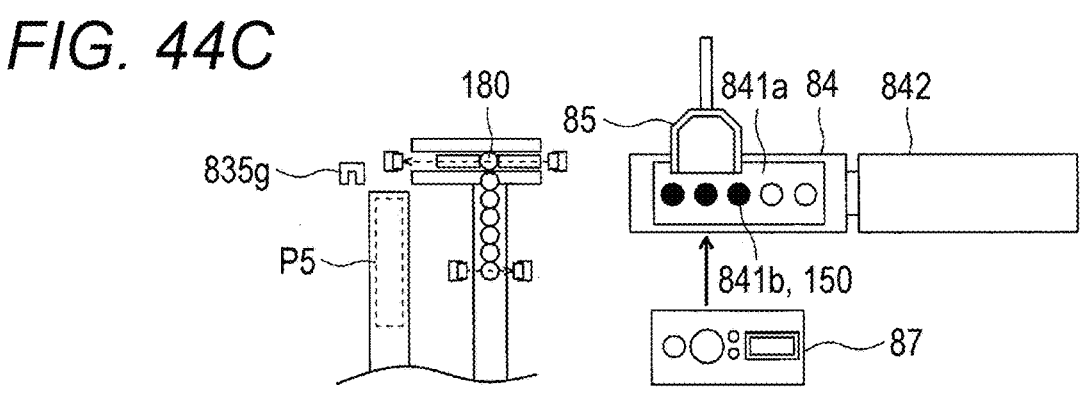

FIGS. 44A, 44B, and 44C are diagrams showing an action of the supply unit 80 in steps S301 to S306 in FIG. 35. As shown in FIG. 44A, when the QC specimen container 150 is stored in the cold insulation section 84 of the supply unit 80, the user sets the QC specimen container 150 in the transfer holder 834 in the first charging port 831A of the first charging section 83A. Since the first charging port 831A is covered with the first cover 832A, the user needs to open the first cover 832A and set the QC specimen container 150. The first charging section 83A is provided with the locking mechanism for the first cover 832A. When the transfer holder 834 is present at the first charging port 831A, the first cover 832A is unlocked, and the first cover 832A can be opened.

At the first charging port 831A, the transfer holder 834 is detected by the sensor 835f. When the sensor 835f detects the transfer holder 834, for example, the charge icon 2005 (see FIG. 19) of the monitor 91 can be operated, and when the charge icon 2005 is pressed, the first cover 832A is unlocked. By making it possible to open the first cover 832A only when the transfer holder 834 is present at the first charging port 831A, it is possible to prevent the QC specimen container 150 from being erroneously charged into the first charging port 831A in which the transfer holder 834 is not present.

When the QC specimen container 150 is set in the housing portion 834a of the transfer holder 834 and the first cover 832A is closed, the control section 82a moves the transfer holder 834 to transfer the QC specimen container 150 to the inside of the storage adjustment unit 82. Since the sensor 833e is installed in the first charging port 831A corresponding to each housing portion 834a, the presence or absence of the QC specimen container 150 and the number of charged QC specimen containers 150 can be detected from detection information of the sensor 833e.

As shown in FIG. 44B, the transfer holder 834 moves from the first charging port 831A to the take-out position P5 inside the storage adjustment unit 82. When the transfer holder 834 arrives at the take-out position P5 and the transfer holder 834 is detected by the sensor 835g, the transfer section 85 takes out the QC specimen container 150 from the transfer holder 834, and the transfer section 85 transfers the QC specimen container 150 one by one to the information reading section 87. In the information reading section 87, the rollers 87a and 87b rotate the QC specimen container 150 arranged in the housing portion 87d, and the reading portion 87c reads the QC specimen ID from the machine-readable label 103.

As shown in FIG. 44C, the transfer section 85 transfers the QC specimen container 150 from the information reading section 87 to the cold insulation section 84 to house the QC specimen container 150 in the housing portion 841b of the cold insulation chamber 841a. When the transfer of all the QC specimen containers 150 to the cold insulation section 84 is finished, the cold insulation section 84 closes the cover 842, and the cold insulation section 84 starts cooling storage of the QC specimen containers 150. In the example of FIG. 44C, after all the QC specimen containers 150 are taken out from the transfer holder 834, the transfer holder 834 is returned to the first charging port 831A. The read QC specimen ID information is transmitted to the control section 82a. The QC specimen ID contains information on the concentration level, lot number and expiration date of the QC specimen. The control section 82a updates the database 820 based on the received QC specimen ID information. Since the number of remaining tests of the QC specimen container 150 is 24 tests when it is unused, the control section 82a inputs 24 as an initial value of the number of remaining tests when adding a new QC specimen container 150 to the database 820.

Figure 36:
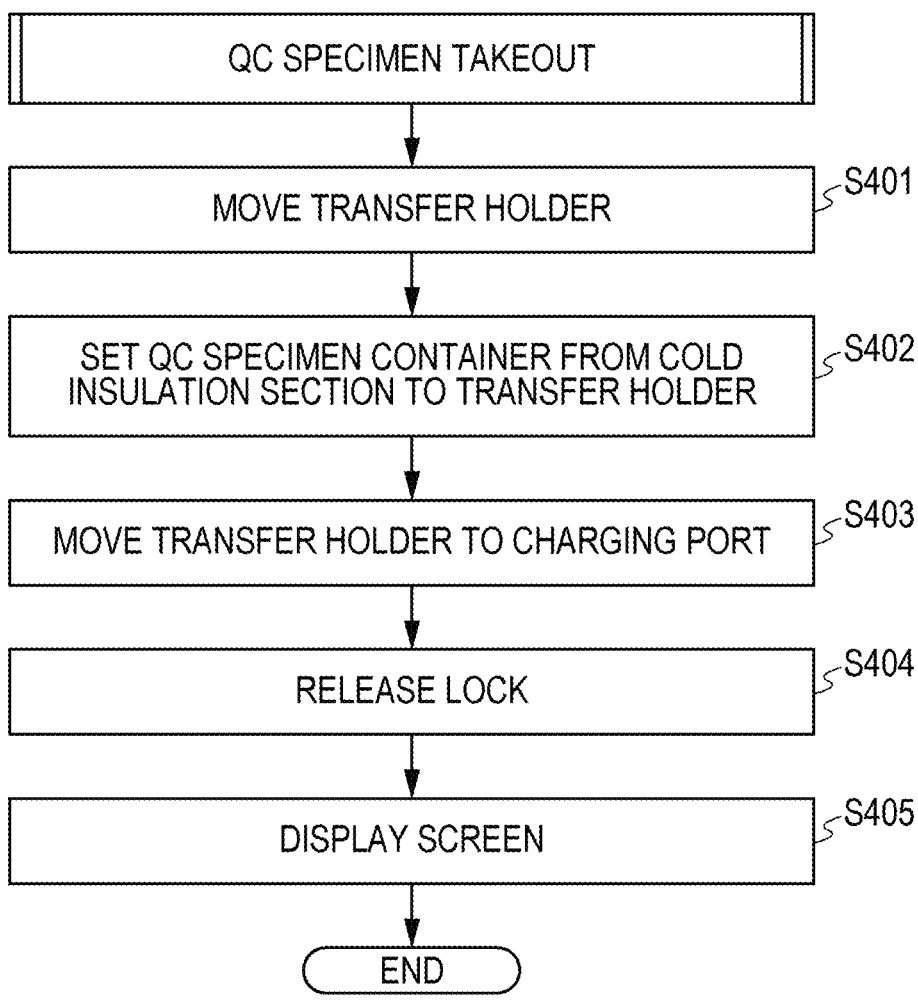
FIG. 36 is a flowchart showing a procedure of a process for taking out a QC specimen container from a cold insulation section of a supply unit.

FIG. 36 is a flowchart showing a process of taking out the QC specimen container 150 from the cold insulation section 84 of the supply unit 80 (S400 in FIG. 30). As described above, the process of FIG. 36 is executed when the take-out icon 2004 on the device status screen 2000 is operated. In step S401, the control section 82a controls the transfer holder 834 to move the QC specimen container 150 to the inside of the storage adjustment unit 82. At this time, the transfer holder 834 moves to the take-out position P5 of the first charging section 83A. In step S402, the control section 82a controls the transfer section 85 to take out the QC specimen container 150 housed in the housing portion 841b corresponding to the position number designated in the screen 2200 in FIG. 21 from the cold insulation section 84 and set the QC specimen container 150 in the transfer holder 834 at the take-out position P5.

In step S403, the control section 82a controls to move the transfer holder 834 in which the QC specimen container 150 is set to the first charging port 831A. In step S404, the control section 82a unlocks the first cover 832A. In step S405, the control section 82a displays a screen notifying arrival of the QC specimen container 150. An example of this screen is the notification screen 2210 in FIG. 21, which is displayed on the monitor 91.

Figure 37:
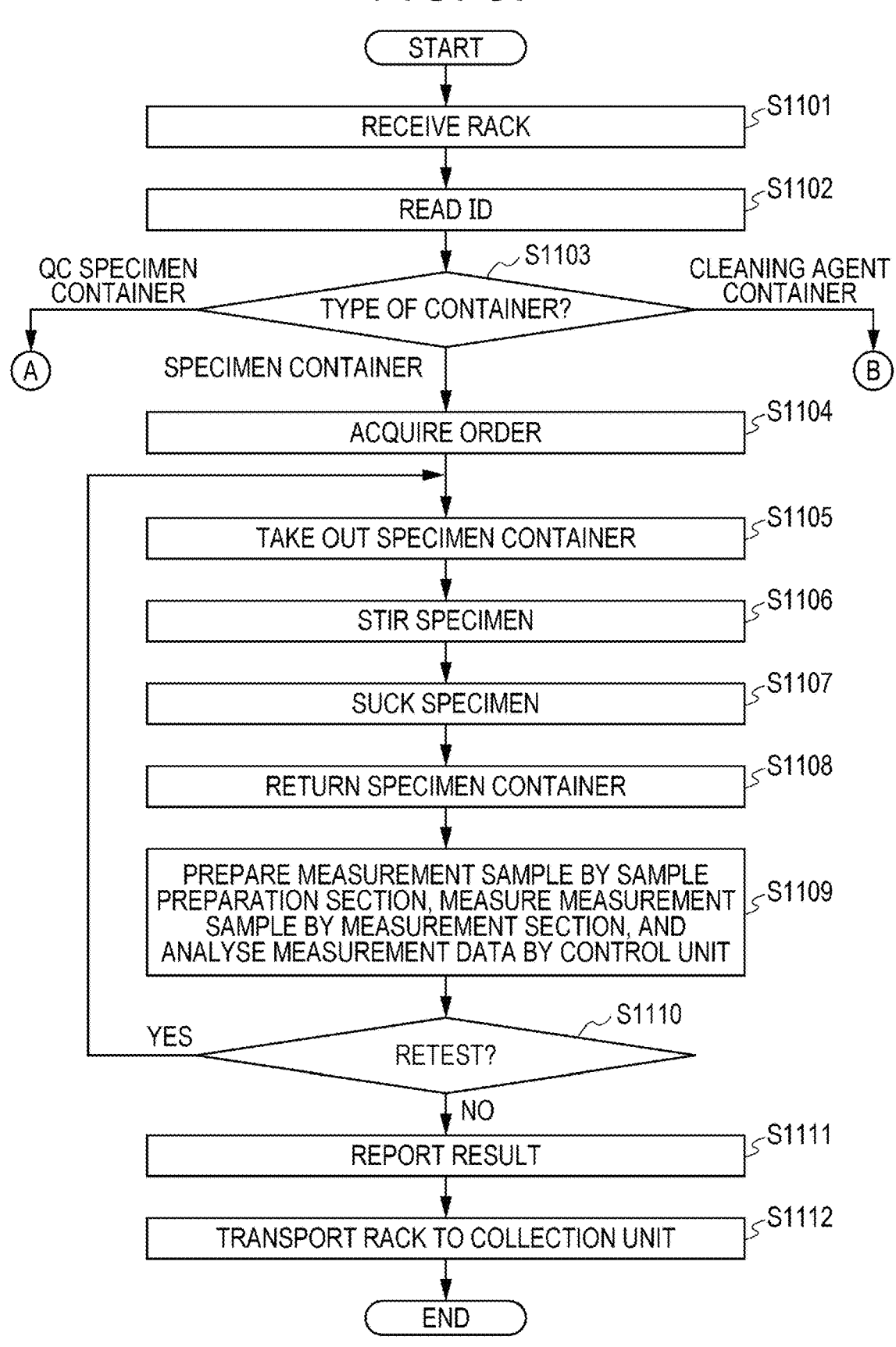
FIG. 37 is a flowchart showing a measurement procedure of a specimen container in a measurement unit.
Figure 38:
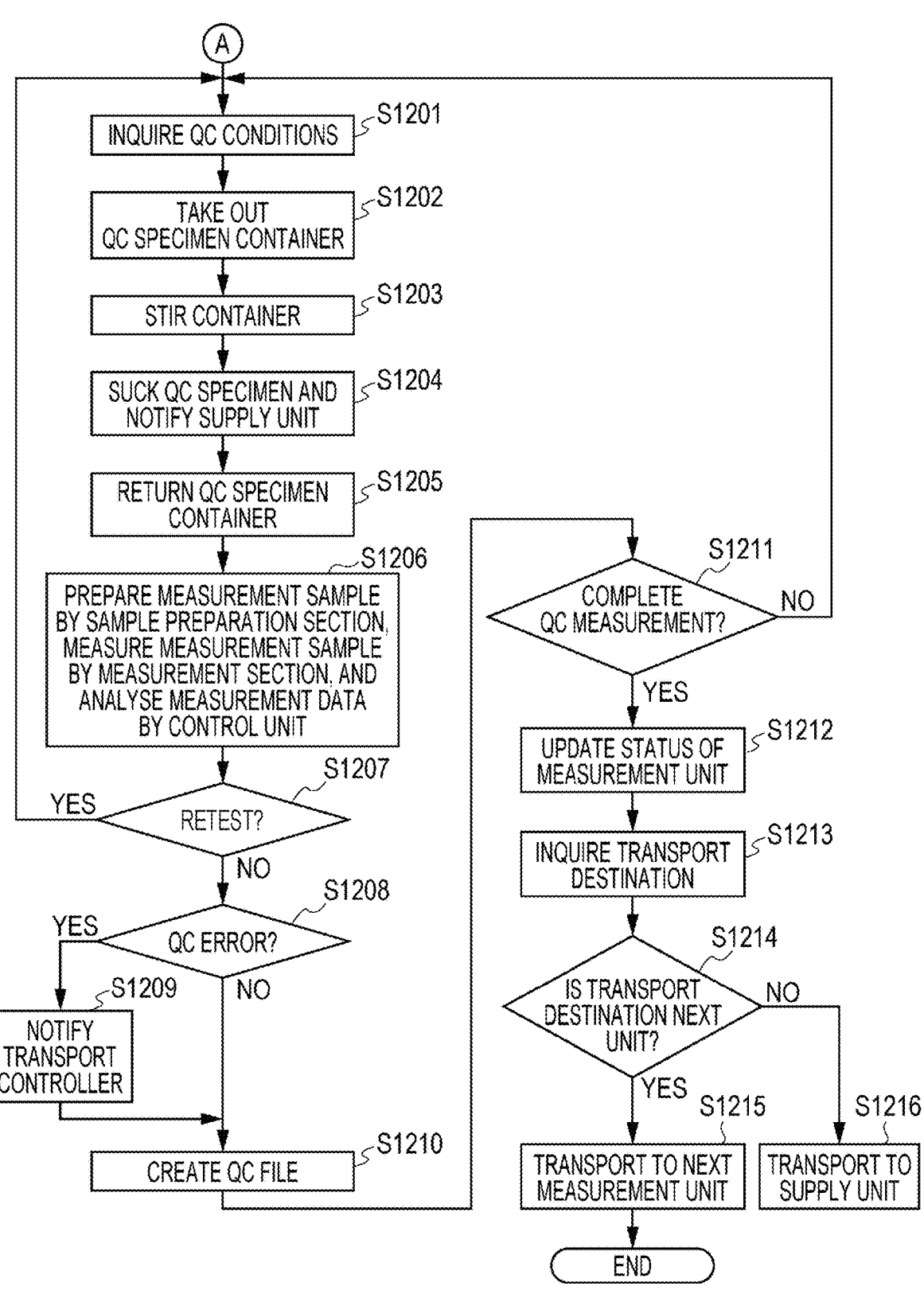
FIG. 38 is a flowchart showing a measurement procedure of a QC specimen container in a measurement unit.
Figure 39:
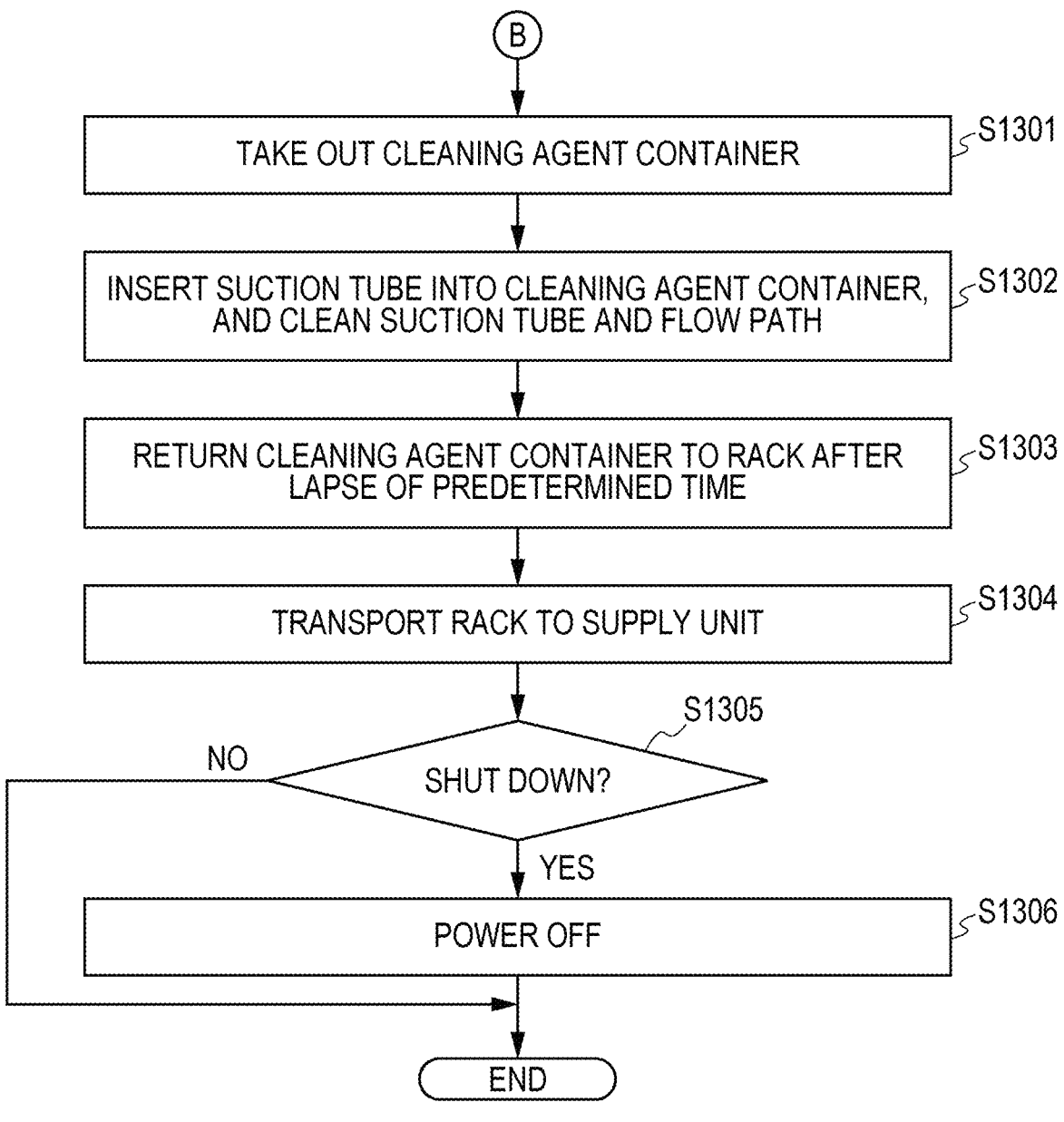
FIG. 39 is a flowchart showing a procedure of a cleaning process using a cleaning agent container in a measurement unit.

FIGS. 37, 38, and 39 are flowcharts showing an action of the measurement unit. The action of the measurement unit is mainly controlled by the control section 31. In the following, the action will be described by taking the first measurement unit 10A as an example, and the same applies to the second measurement unit 10B.

FIG. 37 is a flowchart showing an example of a measurement procedure for the specimen container 100, and steps S1101 and S1102 are also common to the QC specimen container 150 and the cleaning agent container 180. In step S1101, the control section 31 transports the specimen rack 110 to the second transport path 22 arranged in front of the first measurement unit 10A. In step S1102, the control section 31 causes the information reading section 26 to read the specimen ID and the rack ID. The specimen container 100 whose specimen ID has been read is transported to the take-out position P2 corresponding to either the first measurement unit 10A or the second measurement unit 10B. Here, it is assumed that the specimen container 100 is transported to the take-out position P2 of the first measurement unit 10A.

In step S1103, the control section 31 determines the type of container based on the specimen ID read in step S1102. When the control section 31 determines that the container transported to the take-out position P2 is the specimen container 100, the process proceeds to step S1104. When the container transported to the take-out position P2 is the QC specimen container 150, the process proceeds to step S1201 in FIG. 38, and when the container is the cleaning agent container 180, the process proceeds to step S1301 in FIG. 39.

In step S1104, the control section 31 inquires the host computer 120 about the measurement order to acquire the measurement order. In step S1105, the control section 31 controls the robot hand 15 to take out the specimen container 100 from the housing portion 111 of the specimen rack 110. Under the control of the control section 31, in step S1106, the robot hand 15 overturns and stirs the taken-out specimen container 100, and in step S1507, the suction tube 13a of the sample preparation section 13 sucks the specimen from the specimen container 100. When the suction of the specimen is finished, the specimen container 100 is returned to the original housing portion 111 of the specimen rack 110 by the robot hand 15 in step S1108.

Under the control of the control section 31, in step S1109, the sample preparation section 13 prepares a measurement sample from the sucked specimen, the measurement section 14 measures the sample (initial test), and the measurement section 14 analyzes the measurement data. In step S1110, the control section 31 determines whether or not to perform a retest based on the measurement result of the initial test. When a retest is performed, the process returns to step S1105, and when a retest is not performed, the result of the initial test is sent to the host computer 120 (step S1111). When the initial test and the necessary retest are finished for all the specimen containers 100 housed in the specimen rack 110, a smear is prepared via the process unit 40 if necessary, and the smear is then transported to the collection unit 60 (step S1112).

FIG. 38 is a flowchart showing an example of a process procedure when the container is the QC specimen container 150 in step S1103 in FIG. 37. In step S1201, the control section 31 inquires the control section 82a of the supply unit 80 about the QC conditions to acquire the QC conditions, and the control section 31 transports the QC specimen container 150 to be measured to the take-out position P2 of the target first measurement unit, based on the QC conditions. Under the control of the control section 31, in step S1202, the robot hand 15 takes out the QC specimen container 150 from the housing portion 111 of the QC specimen rack 160, and in step S1203, the robot hand 15 overturns and stirs the taken-out QC specimen container 150. The registered QC conditions information may be provided to the control section 31 in advance, in which case the inquiry in step S1201 is unnecessary.

Under the control of the control section 31, in step S1204, the suction tube 13a of the sample preparation section 13 sucks the QC specimen from the QC specimen container 150, and in step S1205, the robot hand 15 returns the QC specimen container 150 to the original housing portion 111 of the QC specimen rack 160. In step S1206, the sample preparation section 13 prepares a measurement sample from the sucked QC specimen, the measurement section 14 measures the sample (initial test), and the measurement section 14 analyzes the measurement data. When the QC specimen is sucked in step S1204, the control section 31 notifies the control section 82a of the supply unit 80 of the information. The information on the number of suctions of the QC specimen is used when updating the number of remaining tests in the database 820. Alternatively, when the control section 82a receives this notification, the database 820 may be updated by reducing the number of remaining tests for the corresponding QC specimen container 150.

The control section 31 determines whether or not a retest is necessary when a retest for re-measuring the QC specimen is set as the QC conditions (step S1207). For example, when the measured value is abnormal, such that when the measured value is out of a predetermined allowable range, or when an error from the previous value is out of the allowable range, it is determined that a retest is necessary. In the present embodiment or embodiments, it is assumed that the retest is performed automatically up to once. That is, when steps S1201 to S1206 have been repeated by the retest, the process proceeds to step S1208 regardless of the result of the retest.

In step S1208, the control section 31 determines whether or not to output a QC error. The QC error is output when the measured value of the QC specimen is still abnormal even performing a retest, for example, when the measured value of the QC specimen is out of the predetermined allowable range, or when the error from the previous value is out of the allowable range. The QC error is displayed, for example, on the monitor 91 of the supply unit 80.

When the control section 31 outputs a QC error, the control section 31 provides a prescribed notification to the transport controller 70 (step S1209). The prescribed notification includes information for specifying the measurement unit in which the QC error has occurred. The transport controller is programmed to prohibit the transport of the specimen container 100 to the measurement unit in which the QC error has occurred. Since the specimen analysis system 1 has a plurality of measurement units, only a measurement unit in which the measured value of the QC specimen is normal is defined as a supply destination of the specimen container 100, and a measurement unit in which the measured value of the QC specimen is abnormal is excluded from the supply destination of the specimen container 100. For example, when a QC error occurs in either of the measurement units 10A or 10B of the measurement block 10 on the upstream side in the specimen analysis system 1 of FIG. 1, the transport controller 70 excludes the measurement block on the upstream side from the supply destination of the specimen container 100, so that the specimen container can be supplied only to the measurement block 10 on the downstream side. By doing so, it is possible to prevent the specimen from being erroneously measured by a measurement unit whose accuracy is not guaranteed, in which a QC error has occurred. It is highly convenient because the measurement can be started by another normal measurement unit while the measurement unit is restored when a QC error occurs.

Based on the measured values of the QC specimens, the control section 31 creates a QC file (step S1210). As described above, the QC file is the measurement results of the QC specimens created for each concentration level and lot, which is stored in the database 310. When a QC file has already been created for the same concentration level and lot as the measured QC specimen, the file is updated by adding new measured value to the QC file. In step S1211, the control section 31 determines whether or not the quality control measurement of the first measurement unit is all finished based on the QC conditions. When all the measurements have not been finished, for example, when it is necessary to measure QC specimens at different concentration levels, steps S1201 to S1211 are repeated.

When the measurement in the first measurement unit is all finished (YES in step S1211), the control section 31 updates the status of the first measurement unit based on the result of QC (step S1212). The status includes, for example, standby and error. Standby is a state in which the measurement unit can measure a specimen. Error is a state in which an error has occurred in the measurement unit, and a state in which measurement of a specimen is impossible or prohibited. The control section 31 sets the status of the measurement unit to standby when the QC result is normal, that is, no QC error has occurred. The control section 31 is programmed to control the transport unit 20 so that when specimen rack 110 housing the specimen container 100 is transported, the specimen container 100 is supplied to the measurement unit whose status is standby. When a QC error has occurred, the control section 31 sets the status of the measurement unit to error. The control section 31 is programmed not to supply the specimen to the measurement unit whose status is error. The measurement unit in which the error has occurred can be put into standby, for example, by manually measuring the QC specimen or restoring error by the user.

The control section 31 inquires the control section 82*a* of the supply unit 80 about the transport destination of the QC specimen rack 160 (step S1213). The control section 31 determines the transport destination (step S1214). When there is a next measurement unit as the transport destination of the QC specimen rack 160 (YES in step S1214), the transport unit 20 transports the QC specimen rack 160 to the next measurement unit under the control of the control section 31 (step S1215). For example, when the next measurement unit is the second measurement unit 10B, the transport unit 20 transports the QC specimen rack 160 from the first measurement unit 10A toward the second measurement unit 10B through the second transport path 22. When the next measurement unit is the adjacent measurement block, the transport unit 20 transports the QC specimen rack 160 downstream by the belt 21*b* (see FIG. 5) of the first transport path 21. When the transport destination of the QC specimen rack 160 is the supply unit (NO in step S1214), the transport unit 20 transports the QC specimen rack 160 through the third transport path 23, in order to transport the QC specimen rack 160 to the supply unit 80 (step S1216).

FIG. 39 is a flowchart showing an example of a process procedure when the container is the cleaning agent container 180 in step S1103 in FIG. 37. In this case, the cleaning agent container 180 is taken into the first measurement unit 10A and the cleaning process is performed. In step S1301, the control section 31 takes out the cleaning agent container 180 from the housing portion 111 of the cleaning agent rack by the robot hand 15, and in step S1302, the control section 31 inserts the suction tube 13*a* into the cleaning agent container 180, and the control section 31 sucks the cleaning agent to clean the suction tube 13*a* and the flow path.

Figure 40:
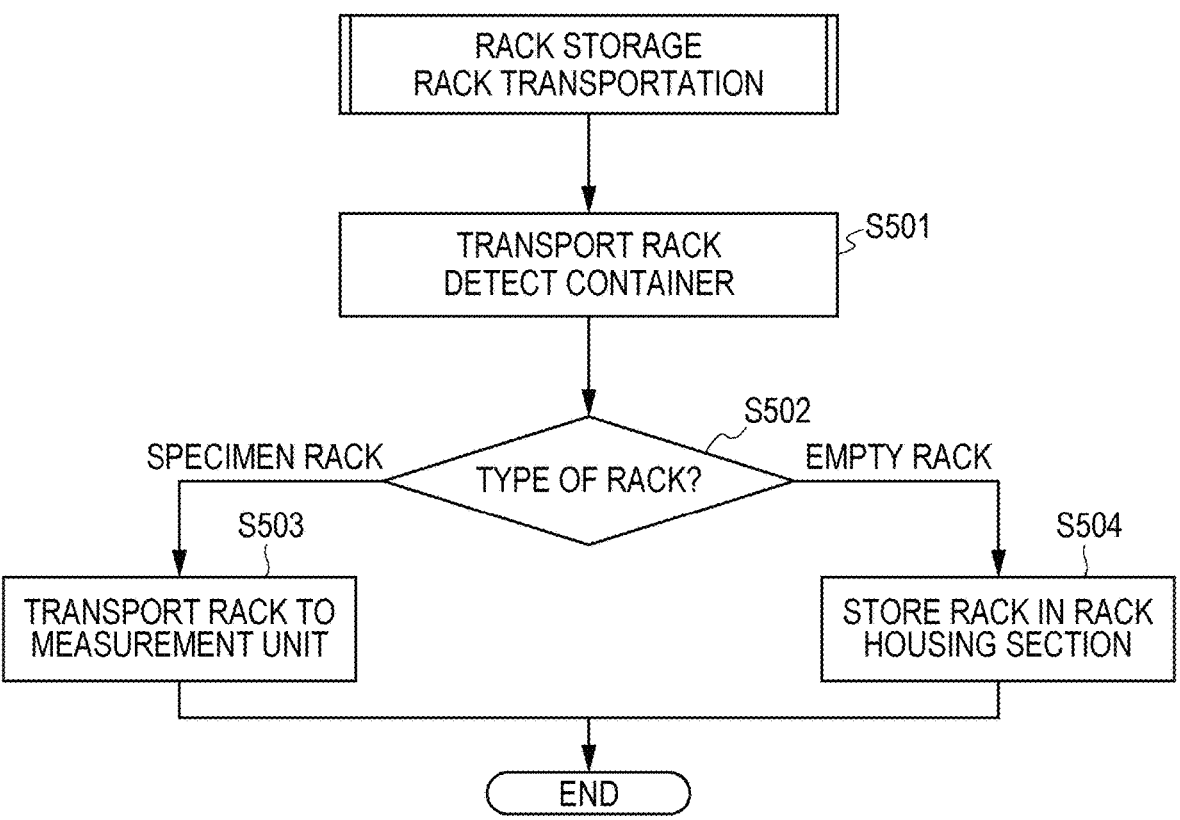
FIG. 40 is a flowchart showing a process procedure of rack transportation and storage.

The cleaning agent container 180 is returned to the rack after a lapse of a predetermined time (step S1303), and the cleaning agent rack housing the cleaning agent container 180 is transported to the supply unit 80 (step S1304). Thereafter, the control section 82*a* determines whether or not the execution of auto shut down is set to ON (step S1305). This determination is made based on the registration information of the schedule stored in the control section 82*a*. When auto shut down is set to ON, for example, after process of the used cleaning agent container 180 is finished, the control section 82*a* turns off the power supply of the cleaned measurement unit 10A or 10B (step S1306). FIG. 40 is a flowchart showing a process of the rack set in the first transport path 811 of the conveyor section 81 (S500 in FIG. 30). As described above, the supply unit 80 includes the first transport path 811 accessible from outside for the user to set the rack, and the user sets the specimen rack 110 and the empty rack 170 in the first transport path 811. The rack set in the first transport path is detected by the sensor 818*b*.

In step S501, the control section 82*a* executes control for transporting the rack from the first transport path 811 to the second transport path 812, and the control section 82*a* detects the container by the sensor 818*d*. In step S502, the control section 82*a* determines whether the rack set in the first transport path 811 is the specimen rack 110 or the empty rack 170. The control section 82*a* determines the type of rack based on whether or not the container is housed in the rack. The control section 82*a* determines that the rack is a specimen rack when the container is detected. The control section 82*a* determines that the rack is an empty rack when the container is not detected. The process of FIG. 40 is executed when the rack is set in the first transport path 811 by the user. In the present embodiment or embodiments, since it is assumed that the QC specimen rack 160 housing the QC specimen container 150 returns to the supply unit 80 via the fifth transport path 815, there is no branch corresponding to the QC specimen rack 160 in the determination of S501.

When the rack set in the first transport path 811 is the specimen rack 110, the specimen rack 110 is transported to the measurement unit under the control of the control section 82*a* and the transport unit 70 (step S503). When the rack set in the first transport path 811 is the empty rack 170, the empty rack 170 is transported to the rack housing section 88, and the empty rack 170 is stored in the rack housing section 88 (step S504).

Figure 45A:
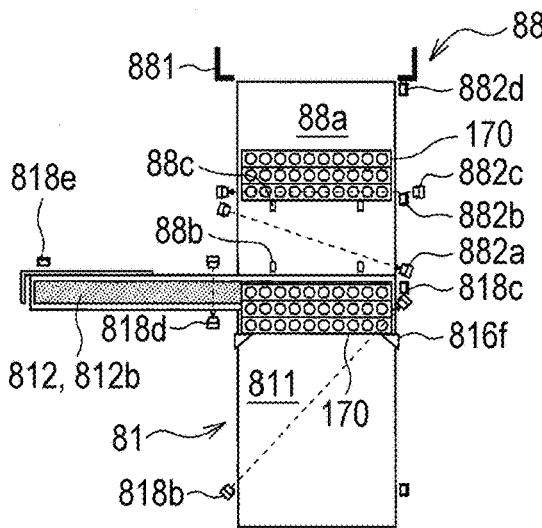
FIGS. 45A, 45B, 45C, and 45D are diagrams showing actions of a supply unit when housing empty racks in a rack housing section.
Figure 45B:
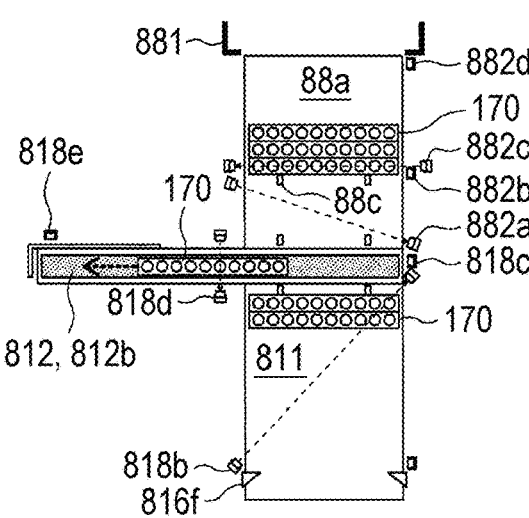

FIGS. 45A, 45B, 45C, and 45D are diagrams showing an action of the supply unit 80 in steps S502 and S504 in FIG. 40. As shown in FIG. 45A, when the user sets the empty rack 170 in the first transport path 811, the empty rack 170 is detected by the sensor 818*b*, and the empty rack 170 is pushed out from the first transport path 811 to the right end side of the second transport path 812 by the first delivery section 816A. Next, as shown in FIG. 45B, the empty rack 170 is detected by the sensor 818c at the right end position of the second transport path 812, the empty rack 170 is moved to the left end position by the belt 812b of the second transport path 812, and the empty rack 170 is detected by the sensor 818e.

Figure 45C:
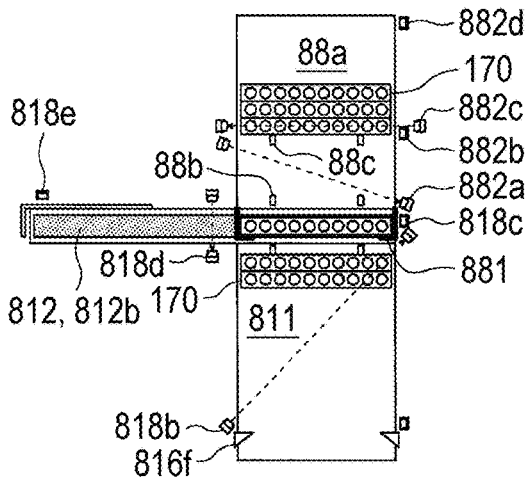
Figure 45D:
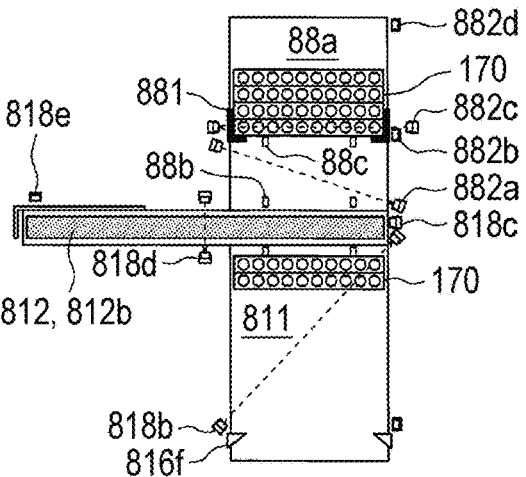

When the container is not detected by the sensor 818d and the rack is confirmed to be an empty rack 170 in the second transport path 812, the empty rack 170 is returned again to the rightmost position of the second transport path 812 by the belt 812b, as shown in FIG. 45C. Then, as shown in FIG. 45D, the empty rack 170 is detected by the sensor 818c, and the empty rack 170 is pulled into the transport path 88a by the transport arms 881. The empty rack 170 is pulled by the transport arms 881 to the position of the front end rack behind the stopper 88c. At this time, the stoppers 88b and 88c are interlocked and lowered so as not to hinder the transportation of the empty rack 170.

Figure 41:
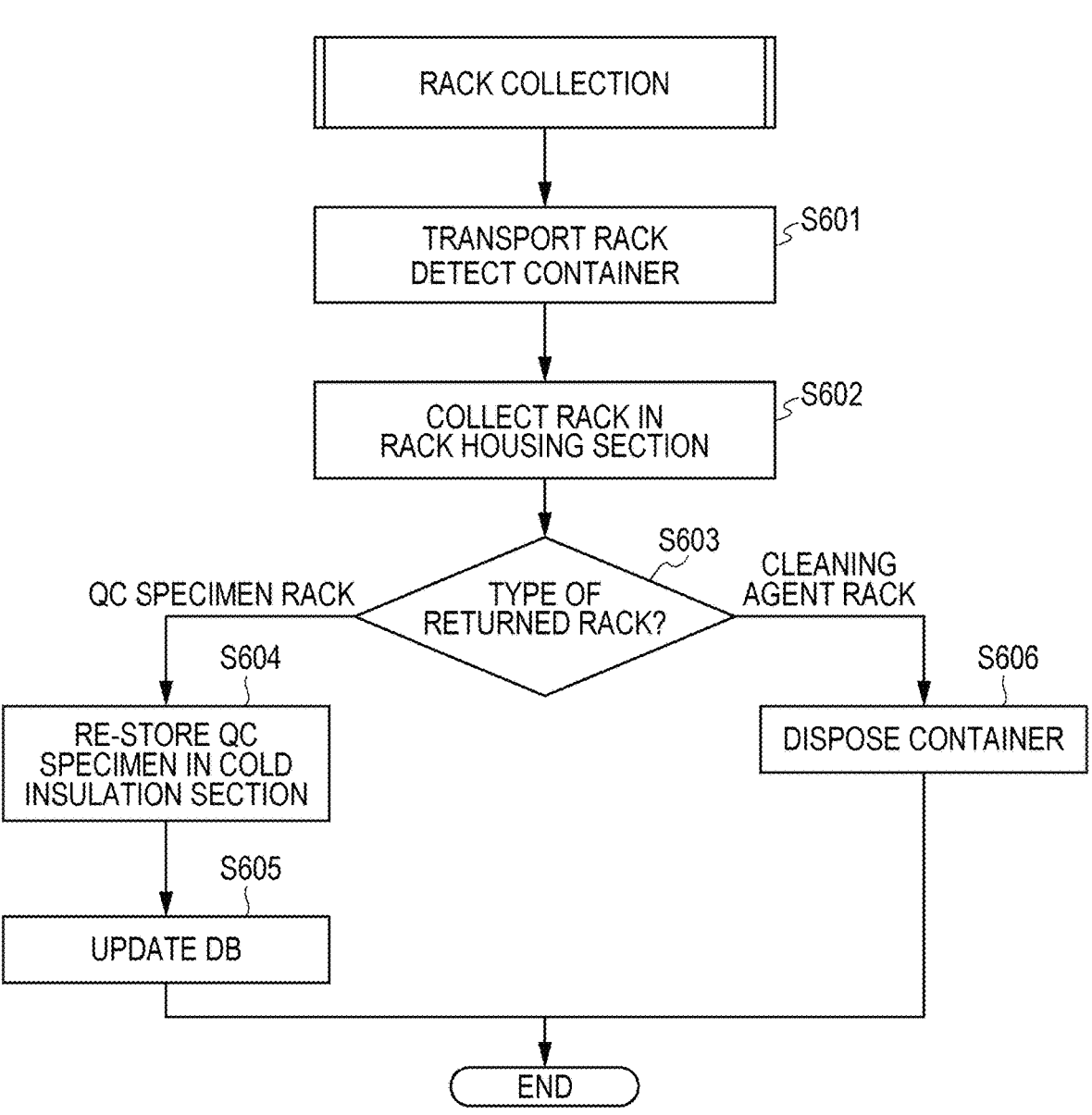
FIG. 41 is a flowchart showing a process procedure of rack collection.

FIG. 41 is a flowchart showing a process when the rack returns to the supply unit 80 (S600 in FIG. 30). As described above, the supply unit 80 includes a fifth transport path 815 for receiving racks from the adjacent transport units 20, and the QC specimen rack 160 and the cleaning agent rack return to the supply unit 80.

In step S601, the control section 82a controls the second transport path 812 to transport the rack, and the first information reading section 817A and the second information reading section 817B read ID of the container housed in the rack.

The control section 82a controls the second transport path 812 and the rack housing section 88 so that the rack whose container ID has been read is collected by the rack housing section 88 (step S602). Based on the ID read in step S601, the control section 82a determines whether the returned rack is the QC specimen rack 160 or the cleaning agent rack (step S603). When the container housed in the rack is the QC specimen container 150, the control section 82a determines that the rack is the QC specimen rack 160. When the container housed in the rack is the cleaning agent container 180, the control section 82a determines that the rack is a cleaning agent rack.

When the collected rack is the QC specimen rack 160 housing the QC specimen container 150, the control section 82a controls the transfer section 85 and the cold insulation section 84 to house and re-store the QC specimen container 150 in the cold insulation section 84 (step S604). The control section 82a updates the database 820 based on the process in step S602 (step S605). Specifically, the control section 82a updates the number of remaining tests of the QC specimen in the database 820, based on the notification of suction from the QC specimen container 150 received from the measurement units 10A and 10B. In the above embodiment or embodiments, the QC specimen container 150 is re-stored regardless of the remaining amount in step S602, but the QC specimen container 150 may be processed based on, for example, the remaining amount information. For example, the QC specimen container 150 with a number of remaining tests of 1 or more may be transferred to the cold insulation section 84 for storage, and the QC specimen container 150 with a number of remaining tests of less than 1 may be transferred to the first collection section 89A for disposal.

When the collected rack is a cleaning agent rack housing the cleaning agent container 180, the control section 82a controls the transfer section 85 to transfer the cleaning agent container 180 from the rack to the second collection section 89B for disposal (step S606).

Figure 46:
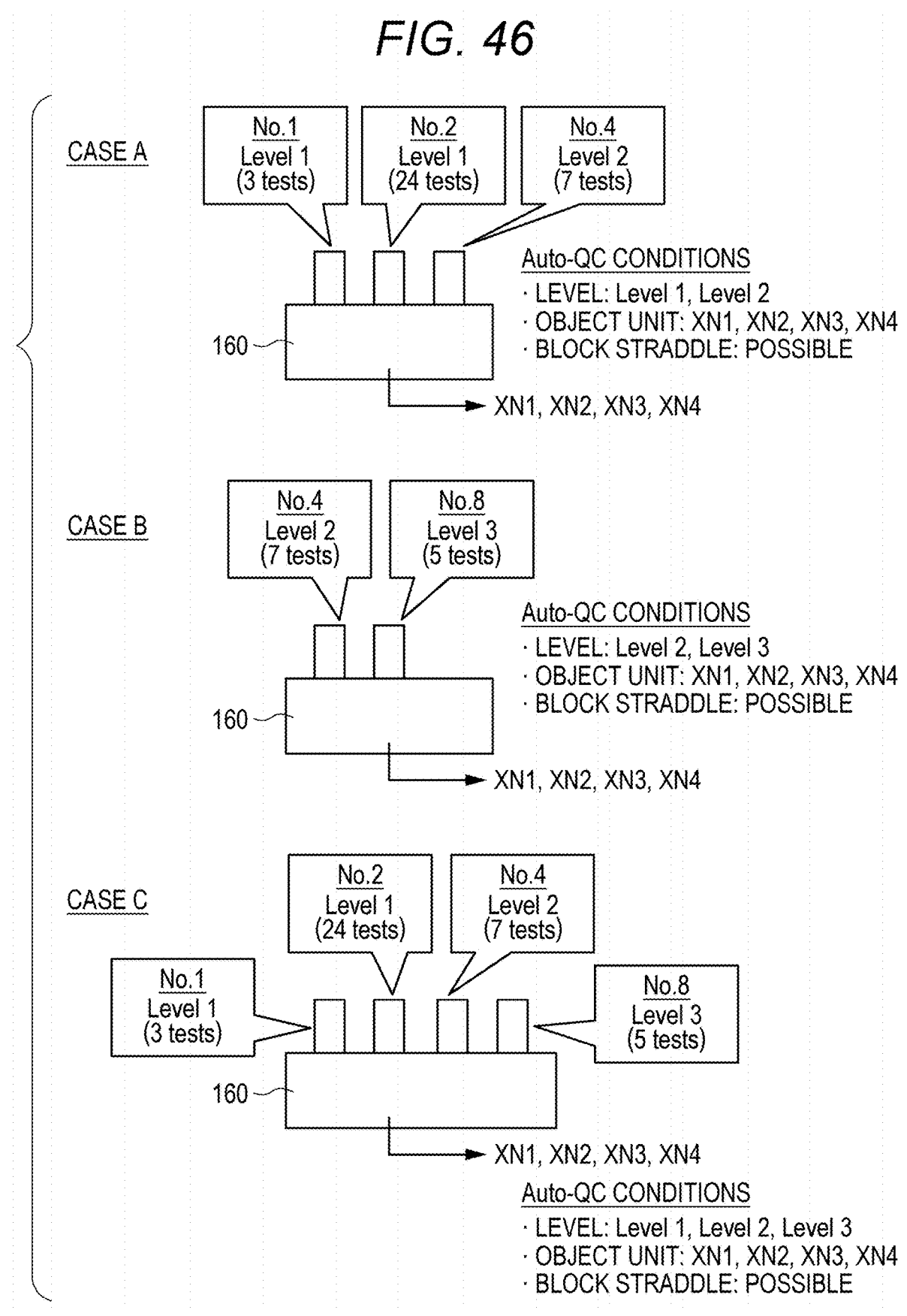
Figure 47:
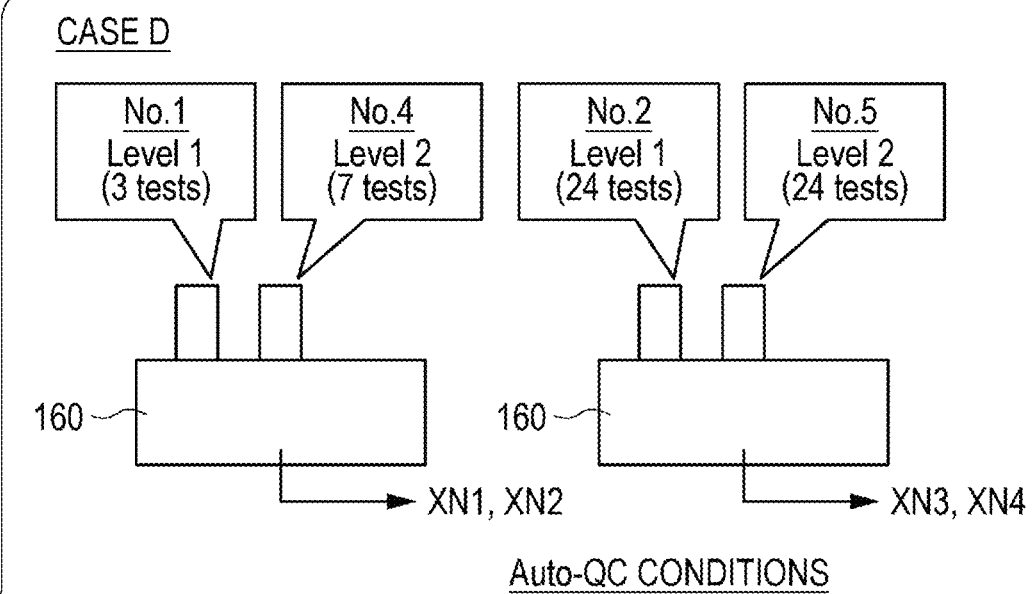
FIG. 47 is a diagram showing a specific example of a combination of QC specimen containers.
Figure 47:
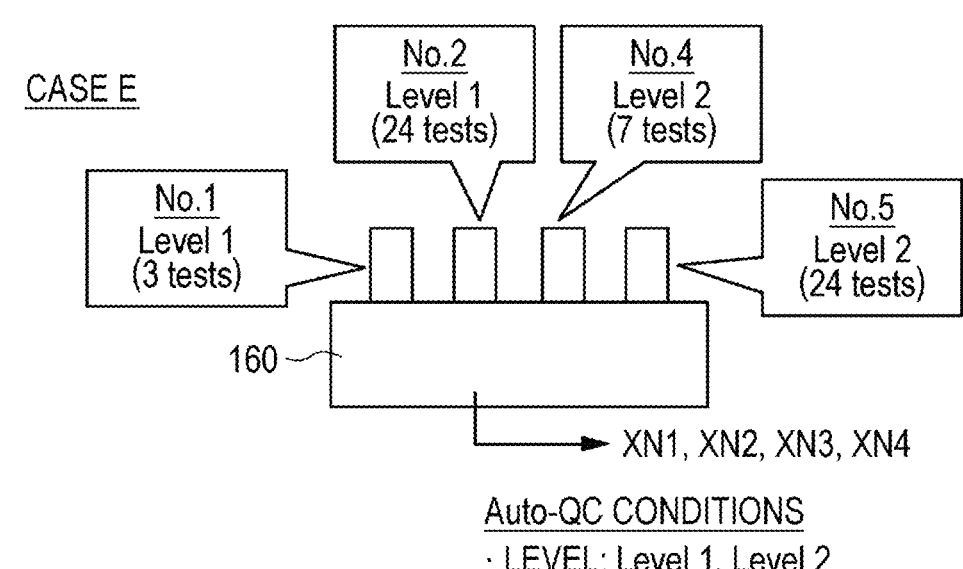
Figure 48:
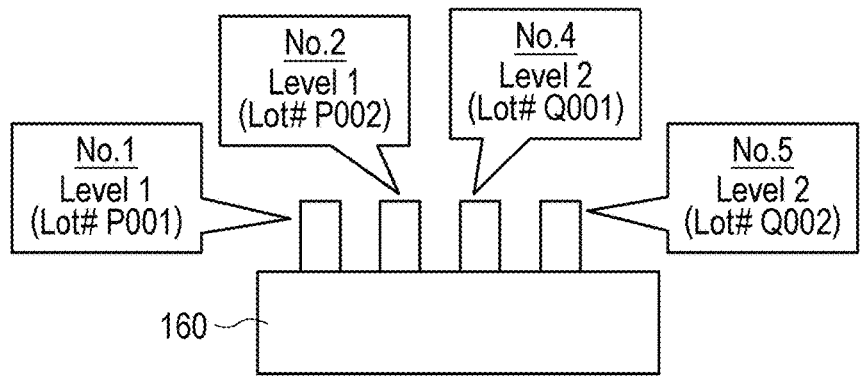
FIG. 48 is a diagram showing a specific example of a combination of QC specimen containers.

FIGS. 46, 47, and 48 are diagrams for explaining in detail a step of determining the combination of the QC specimen containers 150 based on the QC conditions and the information on the QC specimen containers 150 in storage in step S101 in FIG. 32. In the following, a case where the QC specimen containers 150 shown in the database 820 of FIG. 29 are stored in the cold insulation section 84 will be described.

FIG. 46 shows cases A to C.

<Case A>

In case A, the following QC conditions are set.

Concentration level to be used: Level 1, Level 2

Object unit of quality control measurement: XN1, XN2, XN3, XN4

Block straddle: Possible

The block straddle is a setting regarding whether or not to perform quality control measurement of a plurality of measurement blocks by one QC specimen rack 160. When the block straddle is "possible", the quality control measurement of the entire specimen analysis system is performed by the QC specimen container 150 set in one QC specimen rack 160. Whether to enable or disable block straddle is changed according to the user's preference, such as whether to prioritize the efficiency of auto QC or prioritize the ease of management of QC specimens.

For example, when the block straddle is set to "impossible", the QC specimen rack 160 is transported to each of the plurality of measurement blocks. Since quality control measurement can be performed in parallel for the plurality of measurement blocks, quality control measurement of the entire specimen analysis system can be efficiently executed.

When the block straddle is set to "possible", quality control of the plurality of measurement blocks can be performed by using the QC specimen container 150 set in one QC specimen rack 160. When quality control measurement is performed in parallel, for example, since a plurality of QC specimen containers 150 with the same concentration level are used at the same time, management of the expiration date and lot number may become complicated. In this regard, when the block straddle is set to "possible", for example, the same QC specimen container 150 is used in the first measurement block and the second measurement block, so that the number of QC specimen containers 150 consumed at a time can be reduced, which is easier to manage.

In case A, since the block straddle is set to "possible", level 1 and level 2 QC specimen containers 150 are housed in one rack. The control section 82a specifies a usable QC specimen container 150 from among the QC specimen containers 150 with the same lot number as the lot number in operation. Here, the lot number in operation is "A01XXXX" for level 1, and the lot number in operation is "A02XXXX" for level 2. In this case, for level 1, QC specimen containers 150 at position numbers 1 and 2 are specified as usable containers. For level 2, QC specimen containers 150 at position numbers 4 and 5 are specified as usable containers.

When the usable QC specimen container 150 is determined to be only one based on the lot number, the control section 82a determines whether the number of remaining tests of the container is equal to or greater than the number of tests to be performed by the auto QC. As described above, when the number of remaining tests is less than the number of tests to be performed, the control section 82a outputs an auto QC error to cancel the schedule. When the number of remaining tests is equal to or greater than the number of tests, the specified QC specimen container 150 is set in the rack.

When there are two or more usable QC specimen containers 150 based on the lot number, the control section 82a determines whether the number of remaining tests of a container with the smallest number of remaining tests is equal to or greater than the number of tests scheduled by the auto QC. When the number of remaining tests is equal to or greater than the number of tests to be performed, the specified container, that is, the container with the smallest number of remaining tests is set in the rack. When the number of remaining tests is less than the number of tests to be performed, whether the total number of remaining tests of the container with the smallest number of remaining tests and the number of remaining tests of the other container with the second smallest number of remaining tests (the total number of remaining tests) is equal to or greater than the number of tests to be performed is determined.

When the total number of remaining tests is equal to or greater than the number of tests to be performed, the two QC specimen containers 150 are set in the rack. When the total number of remaining tests of the two QC specimen containers 150 is less than the number of tests to be performed, the total number of remaining tests of the third QC specimen container 150 is further added, and the similar determination is repeated. When the total number of remaining tests of the QC specimen container 150 specified as usable based on the lot number is less than the number of tests to be performed, an auto QC error is output to cancel the schedule.

In case A, level 1 requires 4 tests of 4 units, XN1 to XN4. Of the QC specimen containers 150 at position numbers 1 and 2 specified based on the lot number, position number 1 with the small number of remaining tests is preferentially used. The number of remaining tests "3" in the QC specimen container 150 at position number 1 is compared with the number of tests to be performed "4". Since the number of remaining tests of the QC specimen container 150 at position number 1 is 3, which is less than the number of tests to be performed 4, only the QC specimen container 150 at position number 1 is insufficient to perform quality control measurement with XN1 to XN4 by 1 test. Therefore, the total number of remaining tests "27", which is the sum of the remaining test number "24" of the QC specimen container 150 at position number 2 with the second smallest number of remaining tests and the remaining test number "3" of the QC specimen container 150 at position number 1, is compared with the number of tests to be performed "4". Since 27 tests are equal to or greater than the number of tests to be performed, in this case, the auto QC error is avoided, and the QC specimen containers 150 at position numbers 1 and 2 are combined and set in the rack. In other words, the QC specimen containers 150 at position numbers 1 and 2 are combined, and level 1 quality control measurement is executed.

In case A, level 2 also requires 4 tests of 4 units, XN1 to XN4. The usable QC specimen containers 150 specified based on the lot number are the containers at position numbers 4 and 5. Since the number of remaining tests of the QC specimen container 150 at position number 4 is 7, which is equal to or greater than the number of tests to be performed 4, only the QC specimen container 150 at position number 4 is sufficient. Therefore, the QC specimen container 150 at position number 4 is set in the rack.

Therefore, in the case of case A, the QC specimen containers 150 at a position numbers 1, 2 and 4 are combined and set in one rack.

<Case B>
In case B, the following QC conditions are set.
Concentration level to be used: Level 2, Level 3
Object unit of quality control measurement: XN1, XN2, XN3, XN4
Block straddle: Possible For level 2, as in case A, the QC specimen container 150 at position number 4 can execute four quality control measurements only with the QC specimen container 150 at position number 4, so the QC specimen container 150 at position number 4 is specified as a container to be used for quality control measurement.

For level 3, only the QC specimen container 150 at position number 8 is stored in the cold insulation section 84. Since the number of remaining tests of the QC specimen container 150 at position number 8 is 5, which is equal to or greater than the number of tests to be performed 4, the QC specimen container 150 at position number 8 is specified as a container to be used for quality control measurement.

Therefore, in the case of case B, the QC specimen containers 150 at position numbers 4 and 8 are combined and set in one rack.

<Case C>
In case C, the following QC conditions are set.
Concentration level to be used: Level 1, Level 2, Level 3
Object unit of quality control measurement: XN1, XN2, XN3, XN4
Block straddle: Possible In case C, the QC specimen containers 150 at position numbers 1, 2, 4 and 8 are specified as the containers to be used for quality control measurements by the algorithms described for cases A and B above.

Therefore, in the case of case C, the four specified QC specimen containers 150 are combined and set in one rack.

FIG. 47 shows cases D and E.

<Case D>
In case D, the following QC conditions are set.
Concentration level to be used: Level 1, Level 2
Object unit of quality control measurement: XN1, XN2, XN3, XN4
Block straddle: Impossible In case D, unlike case A, the block straddle is set to "impossible". In this case, the number of measurement blocks to which one QC specimen rack 160 is transported is limited to one. That is, it is necessary to transport another QC specimen rack 160 to each measurement block.

In the first QC specimen rack 160, a QC specimen container 150 to be used for quality control measurement of the first measurement block is set. In the first QC specimen rack 160, QC specimen containers 150 with a number of remaining tests of 2 or more are specified for each of level 1 and level 2, and they are combined and set. The same applies to the second QC specimen rack 160. In the case of case D, a combination of QC specimen containers 150 with position numbers 1 and 4 is set in the first QC specimen rack 160, and a combination of QC specimen containers 150 with position numbers 2 and 5 is set in the second QC specimen rack 160.

<Case E>
In case E, the following QC conditions are set.
Concentration level to be used: Level 1, Level 2
Object unit of quality control measurement: XN1, XN2, XN3, XN4
Block straddle: Possible
Retest setting: Yes In case E, unlike case A, the condition of "Retest: Yes" is added. The "Retest: Yes" means a condition of automatically performing retest in a case where a retest is required as a result of measuring a QC specimen. Examples of the case where a retest is required include a case where the measured value is out of the allowable range as a result of measuring the QC specimen in the measurement unit, and a case where the error from the previous value is out of the allowable range.

In case E, it is assumed that when a retest is required as a result of quality control measurement by auto QC, the retest is performed automatically up to once. That is, it is assumed that one measurement unit performs a maximum of two measurements on one QC specimen container 150, including the initial test and the retest. The QC specimen container 150 is used after being taken out from the cold insulation section 84 and then heated in the heating section 86 for a certain period of time (for example, 15 minutes).

Therefore, when the number of remaining tests of the QC specimen container 150 set in the rack is less than the number of tests required for retest, and when the retest is required, it is necessary to take out a new QC specimen container 150 from the cold insulation section 84 and heat it for a certain period of time, which causes a time loss. Therefore, in the present embodiment or embodiments, when the "Retest setting: Yes" is included in the QC conditions, the QC specimen container 150 is set in the rack, including the number of tests required for automatic retest.

In the case of case E, four measurement units XN1 to XN4 are designated as objects. Therefore, it is necessary to secure 8 tests for each concentration level, including the initial test and the retest. For level 1, the number of remaining tests of the QC specimen container 150 at position number 1 is 3, which is less than 8. Therefore, for level 1, the QC specimen containers 150 at position numbers 1 and 2 are combined and set in the rack. For level 2, the number of remaining tests of the QC specimen container 150 at position number 4 is 7, which is less than 8. Therefore, for level 2, the QC specimen containers 150 at position numbers 4 and 5 are combined and set in the rack.

FIG. 48 shows case F.

<Case F>

In case F, the following QC conditions are set.

Concentration level to be used: Level 1, Level 2

Object unit of quality control measurement: XN1, XN2, XN3, XN4

Block straddle: Possible

Lot-to-lot difference check: On

In case F, unlike case A, the condition of "Lot-to-lot difference check function on" is added. The lot-to-lot difference check function is a function that measures both the QC specimen of the operating lot and the QC specimen of the new lot with one auto QC schedule. When the lot of QC specimen is switched, sometimes, both the QC specimen of the operating lot and the QC specimen of the new lot are measured by the same measurement unit for a certain period (for example, one week), and the quality control results of the two lots are compared. In other words, there may be a certain overlap period between usage periods of the operating lot and the new lot. This is done to confirm that there is no significant discrepancy between the operating lot and the new lot. The lot-to-lot difference check function is a function that automatically performs auto QC using these two lots.

In case F, it is assumed that the QC specimen list shown in FIG. 48 is stored in the database 820 of the control section 82a. As shown in FIG. 48, for concentration level 1, QC specimen containers 150 of P001 lot and P002 lot are stored in the cold insulation section 84. For level 1, P001 is the operating lot and P002 is the new lot. For level 2, QC specimen containers 150 of Q001 lot and Q002 lot are stored. Q001 is the operating lot and Q002 is the new lot. In this case, for each concentration level, one operating lot and one new lot are combined.

In case F, for example, for level 1, the QC specimen containers 150 at position numbers 1 and 2 are combined, and for level 2, the QC specimen containers 150 at position numbers 4 and 5 are combined. That is, the QC specimen rack 160 housing the QC specimen containers 150 at position numbers 1, 2, 4 and 5 is transported to the measurement units XN1 to 4, and four QC specimens are measured respectively in each measurement unit.

FIG. 49 is an example of a screen 3000 for comparing quality control results of old lot and new lot. The screen 3000 is displayed, for example, on the monitor 92 (see FIG. 7) of the supply unit 80. The monitor 92 may be provided in another place such as a measurement unit. The screen 3000 displays a QC chart 3001 for confirming daily variation of the measured values of the QC specimens as the quality control results. As shown in FIG. 49, when a QC file of the old lot and a QC file of the new lot are read and superposition operation is performed, a QC chart 3002 of the old lot and a QC chart 3003 of the new lot can be superimposed and displayed. The user can confirm a lot-to-lot difference of the quality control results by comparing and confirming the two QC charts. By using the lot-to-lot difference check function of the present embodiment or embodiments, complicated lot switching can be smoothly performed.

Figure 50:
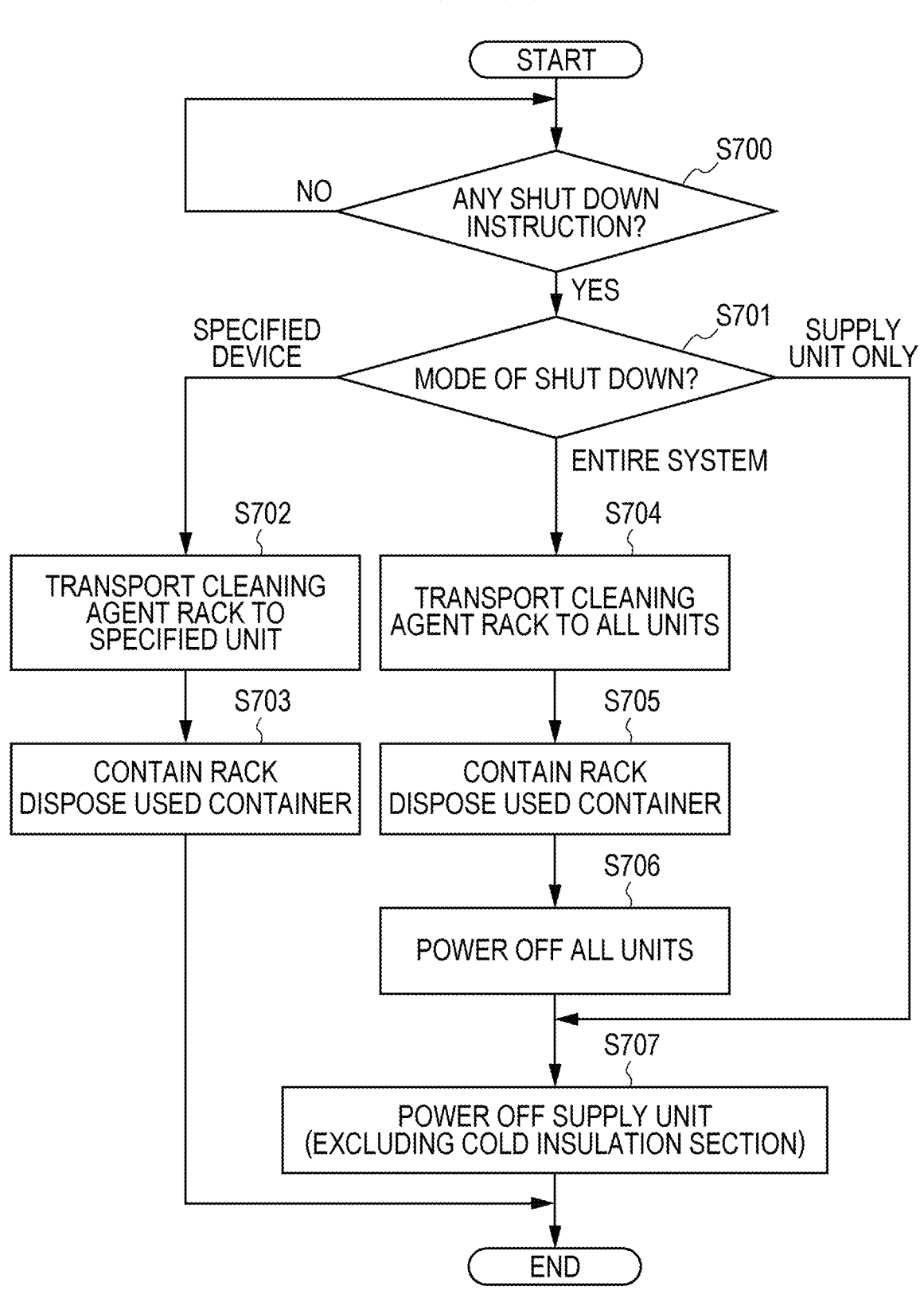
FIG. 50 is a flowchart illustrating a process of a supply unit when receiving a shut down instruction.

FIG. 50 is a flowchart illustrating a process of the supply unit 80 when receiving a shut down instruction. The control section 82a determines whether or not a shut down instruction has been received (step S700). As described with reference to FIG. 20, the control section 82a of the supply unit 80 can receive a shut down instruction from the user by pressing the OK button on the screens 2100 to 2103. When the OK button is pressed on any of the screens, the control section 82a determines that the shut down instruction has been given (YES in step S700).

The control section 82a determines a shut down mode selected by the user (step S701). When shut down is instructed via the designated device screen 2101 in FIG. 20, the control section 82a determines that it is a designated device mode, the control section 82a sets the cleaning agent containers 180 of the number corresponding to the number of devices designated in the screen 2101 in the rack, and the control section 82a controls each part of the supply unit 80 to transport the cleaning agent rack towards the designated unit (step S702). The control of the supply unit 80 regarding the setting and transportation of the cleaning agent is as described with reference to FIG. 34. The control of the measurement units 10A and 10B that received the cleaning agent container 180 is as described with reference to FIG. 39, and the power supply of the unit is automatically turned off when cleaning using the cleaning agent is completed. Although FIG. 39 illustrates the shut down of the measurement unit, the process unit 40 is also automatically turned off after cleaning.

When the cleaning agent rack transported in step S702 returns, the control section 82a contains the rack in the rack housing section 88, the control section 82a controls each part of the supply unit 80 so as to dispose the used cleaning agent container 180 (step S703) to end the process. As a result, only the device designated by the user is shut down.

When shut down of the entire system is instructed via the system screen 2102 in FIG. 20, the control section 82a determines that it is an entire system mode, and the control section 82*a* controls each part of the supply unit 80 so as to transport the cleaning agent rack to all the measurement units 10A and 10B and the process unit 40 (Step S704).

Similar to step S703, the control section 82*a* contains the returned cleaning agent rack in the rack housing section 88, and the control section 82*a* controls each part of the supply unit 80 so as to dispose the used cleaning agent container 180 (step S705). The control section 82*a* sends a command to turn off the power supply to all the units of the specimen analysis system 1 (step S706). As a result, all the devices constituting the specimen analysis system 1 are shut down.

In step S707, the control section 82*a* turns off the power supply of the supply unit 80 to end the process (step S707). However, as described above, the cold insulation section 84 is maintained in the power-on state even after the supply unit 80 is shut down, and the QC specimen is continuously cooled and stored.

When the shut down of the supply unit 80 alone is instructed via the screen 2103 in FIG. 20, the control section 82*a* skips steps S702 to 706, and the control section 82*a* executes the process of step S707 to end the process.

As described above, according to the specimen analysis system 1 and the quality control method described above, the quality control specimen is automatically determined according to the quality control measurement conditions and information on the quality control specimens set by the user, and the quality control specimen is transported to the measurement unit, and the measurement is started. Since the user can freely set the quality control measurement conditions, it is possible to realize quality control measurement that accurately meets the user's needs. It is not necessary for the user to set the quality control material in the system when performing quality control measurement, burden on the user is reduced, and usability is greatly improved.

In addition to the above-described embodiment or embodiments and modifications, the embodiment or embodiments of the quality control method and the specimen analysis system can be appropriately changed in design as long as the object of the invention is not impaired.

Figure 51:
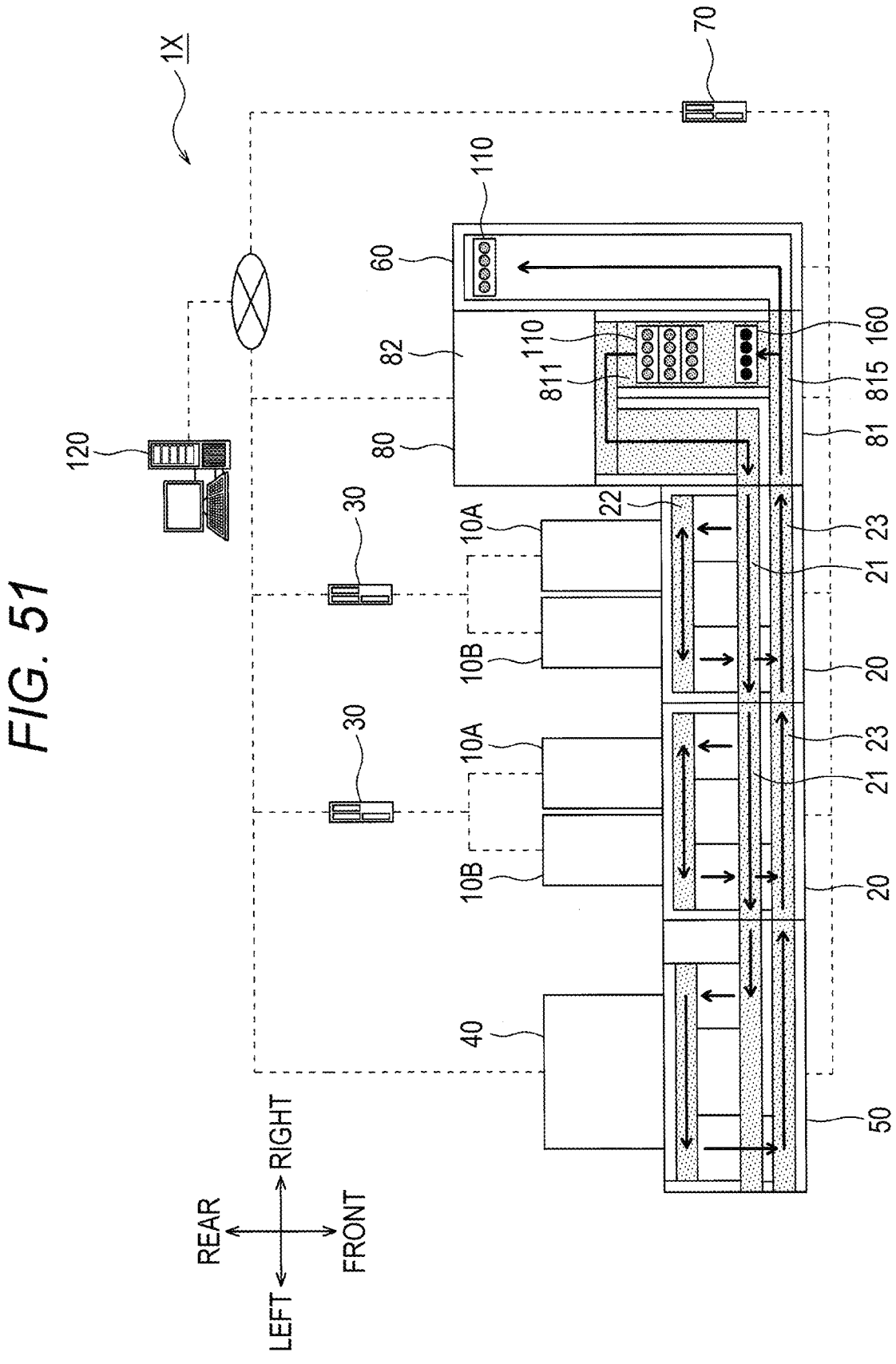
FIG. 51 is a diagram schematically showing a configuration of a first modification of a specimen analysis system.
Figure 52:
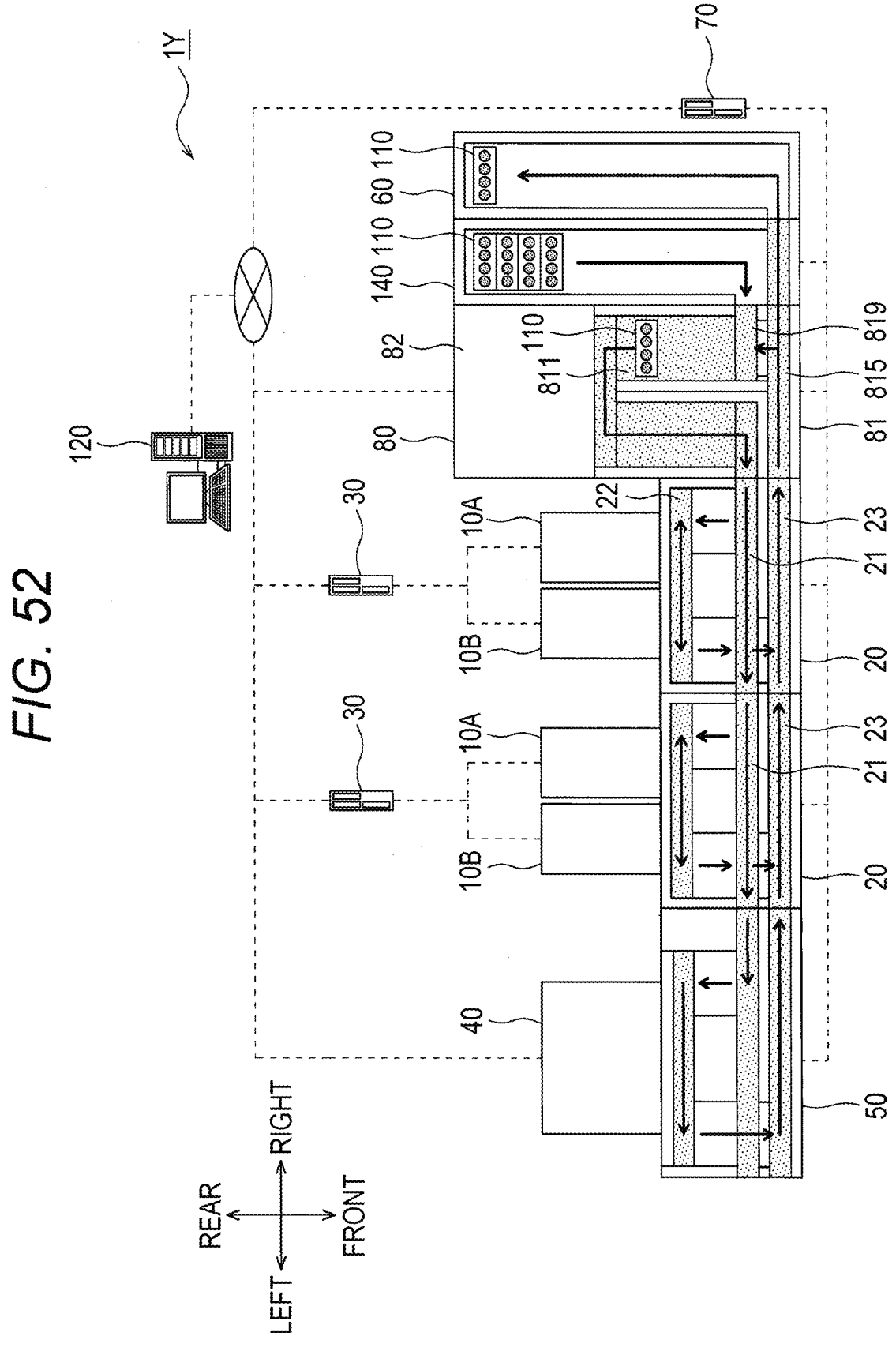
FIG. 52 is a diagram schematically showing a configuration of a second modification of a specimen analysis system.

FIGS. 51 and 52 are diagrams schematically showing configurations of specimen analysis systems 1X and 1Y which are first and second modifications. As shown in FIG. 51, the specimen analysis system 1X differs from the specimen analysis system 1 in that the collection unit 60 is provided adjacent to the right side opposite to the module 10 of the supply unit 80. In the case of the specimen analysis system 1X, the rack transport path of the collection unit 60 is connected to the fifth transport path 815 of the conveyor section 81. While the third transport path 23 and the fifth transport path 815 of the transport unit 20 are transport paths for collecting the QC specimen rack 160 and the cleaning agent rack in the specimen analysis system 1, the third transport path 23 and the fifth transport path 815 are also used for collection of the specimen rack 110 in the specimen analysis system 1X.

As shown in FIG. 52, the specimen analysis system 1Y differs from the specimen analysis systems 1 and 1X in that an additional second supply unit 140 is provided adjacent to the right side of the supply unit 80. The second supply unit 140 is a unit in which the specimen rack 110 or the like is set by the user. The second supply unit 140 does not have a cooling storage function and the like of the QC specimen container 150. In the example shown in FIG. 52, the second supply unit 140 is arranged between the supply unit 80 and the collection unit 60. A rack transport path of the second supply unit 140 is connected to the sixth transport path 819 of the conveyor section 81. In this case, the sixth transport path 819 functions as a transport path for carrying the specimen rack 110 and the like from the second supply unit 140.

Figure 53:
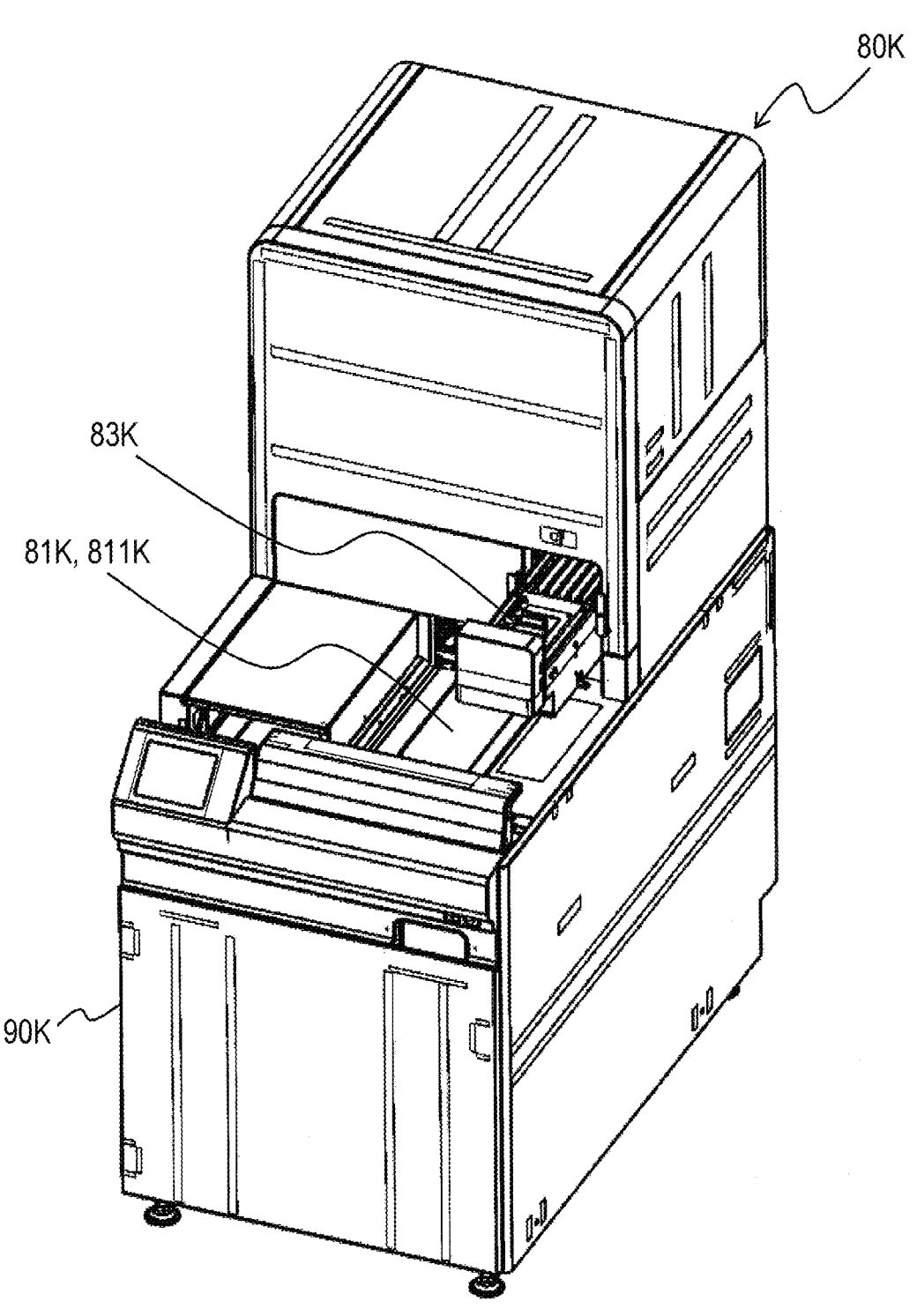
FIG. 53 is a perspective view showing an appearance of a first modification of a supply unit.
Figure 54:
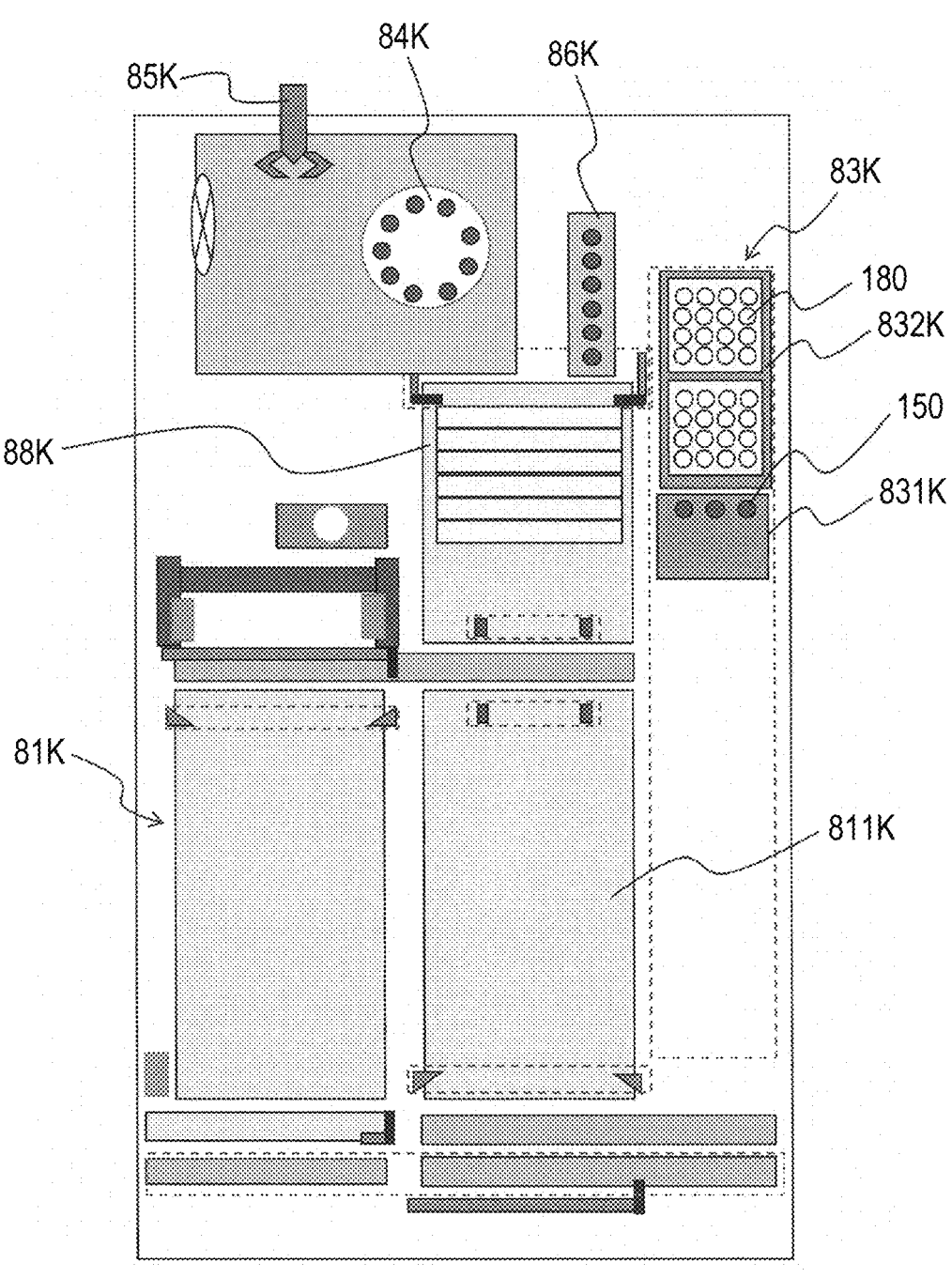
FIG. 54 is a diagram schematically showing a configuration of a first modification of a supply unit.

FIGS. 53 and 54 are diagrams showing a supply unit 80K which is a first modification. The supply unit 80K includes a conveyor section 81K including a first transport path 811K in which a rack is set by the user. A configuration of the conveyor section 81K is the same as that in the case of the supply unit 80. The supply unit 80K further includes a cold insulation section 84K, a transfer section 85K, a heating section 86K, a rack housing section 88K, and a wagon 90K. Although FIG. 54 illustrates the carousel type cold insulation section 84K, a configuration thereof may be the same as that in the case of the supply unit 80. Configurations of the information reading section 86 and the like (not shown) may be the same as those in the case of the supply unit 80.

In the supply unit 80K, the structure of the charging section 83K in which the QC specimen container 150 and the cleaning agent container 180 are set is different from the structure of the charging section 83 of the supply unit 80. The charging section 83K is arranged adjacent to the first transport path 811K and has a pull-out structure slidable in the front-rear direction of the supply unit 80K. The charging section 83K has a first housing portion 831K in which a plurality of QC specimen containers 150 are set, and a second housing portion 832K in which a plurality of cleaning agent containers 180 are set. For example, three QC specimen containers 150 can be set in the first housing portion 831K.

The charging section 83K is configured so that it can be manually pulled forward when the QC specimen container 150 and the cleaning agent container 180 are set in the supply unit 80K. Alternatively, the charging section 83K may be electrically operated. When the charging section 83K is pulled out to the front of the device, the QC specimen container 150 is set in the first housing portion 831K and the charging section 83K is pushed to a predetermined position behind the device, the transfer section 85K transfers the QC specimen container 150 from the first housing portion 831K to the cold insulation section 84K as in the case of the supply unit 80. The cleaning agent container 180 is stored in the second housing portion 832K. For example, a sensor for detecting the number of cleaning agent containers 180 is installed in the supply unit 80K, and the number of cleaning agent containers 180 is displayed in the cleaning agent container inventory window 2006 shown in FIG. 19.

Figure 55:
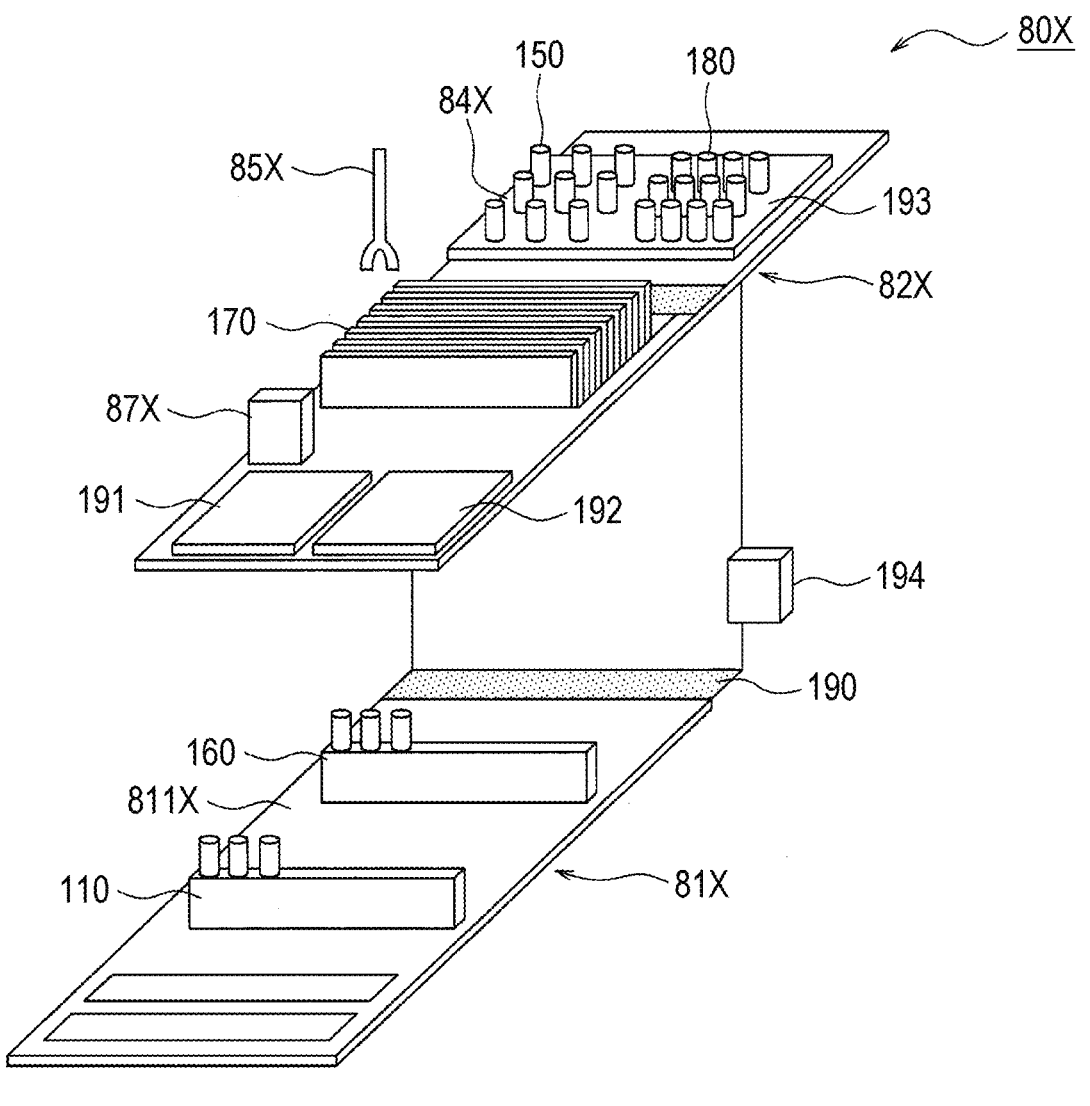
FIG. 55 is a diagram schematically showing a configuration of a second modification of a supply unit.

FIG. 55 is a diagram schematically showing a supply unit 80X which is a second modification. As shown in FIG. 55, the supply unit 80X includes a first floor portion 81X provided with a transport path 811X for transporting the specimen rack 110 and the QC specimen rack 160 to the measurement unit, and a second floor portion 82X provided with a cold insulation section 84X, a cleaning agent container storage section 193 and the like. A lift type moving section 190 that transports the rack between the first floor portion 81X and the second floor portion 82X, and an information reading section 194 that reads the rack ID and the specimen ID of the specimen container 100 and the like from the rack that moves in the moving section 190.

The second floor portion 82X is provided with a transfer section 85X for gripping and transferring the QC specimen container 150 and an information reading section 87X for reading the QC specimen ID of the QC specimen container 150, as in the case of the supply unit 80, and a plurality of empty racks 170 for housing and transporting the QC specimen container 150 and the cleaning agent container 180 are housed. The second floor portion 82X is provided with a first charging and collection section 191 that functions as a charging port and a collection port for the QC specimen container 150, and a second charging and collection section 192 that functions as a charging port and a collection port for the cleaning agent container 180.

As described above, the QC specimen container 150 is adjusted to the measurement temperature in the supply unit, then the QC specimen container 150 is housed in the rack and transported to the measurement unit. When only a part of a plurality of measurement units is operated, it is preferable to transport the QC specimen rack 160 only to the operating measurement unit and not to the stopped measurement unit.

The control section of the supply unit measures time T1 in which the QC specimen container 150 is taken out from the cold insulation section 84 and is placed in a room temperature environment. When the time T1 exceeds predetermined time T2, a process of returning the QC specimen container 150 to the cold insulation section 84 may be executed. In this case, once the time T1 exceeds the time T2, regardless of the measurement result of the QC specimen, that is, even if the measurement result is abnormal when retest is set as the QC conditions, the control section returns the QC specimen container 150 to the cold insulation section 84 without performing retest. According to this process, the QC specimen is prevented from being left in the room temperature environment for a long time, and the state of the QC specimen can be kept good. Alternatively, when the time T1 exceeds the predetermined time T2, the container may be subject to disposal.

The control section of the supply unit determines whether or not the QC specimen container 150 satisfies predetermined continuous use conditions in the collection process of the QC specimen container 150, and the QC specimen container 150 that does not satisfy the continuous use conditions may be discarded (for example, step S606 in FIG. 41). Alternatively, the QC specimen container 150 that does not satisfy the continuous use conditions may be returned to the cold insulation section 84, and cooling storage may be continued as unusable. Since the QC specimen is expensive, automatic disposal of the QC specimen container 150 may not be preferable, and this configuration can meet the needs.

The predetermined continuous use conditions are conditions for determining whether or not the QC specimen container 150 can be used in subsequent quality control measurement. The predetermined continuous use conditions include the expiration date, in addition to the remaining amount of the QC specimen. For example, when the next quality control measurement is the next day, the QC specimen container 150 whose expiration date is today may be disposed as not satisfying the continuous use conditions.

The cold insulation section 84 having a cooling function is exemplified as the storage of the supply unit that stores the QC specimen container 150 in the above embodiment or embodiments. However, the storage may not have a cooling function depending on the type of QC specimen to be used and the like. In addition to the heater and fan, the heating section that heats the QC specimen and adjusts the QC specimen to the measurement temperature may be provided with equipment that assists heating, such as a stirrer, vibration generator, and rotating device such as a carousel. In addition to the heater and fan, the heating section that heats the QC specimen and adjusts the QC specimen to the measurement temperature may be provided with equipment that assists heating, such as a stirrer, vibration generator, and rotating device such as a carousel.

The QC specimen is heated by heating the QC specimen container 150 by a heating means of the heating section 86 in the above embodiment or embodiments. However, the QC specimen may be heated by exposing the QC specimen container 150 to an atmosphere at room temperature. The cold insulation section 84 and the heating section 86 are configured as separate devices, and the cold insulation section 84 and the heating section 86 are provided at different locations in the above embodiment or embodiments. However, for example, the cold insulation section can also be used as the heating section. The Perche element built in the cold insulation section generally has not only a cooling function but also a heating function. Therefore, when the predetermined conditions are satisfied, the Perche element is switched from cooling mode to heating mode, and the QC specimen can be heated.

In the above embodiment or embodiments, the blood cell counter is exemplified as the measurement unit, but the measurement unit is not limited to this, and a blood coagulation test, an immunological test, a biochemical test or the like may be used. The specimen supplied to the measurement unit is not limited to whole blood, and may be plasma, serum, urine, lymph, body cavity fluid, or the like.

The invention claimed is:

1. A specimen analysis system comprising:
at least one analyzer configured to measure blood specimens and quality control specimens used for assurance of quality of measurement on the blood specimens;
a supply apparatus comprising a storage provided with a plurality of holders configured to hold the quality control specimens including first quality control specimens of a first concentration level (FQCS) and second quality control specimens of a second concentration level (SQCS), wherein:
each quality control specimen is assigned a lot number; and
each holder of the plurality of holders is assigned a holder ID;
a transporter configured to transport the quality control specimens to the at least one analyzer, wherein the at least one analyzer is configured to automatically perform quality control measurements on the quality control specimens; and
a controller configured to store information of the quality control specimens in association with the holder ID such that the plurality of holders holding the quality control specimens can be identified, the information including the lot number of each of the quality control specimens,
wherein the controller is configured to perform an automatic quality control operation, wherein in the automatic quality control operation,
(1-1) the controller is configured to:
(1-1-1) identify, from the quality control specimens in the storage, the FQCS which has the lot number that is identical to the lot number of the FQCS used in a previous quality control measurement; (1-1-2) identify the holder ID associated with the lot number of the identified FQCS in order to identify the holder holding the identified FQCS; (1-1-3) cause the supply apparatus to retrieve the identified FQCS from the identified holder;
(1-2) the transporter is configured to transport the retrieved FQCS to the at least one analyzer; and
(1-3) the at least one analyzer is configured to measure the retrieved FQCS to obtain at least one first quality control measurement and to compare the at least one first quality control measurement with a first range having a first upper limit value and a first lower limit value, wherein the at least one first quality control measurement is determined to be normal when the at least one first quality control measurement is within the first range, and wherein the at least one first quality control measurement is determined to be abnormal when the at least one first quality control measurement is out of the first range;

(2-1) the controller is configured to:

(2-1-1) identify, from the quality control specimens in the storage, the SOCS which has the lot number that is identical to the lot number of the SOCS used in the previous quality control measurement;

(2-1-2) identify the holder ID associated with the lot number of the identified SOCS in order to identify the holder holding the identified SOCS;

(2-1-3) cause the supply apparatus to retrieve the identified SOCS from the identified holder;

(2-2) the transporter is configured to transport the retrieved SQCS to the at least one analyzer; and (2-3) the at least one analyzer is configured to measure the retrieved SQCS to obtain at least one second quality control measurement; and to compare the at least one second quality control measurement with a second range having a second upper limit value and a second lower limit value, wherein the at least one second quality control measurement is determined to be normal when the at least one second quality control measurement is within the second range, and wherein the at least one second quality control measurement is determined to be abnormal when the at least one second quality control measurement is out of the second range.

2. The system according to claim 1, wherein the storage is configured to store third quality control specimens of a third concentration level (TQCSs) in addition to the FOCSs and SQCSs, and the controller is configured to (ix) identify, from the quality control specimens in the storage, the TQCS which has the lot number that is identical to the lot number of TQCS used in the previous quality control measurement; (x) identify the holder ID associated with the lot number and the identified TOCS in order to identify the holder holding the identified TOCS; (xi) cause the supply apparatus to retrieve the identified TOCS from identified the holder; (xii) cause the transporter to transport the retrieved TOCS to the at least one analyzer.

3. The system according to claim 1, wherein the quality control specimens include blood cells, and the at least one analyzer is configured to measure the blood cells in the determined first and second quality control specimens.

4. The system according to claim 1, wherein each of the first and second quality control specimens is stored in a quality control specimen container that is sealed with a cap.

5. The system according to claim 4, wherein the at least one analyzer further comprises a suction tube configured to penetrate the cap of the respective quality control specimen containers and to suck each of the first and second quality control specimens from the respective quality control specimen containers.

6. The system according to claim 4, wherein the at least one analyzer further comprises an agitation mechanism configured to agitate each of the quality control specimen containers.

7. The system according to claim 4, wherein the transporter is configured to transport at least one rack holding the quality control specimen containers.

8. The system according to claim 4, wherein the supply apparatus further comprises a first information reader configured to read machine-readable labels or tags attached to quality control specimen containers storing each of the first and second quality control specimens to acquire the information.

9. The system according to claim 8, wherein the at least one analyzer further comprises a second information reader configured to read machine-readable labels or tags attached to quality control specimen containers, and a cell counter configured to count blood cells in the first and second quality control specimens stored by the quality control specimen containers.

10. The system according to claim 1, wherein the controller is configured to create quality control charts for each of the first and second concentration levels based on measurement results of the determined first and second quality control specimens.

11. The system according to claim 1, wherein the controller is configured to control the transporter to return the measured first and second quality control specimens to the storage.

12. The system according to claim 11, wherein the controller is configured to control the supply apparatus to take out the returned first and second quality control specimens and to control the transporter to transport the returned first and second quality control specimens to the at least one analyzer.

13. The system according to claim 1, wherein the controller is configured to receive registration of a schedule for automatically executing a quality control measurement and to control the supply apparatus to take out the first and second quality control specimens from the storage and to set them in a rack, and control the transporter to transport the rack to the at least one analyzer, according to the schedule.

14. The system according to claim 1, wherein the information stored by the controller further includes remaining amount information of each of the first and second quality control specimens.

15. The system according to claim 1, wherein the information stored by the controller further includes expiration date of each of the first and second quality control specimens.

16. The system according to claim 1, wherein the information stored by the controller further includes remaining amount information of each of the first and second quality control specimens;

the information stored by the controller further includes expiration date of each of the first and second quality control specimens;

the system further comprises a monitor configured to display the information including remaining amount information and/or expiration date of each of the first and second quality control specimens.

17. The system according to claim 1, wherein, the storage comprises holding portions configured for holding each of the first and second quality control specimens, and

the controller is configured to store the information in association with position information of the holding portions in which each of the first and second quality control specimens is held.

18. The system according to claim 1, wherein
the storage includes a cold insulation storage configured for cooling and storing the quality control specimens, and
each of the first and second quality control specimens is taken out from the cold insulation storage.

19. The system according to claim 1, wherein
the at least one analyzer is configured to store quality control files to record measurement values of quality control measurements, the quality control files created for each of the lot numbers, and
the at least one analyzer is configured to update a first quality control file corresponding to the lot number of the first quality control specimen by adding a measurement value obtained by a quality control measurement of the first quality control specimen and updates a second quality control file corresponding to the lot number of the second quality control specimen by adding a measurement value obtained by a quality control measurement of the second quality control specimen.

20. A supply apparatus supplying quality control specimens to at least one analyzer that is configured to measure a blood specimen and to automatically perform a quality control measurement on the supplied quality control specimens, the supply apparatus comprising:
a storage provided with a plurality of holders configured to hold quality control specimens including first quality control specimens of a first concentration level (FQCS) and second quality control specimens of a second concentration level (SQCS), wherein:
each quality control specimen is assigned a lot number; and
each holder of the plurality of holders is assigned a holder ID;
a take-out mechanism configured to take out the quality control specimens from the plurality of holders;
a controller configured to store information of the quality control specimens in association with the holder ID with which the holder holding the quality control specimens can be identified, the information including the lot number of each of the quality control specimens;
wherein the controller is configured to perform an automatic quality control operation, wherein in the automatic quality control operation,
(1-1) the controller is configured to:
(1-1-1) identify, from the quality control specimens, the FQCS which has the lot number that is identical to the lot number of the quality control specimen used in a previous quality control measurement; (1-1-2) identify the holder ID associated with the lot number of the FQCS in order to identify the holder holding the identified FQCS; (1-1-3) cause the take-out mechanism to take out the identified FQCS from the identified holder; and (1-1-4) cause the take-out mechanism to transport the taken out FQCS to the at least one analyzer;
(1-2) the at least one analyzer is configured to measure the retrieved FQCS to obtain at least one first quality control measurement and to compare the at least one first quality control measurement with a first range having a first upper limit value and a first lower limit value, wherein the at least one first quality control measurement is determined to be normal when the at least one first quality control measurement is within the first range, and wherein the at least one first quality control measurement is determined to be abnormal when the at least one first quality control measurement is out of the first range; and
(2-1) the controller is configured to:
(2-1-1) identify, from the quality control specimens, the SQCS which has the lot number that is identical to the lot number of a quality control specimen used in a previous quality control measurement; (2-1-2) identify the holder ID associated with the lot number of the identified SQCS in order to identify the holder holding the identified SQCS; (2-1-3) cause the take-out mechanism to take out the identified SQCS from the identified holders; and (2-1-4) cause the take-out mechanism to transport the taken out SQCS to the at least one analyzer;
(2-2) the at least one analyzer is configured to measure the retrieved SQCS to obtain at least one second quality control measurement and to compare the at least one second quality control measurement with a second range having a second upper limit value and a second lower limit value, wherein the at least one second quality control measurement is determined to be normal when the at least one second quality control measurement is within the second range, and wherein the at least one second quality control measurement is determined to be abnormal when the at least one second quality control measurement is out of the second range.

21. The supply apparatus according to claim 20, wherein
the storage is configured to store third quality control specimens of a third concentration level (TQCS) in addition to the FQCS and SQCS, and
the controller is configured to (ix) identify, from the quality control specimens, the TQCS which has the lot number that is identical to the lot number of a quality control specimen used in a previous quality control measurement; (x) identify the holder ID associated with of the identified TOCS in order to identify the holder holding the identified TOCS; (xi) cause the take-out mechanism to take out the identified TOCS from the holders; (xii) cause the take-out mechanism to transport the taken out TOCS to the at least one analyzer.

* * * * *